US008298561B2

(12) United States Patent  
Alessi et al.

(10) Patent No.: US 8,298,561 B2  
(45) Date of Patent: Oct. 30, 2012

(54) RAPID ESTABLISHMENT AND/OR TERMINATION OF SUBSTANTIAL STEADY-STATE DRUG DELIVERY

(75) Inventors: Thomas R. Alessi, Hayward, CA (US); Kenneth L. Luskey, Saratoga, CA (US)

(73) Assignee: Intarcia Therapeutics, Inc., Hayward, CA (US)

(*) Notice: Subject to any disclaimer, the term of this patent is extended or adjusted under 35 U.S.C. 154(b) by 203 days.

(21) Appl. No.: 12/924,175

(22) Filed: Sep. 21, 2010

(65) Prior Publication Data

US 2011/0076317 A1    Mar. 31, 2011

Related U.S. Application Data

(60) Provisional application No. 61/277,724, filed on Sep. 28, 2009, provisional application No. 61/358,112, filed on Jun. 24, 2010.

(51) Int. Cl.
*A61F 13/00* (2006.01)
*A61K 9/14* (2006.01)
*A61K 9/50* (2006.01)

(52) U.S. Cl. ............... 424/422; 424/489; 424/499
(58) Field of Classification Search ............... None
See application file for complete search history.

(56) References Cited

U.S. PATENT DOCUMENTS

| | | |
|---|---|---|
| 5,728,396 A | 3/1998 | Peery et al. |
| 5,904,935 A | 5/1999 | Eckenhoff et al. |
| 5,932,547 A | 8/1999 | Stevenson et al. |
| 5,972,370 A | 10/1999 | Eckenhoff et al. |
| 5,997,527 A | 12/1999 | Gumucio et al. |
| 6,113,938 A | 9/2000 | Chen et al. |
| 6,124,261 A | 9/2000 | Stevenson et al. |
| 6,130,200 A | 10/2000 | Brodbeck et al. |
| 6,132,420 A | 10/2000 | Dionne et al. |
| 6,190,350 B1 | 2/2001 | Davis et al. |
| 6,235,712 B1 | 5/2001 | Stevenson et al. |
| 6,270,787 B1 | 8/2001 | Ayer |
| 6,287,295 B1 | 9/2001 | Chen et al. |
| 6,331,311 B1 | 12/2001 | Brodbeck et al. |
| 6,375,978 B1 | 4/2002 | Kleiner et al. |
| 6,395,292 B2 * | 5/2002 | Peery et al. ............ 424/422 |
| 6,468,961 B1 | 10/2002 | Brodbeck et al. |
| 6,508,808 B1 | 1/2003 | Carr et al. |
| 6,524,305 B1 | 2/2003 | Peterson et al. |
| 6,544,252 B1 | 4/2003 | Theeuwes et al. |
| 6,673,767 B1 | 1/2004 | Brodbeck et al. |
| 6,939,556 B2 | 9/2005 | Lautenbach |
| 7,014,636 B2 | 3/2006 | Gilbert |
| 7,074,423 B2 | 7/2006 | Fereira et al. |
| 7,163,688 B2 | 1/2007 | Peery et al. |
| 7,207,982 B2 | 4/2007 | Dionne et al. |
| 7,241,457 B2 | 7/2007 | Chen et al. |
| 7,258,869 B1 | 8/2007 | Berry et al. |
| 7,407,499 B2 | 8/2008 | Trautman |
| 7,727,519 B2 | 6/2010 | Moran |
| 2002/0034532 A1 | 3/2002 | Brodbeck et al. |
| 2003/0211974 A1 | 11/2003 | Brodbeck et al. |
| 2004/0224903 A1 | 11/2004 | Berry et al. |
| 2005/0008661 A1 | 1/2005 | Fereira et al. |
| 2005/0010196 A1 | 1/2005 | Fereira et al. |
| 2005/0101943 A1 | 5/2005 | Ayer et al. |
| 2005/0112188 A1 | 5/2005 | Eliaz et al. |
| 2005/0175701 A1 | 8/2005 | Pan et al. |
| 2005/0266087 A1 | 12/2005 | Junnarkar et al. |
| 2005/0276856 A1 | 12/2005 | Fereira et al. |
| 2006/0013879 A9 | 1/2006 | Brodbeck et al. |
| 2006/0141040 A1 | 6/2006 | Chen et al. |
| 2006/0142234 A1 | 6/2006 | Chen et al. |
| 2006/0193918 A1 | 8/2006 | Rohloff et al. |
| 2006/0216242 A1 | 9/2006 | Rohloff et al. |
| 2006/0246138 A1 | 11/2006 | Rohloff et al. |
| 2006/0263433 A1 | 11/2006 | Ayer et al. |
| 2007/0027105 A1 | 2/2007 | Junnarkar et al. |
| 2007/0248572 A1 | 10/2007 | Moran |
| 2007/0281024 A1 | 12/2007 | Lautenbach et al. |
| 2008/0038316 A1 * | 2/2008 | Wong et al. ............ 424/426 |
| 2008/0091176 A1 | 4/2008 | Alessi et al. |
| 2008/0200383 A1 * | 8/2008 | Jennings et al. ............ 514/12 |
| 2008/0260840 A1 | 10/2008 | Alessi et al. |
| 2009/0202608 A1 | 8/2009 | Alessi et al. |
| 2010/0092566 A1 | 4/2010 | Alessi et al. |
| 2010/0185184 A1 | 7/2010 | Alessi et al. |

FOREIGN PATENT DOCUMENTS

| | | |
|---|---|---|
| WO | WO/2008/021133 | 2/2008 |
| WO | WO/2010/044867 | 4/2010 |

OTHER PUBLICATIONS

Rohloff, et al., "DUROS Technology Delivers Peptides and Proteins at Consistent Rate Continuously for 3 to 12 Months," Journal of Diabetes Science and Technology, vol. 2, Issue 3, May 1, 2008, pp. 461-467.

Nielsen, L.L., "Incretin mimetics and DPP-IV inhibitors for the treatment of type 2 diabetes," Drug Discovery Today, vol. 10, No. 10, May 15, 2005, pp. 703-710.

* cited by examiner

*Primary Examiner* — Susan Tran

(74) *Attorney, Agent, or Firm* — Gary R. Fabian; Barbara G. McClung

(57) ABSTRACT

The present invention is directed to treatment methods for a disease or condition, in a subject in need of such treatment, that provide alternatives to treatment by injection that give, relative to treatment by injection, improved treatment outcomes, 100% treatment compliance, reduced side effects, and rapid establishment and/or termination of substantial steady-state drug delivery. The method typically includes providing continuous delivery of a drug from an implanted osmotic delivery device, wherein substantial steady-state delivery of the drug at therapeutic concentrations is typically achieved within about 7 days or less after implantation of the osmotic delivery device in the subject and the substantial steady-state delivery of the drug from the osmotic delivery device is continuous over a period of at least about 3 months. In one embodiment, the present invention is directed to treatment of type 2 diabetes mellitus using incretin mimetics.

14 Claims, 16 Drawing Sheets

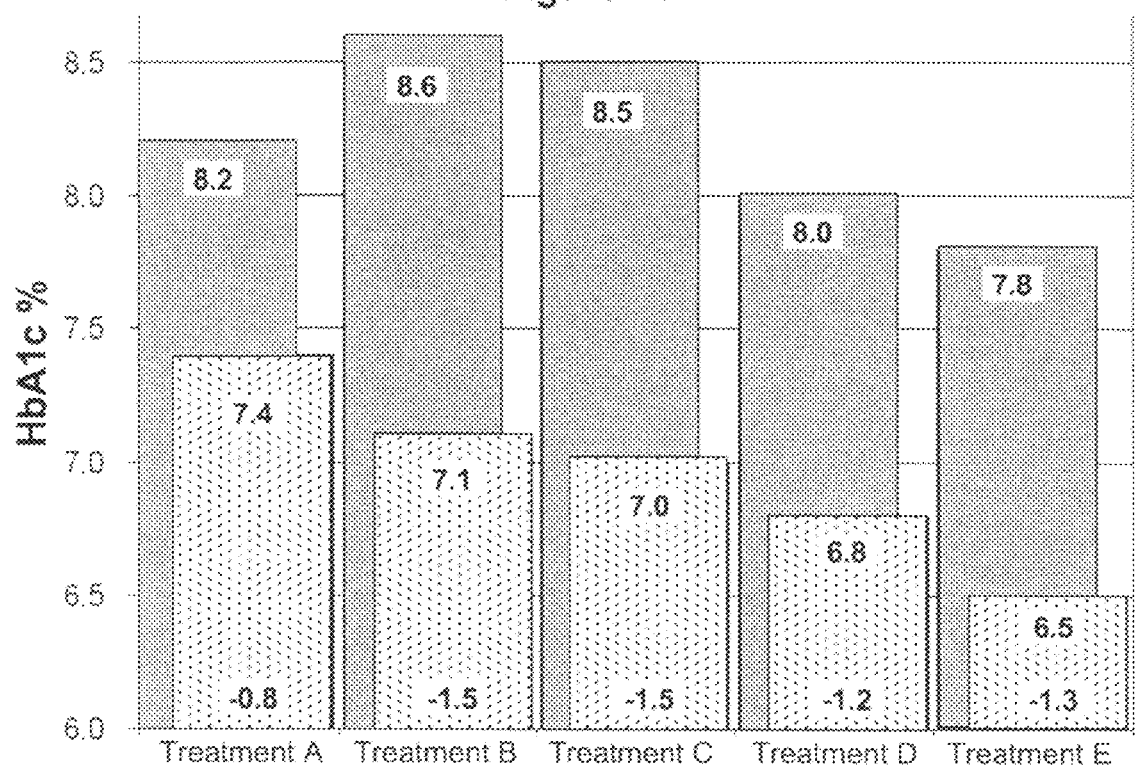
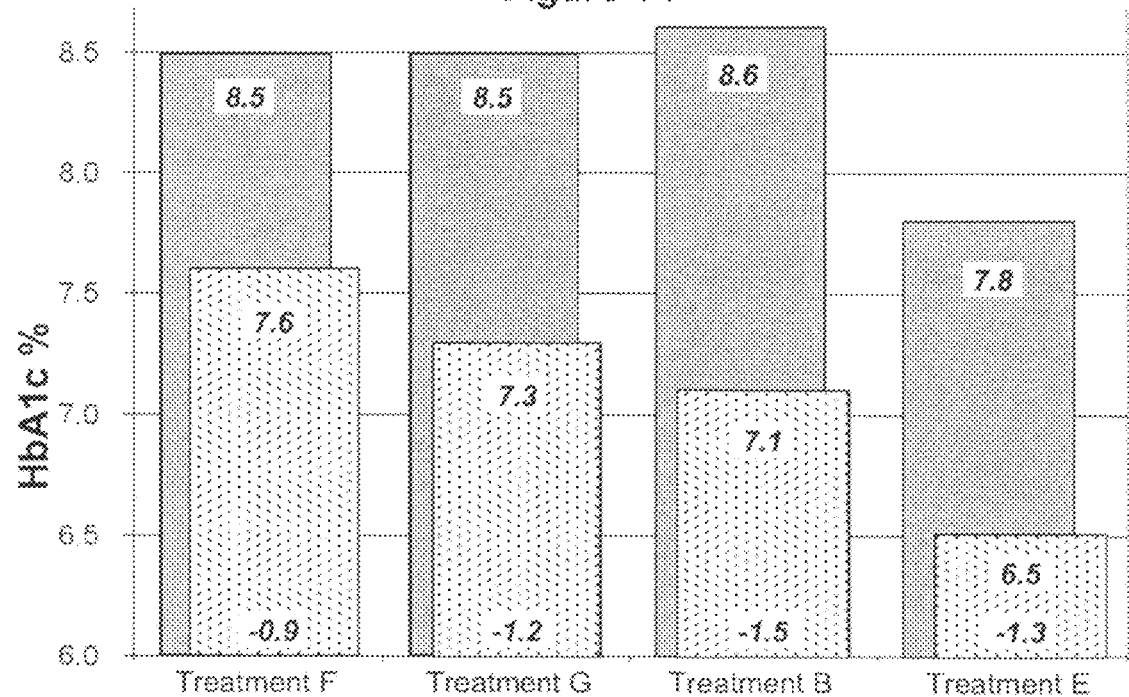

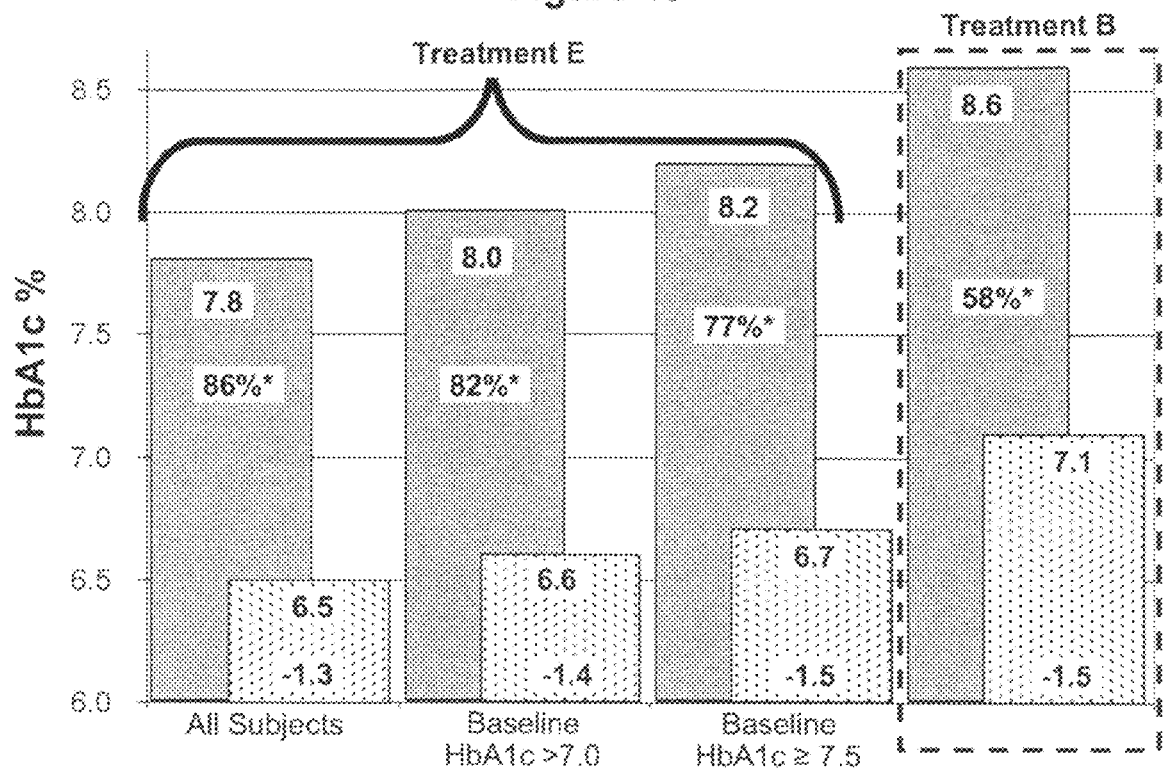
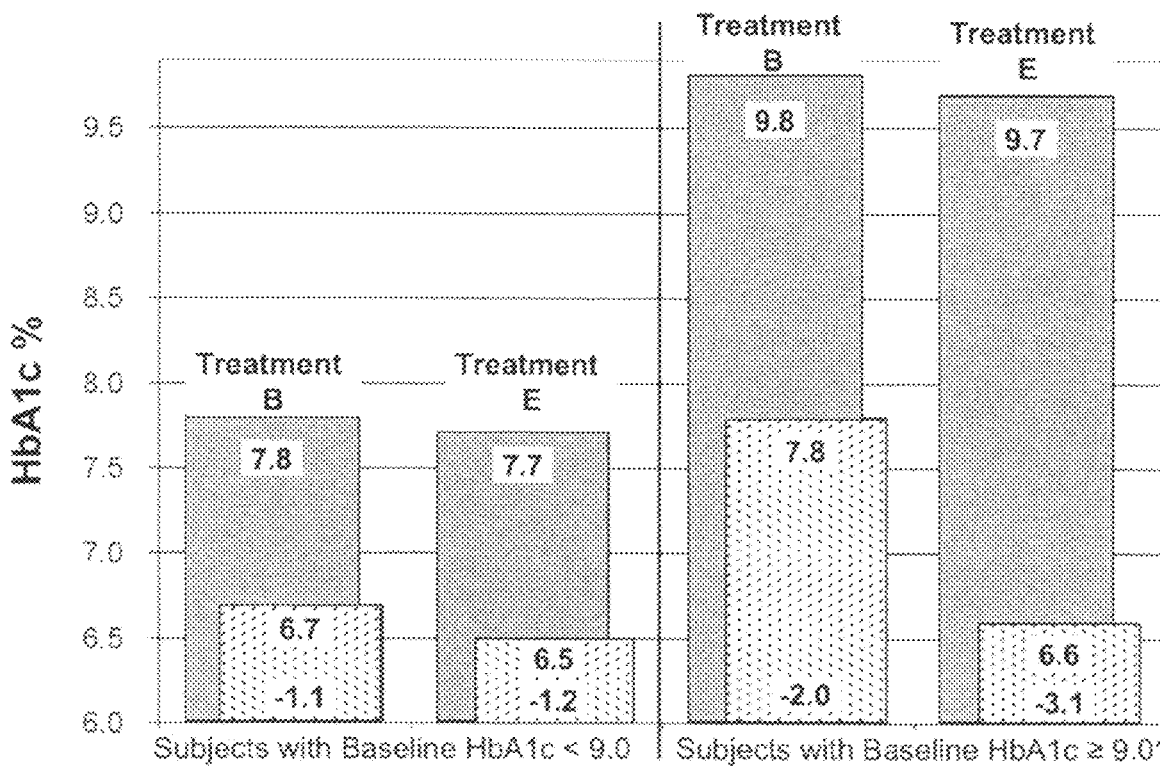

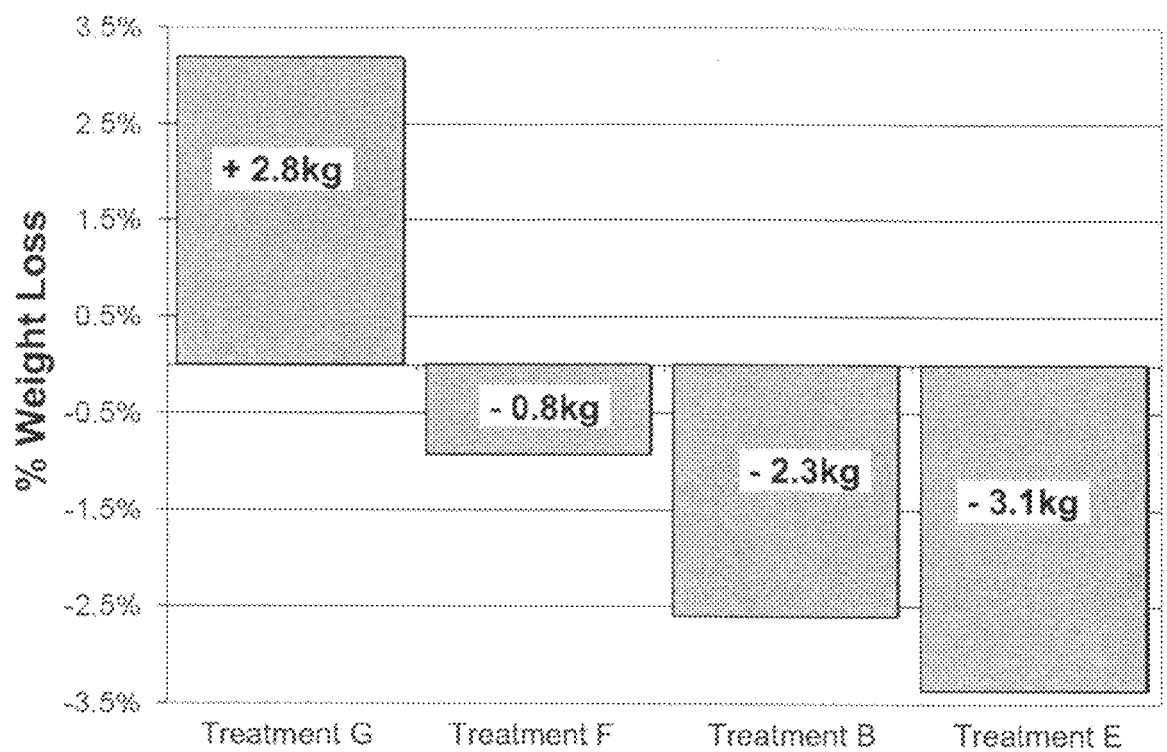

RAPID ESTABLISHMENT AND/OR TERMINATION OF SUBSTANTIAL STEADY-STATE DRUG DELIVERY

CROSS-REFERENCE TO RELATED APPLICATIONS

This application claims the benefit of U.S. Provisional Application Ser. 61/277,724, filed 28 Sep. 2009, and U.S. Provisional Application Ser. No. 61/358,112, filed 24 Jun. 2010, which applications are herein incorporated by reference in their entireties.

TECHNICAL FIELD

The present invention relates to organic chemistry, formulation chemistry, and peptide chemistry applied to pharmaceutical research and development. Aspects of the present invention include, but are not limited to, methods of treatment for a disease or condition in a subject in need of such treatment. In one embodiment the disease is type 2 diabetes mellitus.

BACKGROUND OF THE INVENTION

A variety of drug dosage forms and methods of drug administration have been developed for delivery of drugs to mammals, in particular, for delivery of drugs to humans (see, e.g., the Merck Manual of Diagnosis and Therapy, 18th edition, Published by Merck Sharp & Dohme Corp., Whitehouse Station, N.J.). Such dosage forms include, for example, use of the following routes of administration: oral; injection (e.g., intravenously, intramuscularly, intrathecally, or subcutaneously); implantation (e.g., subcutaneous); and across a skin or mucosal barrier (e.g., sublingual, rectal, vaginal, ocular, nasal, inhalation into the lungs, topical, or transdermal). Each route of administration has specific purposes, advantages, and disadvantages.

The oral route of administration is the most common and generally considered to be the most convenient. Oral administration, however, poses some limitations because drugs administered by this route are exposed to the harsh conditions of the digestive system. Other routes of administration may be required when the oral route cannot be used.

When drugs are prepared for administration by injection (e.g., subcutaneous, intramuscular, intravenous, or intrathecal administration), the drug can be formulated in a variety of ways including formulations that prolong drug absorption from the injection site for hours, days, or longer. Such formulations are typically used for subcutaneous injection. Injectable products formulated for prolonged delivery typically are not administered as often as injectable drug products having more rapid absorption. Subcutaneous administration is used for many protein or peptide drugs because such drugs are typically broken down by the digestive system to inactive forms if taken orally. Subcutaneous administration of a drug typically requires frequent self-injection, for example, one or more times daily or once-weekly injections.

When a large volume of a drug product is required, intramuscular administration is generally the preferred route of administration. Typically, intramuscular administration of drugs is by injection into the muscle of the upper arm, thigh, or buttock. The rate of drug absorption into the bloodstream in large part depends on the blood supply to the muscle, that is, the more blood supply the faster the drug is absorbed.

Intravenous drug administration requires that a needle be inserted directly into a vein. A drug may be given in a single dose or continuously infused. For infusion, a drug solution is either delivered using gravity (e.g., from a collapsible plastic bag) or using an infusion pump through a tube inserted in a vein, usually in the forearm. An intravenous injection can be more difficult to administer than a subcutaneous or intramuscular injection, for example, because inserting a needle or catheter into a vein may be difficult, drugs typically must be mixed within a relatively short time before beginning administration, there is an increased chance of infection (e.g., abscessed infections of injection sites caused by lack of hygiene and/or a lack of correct aseptic technique), and over time there is scarring damage to the peripheral veins.

When drugs are administered by intravenous injection it is often desirable for health care practitioners to closely monitor subjects for signs that the drug is working and that the drug is not causing undesired side effects. Typically, the effect of intravenously administered drugs tends to last for a shorter periods of time than drugs administered by subcutaneous injection or intramuscular injection. Therefore, some drugs must be administered by continuous infusion to provide appropriate therapeutic effect. Because of the difficulties associated with intravenous drug administration it is most typically used in hospital or skilled care settings; it is rarely used for long-term self-administered treatment.

A number of complications negatively impact compliance with injection treatment regimens, including, but not limited to, the following. A subject being needle phobic, which is particularly troublesome to a subject when a drug must be self-injected over extended periods of time. Compliance can also be complicated by the inconvenience of administration of a drug by injection, for example, when subjects are in public or busy with daily activities. Also, frequent self-administration of a drug reminds subjects of their disease state and carries a stigma associated with the disease and/or treatment.

The implantable osmotic drug delivery devices of the present invention, and use of these osmotic delivery devices in methods for the treatment of diseases or conditions in subjects in need of treatment, uniquely address unmet needs of previously described drug dosage forms and methods of treatment. For example, the present invention provides treatment of subjects at a target drug dose that is continuously administered over time with the ability to rapidly establish and sustain over time substantial steady-state drug delivery while also providing the ability to rapidly terminate administration of the drug. Heretofore, drug administration via injection has not typically been able to provide rapid establishment and long-term maintenance (e.g., three months or more) of steady-state drug delivery and, even if that were possible, treatment using drugs administered by injection (e.g., drugs formulated for prolonged delivery) has not been able to be rapidly terminated. The present invention also provides for enhanced tolerization of subjects to drug dose escalation relative to dose escalation performed by administration of drug by injection.

SUMMARY OF THE INVENTION

The present invention generally relates to improved methods of treating diseases or conditions in subjects in need of treatment, wherein the methods of the invention provide rapid establishment and/or rapid termination of substantial steady-state drug delivery. Further, the present invention relates to methods of escalating drug dose that provide improved tolerization of subjects to increased drug dose levels relative to dose escalation by standard drug injection methods. Preferred subjects for the methods of the present invention are humans.

In a first aspect, the present invention relates to methods of treating type 2 diabetes mellitus in a subject in need of treatment. The method comprises providing continuous delivery of an incretin mimetic from an osmotic delivery device, wherein substantial steady-state delivery of the incretin mimetic at a therapeutic concentration is achieved within a time period of about 7 days or less after implantation of the osmotic delivery device in the subject. The substantial steady-state delivery of the incretin mimetic from the osmotic delivery device is typically continuous over an administration period of at least about 3 months. In some embodiments of the invention, the substantial steady-state delivery of the incretin mimetic at therapeutic concentrations is achieved after implantation of the osmotic delivery device in the subject within a time period selected from the group consisting of about 5 days or less, about 4 days or less, about 3 days or less, about 2 days or less, or about 1 day or less.

The substantial steady-state delivery of the incretin mimetic from the osmotic delivery device is continuous over an administration period of, for example at least about 3 months to about a year, at least about 4 months to about a year, at least about 5 months to about a year, at least about 6 months to about a year, at least about 8 months to about a year, or at least about 9 months to about a year.

The method can further comprise providing a significant decrease in the subject's fasting plasma glucose concentration after implantation of the osmotic delivery device in the subject, relative to the subject's fasting plasma glucose concentration before implantation of the osmotic delivery device. The decrease is typically obtained within, for example, about 7 days or less, about 6 days or less, about 5 days or less, about 4 days or less, about 3 days or less, about 2 days or less, or about 1 day or less. Normally, a significant decrease in fasting plasma glucose is maintained over the administration period.

Also, the method can further comprising the capability to terminate the continuous delivery of the incretin mimetic such that the concentration of the incretin mimetic is substantially undetectable in a blood sample from the subject within about 6 half-lives or less, about 5 half-lives or less, about 4 half-lives or less, or about 3 half-lives or less of the incretin mimetic after termination of continuous delivery. When exenatide is the incretin mimetic, the method can further comprise the capability to terminate the continuous delivery such that the concentration of exenatide is substantially undetectable in a blood sample from the subject after termination of continuous delivery in a number of hours selected from the group consisting of less than about 72 hours, less than about 48 hours, less than about 24, and less than about 12 hours. In one embodiment, termination of continuous delivery is accomplished by removal of the osmotic delivery device from the subject. The incretin mimetic is, for example, detected by a radioimmunoassay.

Osmotic delivery devices for use in the methods of the present invention can comprise the components described herein including, but note limited to, a reservoir, a semipermeable membrane, an osmotic engine, a piston, a suspension formulation, and a diffusion moderator.

Suspension formulations for use in the present invention typically comprise a particle formulation comprising an incretin mimetic, and a vehicle formulation. Examples of incretin mimetics useful in the practice of the present invention include, but are not limited to, exenatide peptides, exenatide peptide analogs, exenatide peptide derivatives, GLP-1 peptides, GLP-1 peptide analogs, or GLP-1 peptide derivatives. Examples of preferred incretin mimetics useful in the practice of the present invention include exenatide having the amino acid sequence of exendin-4, lixisenatide, GLP-1 (7-36), liraglutide, albiglutide, and taspoglutide. In some embodiments, the vehicle formulation comprises a solvent (e.g., benzyl benzoate, lauryl lactate, and/or lauryl alcohol) and a polymer (e.g., polyvinylpyrrolidone).

In some embodiments of the present invention, the continuous delivery provides to the subject a mcg/day dose of exenatide selected from the group consisting of about 10 mcg/day, about 20 mcg/day, about 30 mcg/day, about 40 mcg/day, about 60 mcg/day, and about 80 mcg/day.

In another embodiment of the present invention, the method further comprises a first continuous administration period of the incretin mimetic at a first mcg/day dose that is followed by a second continuous administration period providing a dose escalation of the incretin mimetic to a second mcg/day dose, wherein the second mcg/day dose is greater than the first mcg/day dose. The first mcg/day dose is, for example, delivered by a first osmotic delivery device and the second mcg/day dose is delivered by a second osmotic delivery device, and delivery of the incretin mimetic from at least the first or the second osmotic delivery device is continuous over the administration period of at least about 3 months. In one embodiment, the second mcg/day dose is at least two times greater than the first mcg/day dose. The method can further comprise at least one more continuous administration period providing a dose escalation of the incretin mimetic to a higher mcg/day dose relative to the second mcg/day dose.

Exemplary dose escalations for exenatide are as follows: about 10 mcg/day followed by about 20 mcg/day; about 10 mcg/day followed by about 40 mcg/day; about 10 mcg/day followed by about 60 mcg/day; about 10 mcg/day followed by about 80 mcg/day; about 20 mcg/day followed by about 40 mcg/day; about 20 mcg/day followed by about 60 mcg/day; about 20 mcg/day followed by about 80 mcg/day; about 40 mcg/day followed by about 60 mcg/day; about 40 mcg/day followed by about 80 mcg/day; or about 60 mcg/day followed by about 80 mcg/day.

In a second aspect, the present invention relates to a method of treating a disease or condition in a subject in need of treatment. The method typically comprises providing continuous delivery of a drug from an osmotic delivery device, wherein substantial steady-state delivery of the drug at therapeutic concentrations is achieved within a time period of about 7 days or less after implantation of the osmotic delivery device in the subject. The substantial steady-state delivery of the drug from the osmotic delivery device is usually continuous over an administration period of at least about 3 months, wherein the drug has a half-life. In one embodiment, the method comprises the proviso that the disease or condition is not prostate cancer.

The method can further comprise the capability to terminate the continuous delivery such that the concentration of the drug is substantially undetectable in a blood sample from the within about 6 half-lives or less, about 5 half-lives or less, about 4 half-lives or less, or about 3 half-lives or less of the drug after termination of continuous delivery. In one embodiment, termination of continuous delivery is accomplished by removal of the osmotic delivery device from the subject. The drug is, for example, detected by a radioimmunoassay or chromatography.

In another embodiment of the present invention, the method further comprises a first continuous administration period of the drug at a first dose/day that is followed by a second continuous administration period providing a dose escalation of the drug to a second dose/day, wherein the second dose/day is greater than the first dose/day. The first dose/day is, for example, delivered by a first osmotic delivery device and the second dose/day dose is delivered by a second osmotic delivery device, and delivery of the drug from at least the first or the second osmotic delivery device is continuous over the administration period of at least about 3 months. The method can further comprise at least one more continuous administration period providing a dose escalation of the drug to a higher dose/day relative to the second dose/day.

Osmotic delivery devices for use in the methods of the present invention can comprise the components described herein including, but not limited to, a reservoir, a semi-permeable membrane, an osmotic engine, a piston, a drug formulation or a suspension formulation, and a diffusion moderator. Drug formulations typically comprise a drug and a vehicle formulation.

Suspension formulations for use in the present invention typically comprise a particle formulation comprising a drug, and a vehicle formulation. In some embodiments, the drug is a polypeptide, for example, a recombinant antibody, antibody fragment, humanized antibody, single chain antibody, monoclonal antibody, avimer, human growth hormone, epidermal growth factor, fibroblast growth factor, platelet-derived growth factor, transforming growth factor, nerve growth factor, a cytokine, or an interferon. In some embodiments, the vehicle formulation comprises a solvent (e.g., benzyl benzoate, lauryl lactate, and/or lauryl alcohol) and a polymer (e.g., polyvinylpyrrolidone).

These and other embodiments of the present invention will readily occur to those of ordinary skill in the art in view of the disclosure herein.

Figure 10:
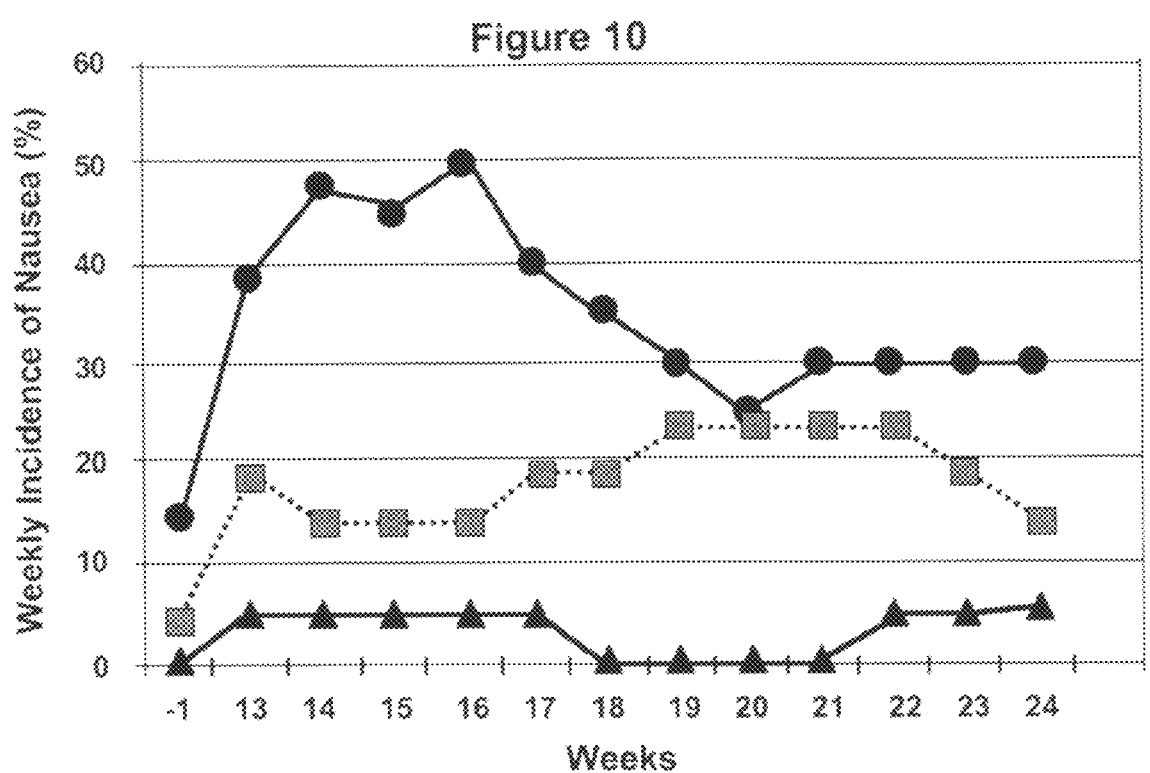

FIG. 10 presents the extension phase (weeks 13-24) data for incidence of nausea over time. The first point (−1 Week) shows the incidence of nausea the week prior to randomization and the beginning of the extension phase treatment protocol. The vertical axis is the Weekly Incidence of Nausea percent (%) and the horizontal axis is the time of treatment in Weeks. In the figure, the data for continuous delivery using implantable osmotic devices delivering 20 mcg/day of exenatide is presented as closed triangles; the data for continuous delivery using implantable osmotic devices delivering 20 mcg/day of exenatide wherein subjects were subsequently switched in the extension phase to continuous delivery using implantable osmotic devices delivering 60 mcg/day of exenatide is presented as grey squares; and, the data for twice-daily injection of exenatide wherein subjects were switched in the extension phase to continuous delivery using implantable osmotic devices delivering 60 mcg/day of exenatide is presented as closed circles.

Figure 11:
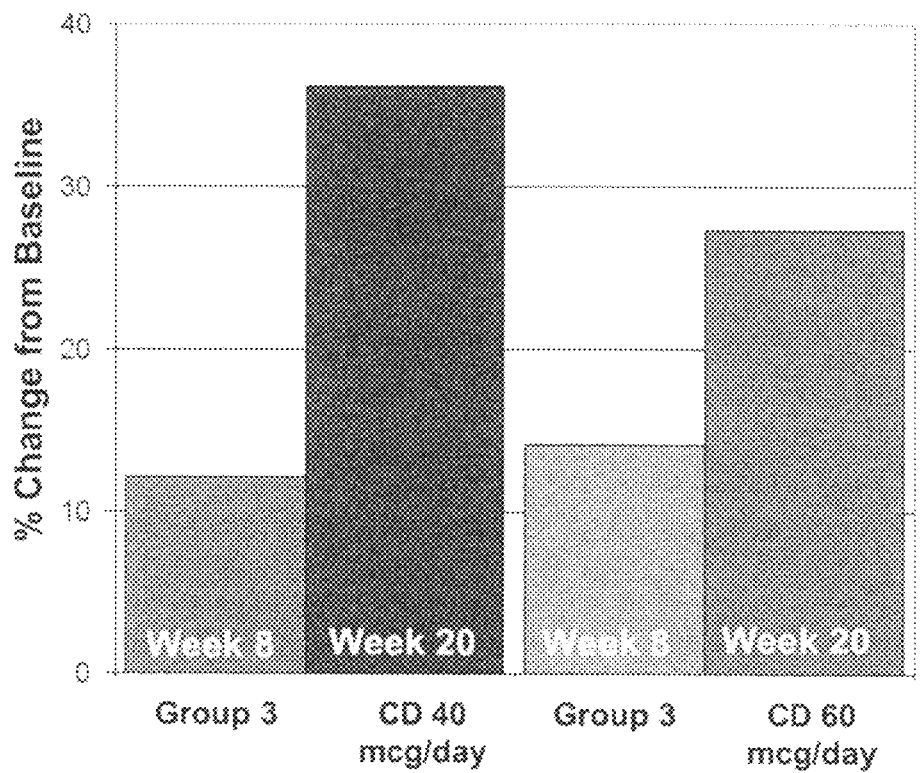

FIG. 11 presents extension phase data showing the percent change from baseline in overall QOL assessment at week 20. In the figure the numbers in each bar graph represent which week (week 8 or week 20) the QOL assessment was performed. The groups are arranged along the horizontal axis from the left as follows: Group 3 (at Week 8) switched to continuous delivery of exenatide at 40 mcg/day (CD 40 mcg/day); and Group 3 (at Week 8) switched to continuous delivery of exenatide at 60 mcg/day (CD 60 mcg/day). The vertical axis is the % Change from Baseline for the overall QOL score.

Figure 12:
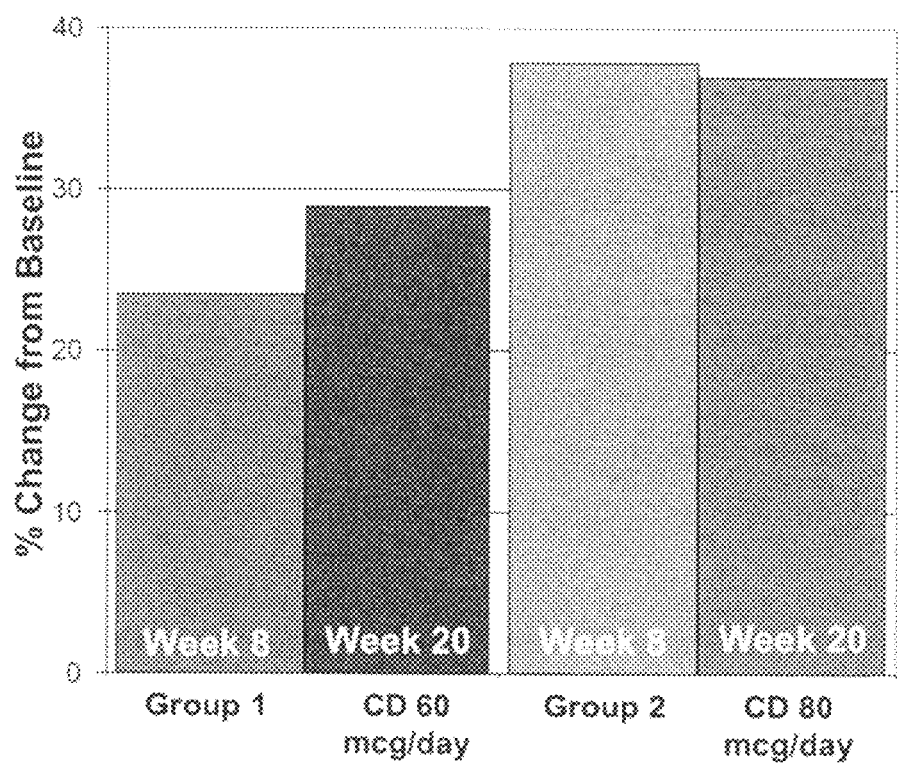

FIG. 12 presents further extension phase data showing the percent change from baseline in overall QOL assessment at week 20. In the figure the numbers in each bar graph represent which week (week 8 or week 20) the QOL assessment was performed. The groups are arranged along the horizontal axis from the left as follows: Group 1 (at Week 8) switched to continuous delivery of exenatide at 60 mcg/day (CD 60 mcg/day); and Group 2 (at Week 8) switched to continuous delivery of exenatide at 80 mcg/day (CD 80 mcg/day). The vertical axis is the % Change from Baseline for the overall QOL score.

FIG. 13 presents a competitive profile among subjects on metformin-only background treatment combined with a variety of type 2 diabetes mellitus treatments. The vertical axis is HbA1c %. The treatments are displayed on the horizontal axis, as follows: exenatide administered by twice-daily injection (Treatment A); exenatide administered by once-weekly injection (Treatment B); liraglutide administered by once-daily injection (Treatment C); taspoglutide administered by once-weekly injection (Treatment D); and treatment using the methods and osmotic delivery devices of the present invention for continuous delivery of exenatide at 20 mcg/day and 60 mcg/day (Treatment E). The number within and near the top of the solid bar graph associated with each treatment provides the baseline HbA1c % (e.g., Treatment A, 8.2). The number within and near the top of the stippled bar graph associated with each treatment provides the endpoint HbA1c % for the study (e.g., Treatment A, 7.4). The number within and near the horizontal axis of the stippled bar graph associated with each treatment provides the change of HbA1c for the study (e.g., Treatment A, −0.8).

FIG. 14 presents a competitive profile among subjects on metformin-only background treatment combined with a variety of type 2 diabetes mellitus treatments. The vertical axis is HbA1c %. The treatments are displayed on the horizontal axis, as follows: treatment using sitagliptin (Treatment F); and treatment using pioglitazone (Treatment G); exenatide administered by once-weekly injection (Treatment B); treatment using the methods and osmotic delivery devices of the present invention for continuous delivery of exenatide at 20 mcg/day and 60 mcg/day (Treatment E). The number within and near the top of the solid bar graph associated with each treatment provides the baseline HbA1c % (e.g., Treatment F, 8.5). The number within and near the top of the stippled bar graph associated with each treatment provides the endpoint HbA1c % for the study (e.g., Treatment F, 7.6). The number within and near the horizontal axis of the stippled bar graph associated with each treatment provides the change of HbA1c for the study (e.g., Treatment F, −0.9).

FIG. 15 presents a competitive profile among subjects on metformin-only background treatment combined either with continuous delivery of exenatide or with once-weekly injection of exenatide. The vertical axis is HbA1c %. The treatments are displayed toward the top of the figure, as follows: treatment using the methods and osmotic delivery devices of the present invention for continuous delivery of exenatide at 20 mcg/day and 60 mcg/day (Treatment E), which includes the first three sets of bar graphs; and treatment using exenatide administered by once-weekly injection (Treatment B), which is set off by a dotted-line box. On the horizontal axis, the subjects for Treatment E are broken down into groups based on baseline HbA1c as follows: All Subjects; Baseline HbA1c greater than 7.0; and Baseline HbA1c of greater than or equal to 7.5. The number within and near the top of the solid bar graph associated with each treatment provides the baseline HbA1c % (e.g., Treatment B, 8.6). The percent marked with an asterisk within the solid bar graph associated with each treatment provides the percentage of subjects who achieved an HbA1c of 7% or less (e.g., Treatment B, 58%*). The number within and near the top of the stippled bar graph associated with each treatment provides the endpoint HbA1c % for the study (e.g., Treatment B, 7.1). The number within and near the horizontal axis of the stippled bar graph associated with each treatment provides the change of HbA1c for the study (e.g., Treatment B, −1.5).

FIG. 16 presents a competitive profile among subjects on metformin-only background treatment combined either with continuous delivery of exenatide or with once-weekly injection of exenatide, wherein the baselines have been normalized. The vertical axis is HbA1c %. The treatments are displayed toward the top of the figure, as follows: treatment using exenatide administered by once-weekly injection (Treatment B); and treatment using the methods and osmotic delivery devices of the present invention for continuous delivery of exenatide at 20 mcg/day and 60 mcg/day (Treatment E). The figure is divided by a dark vertical line into two panels as follows: on the left side and labeled on the horizontal axis is data for subjects with a baseline HbA1c of less than 9.0; and on the right side and labeled on the horizontal axis is data for subjects with a baseline HbA1c of greater than or equal to 9.0. The asterisk following "Subjects with Baseline HbA1c≧9.0*" signifies that approximately one-third of subjects in Treatment B had baseline HbA1c of greater than or equal to 9.0; but only one subject of Treatment E had a baseline HbA1c of greater than or equal to 9.0. The number within and near the top of the solid bar graph associated with each treatment provides the baseline HbA1c % (e.g., Treatment B, left panel, 7.8). The number within and near the top of the stippled bar graph associated with each treatment provides the endpoint HbA1c % for the study (e.g., Treatment B, left panel, 6.7). The number within and near the horizontal axis of the stippled bar graph associated with each treatment provides the change of HbA1c for the study (e.g., Treatment B, left panel, −1.1).

Figure 17:
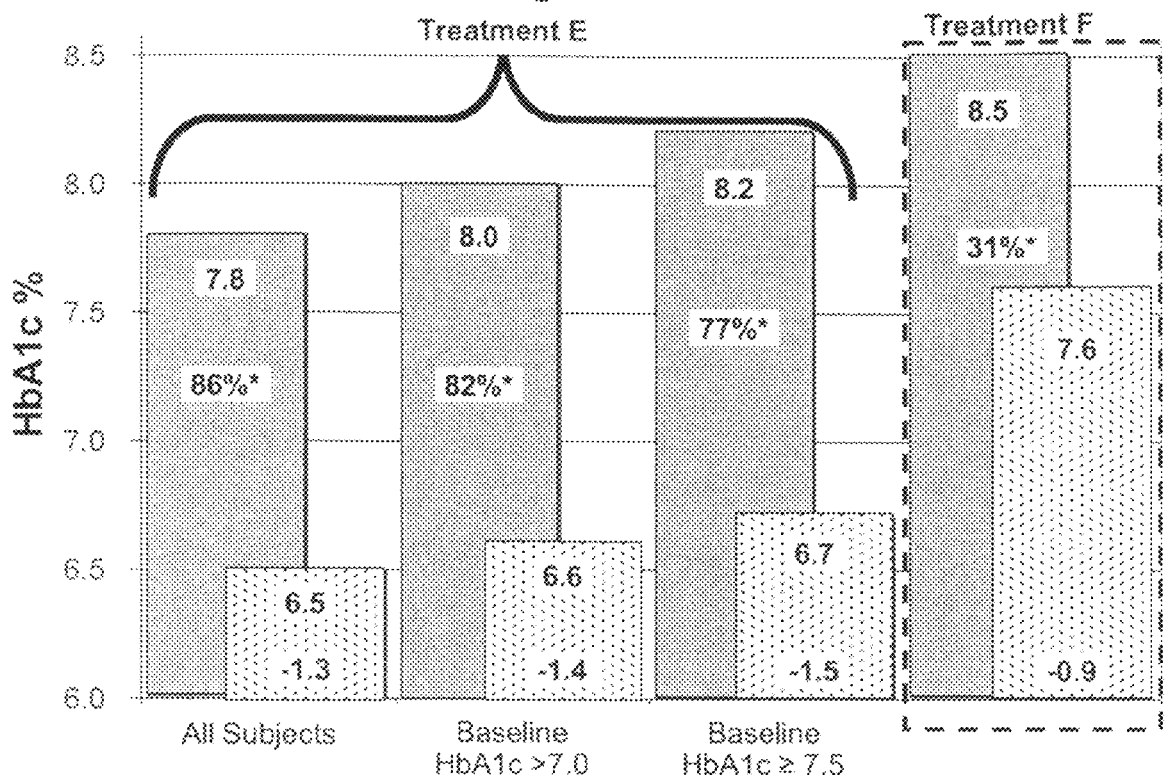

FIG. 17 presents a competitive profile among subjects on metformin-only background treatment combined either with continuous delivery of exenatide or with sitagliptin. The vertical axis is HbA1c %. The treatments are displayed toward the top of the figure, as follows: treatment using the methods and osmotic delivery devices of the present invention for continuous delivery of exenatide at 20 mcg/day and 60 mcg/day (Treatment E), which includes the first three sets of bar graphs; and treatment using sitagliptin (Treatment F), which is set off by a dotted-line box. On the horizontal axis, the subjects for Treatment E are broken down into groups based on baseline HbA1c as follows: All Subjects; Baseline HbA1c greater than 7.0; and Baseline HbA1c of greater than or equal to 7.5. The number within and near the top of the solid bar graph associated with each treatment provides the baseline HbA1c % (e.g., Treatment F, 8.5). The percent marked with an asterisk within the solid bar graph associated with each treatment provides the percentage of subjects who achieved an HbA1c of 7% or less (e.g., Treatment F, 31%*). The number within and near the top of the stippled bar graph associated with each treatment provides the endpoint HbA1c % for the study (e.g., Treatment F, 7.6). The number within and near the horizontal axis of the stippled bar graph associated with each treatment provides the change of HbA1c for the study (e.g., Treatment F, −0.9).

Figure 18:
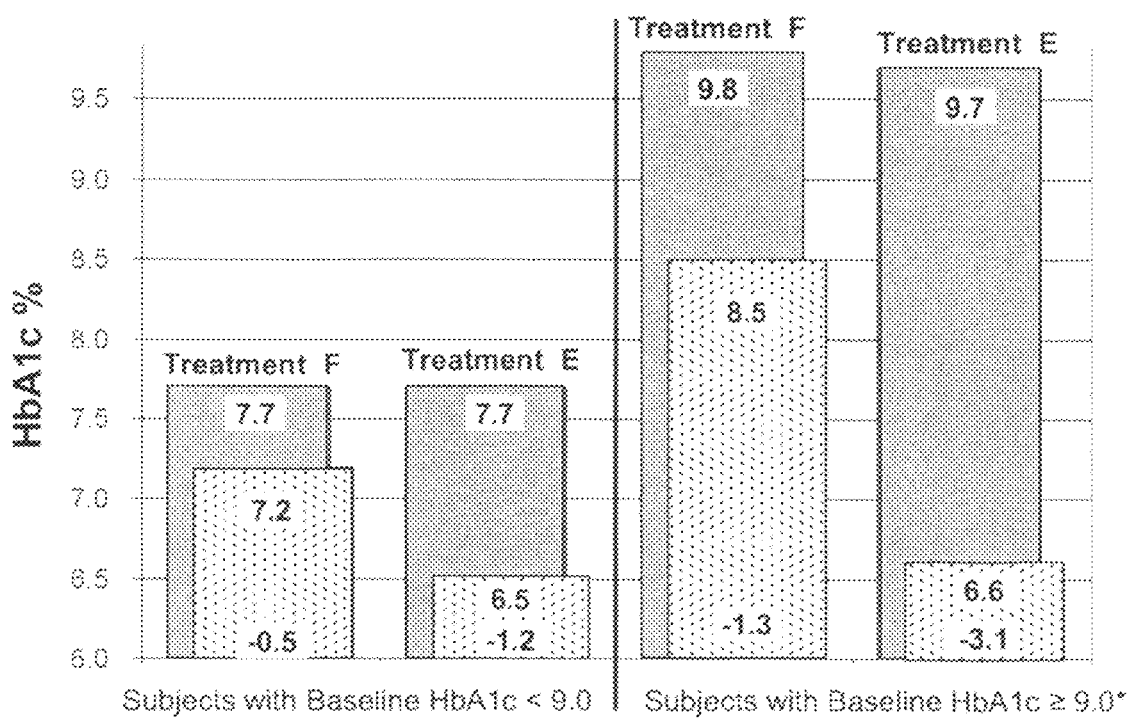

FIG. 18 presents a competitive profile among subjects on metformin-only background treatment combined either with continuous delivery of exenatide or with sitagliptin, wherein the baselines have been normalized. The vertical axis is HbA1c %. The treatments are displayed toward the top of the figure, as follows: treatment using sitagliptin (Treatment F); and treatment using the methods and osmotic delivery devices of the present invention for continuous delivery of exenatide at 20 mcg/day and 60 mcg/day (Treatment E). The figure is divided by a dark vertical line into two panels as follows: on the left side and labeled on the horizontal axis is data for subjects with a baseline HbA1c of less than 9.0; and on the right side and labeled on the horizontal axis is data for subjects with a baseline HbA1c of greater than or equal to 9.0. The asterisk following "Subjects with Baseline HbA1c≧9.0*" signifies that approximately one-third of subjects in Treatment F had baseline HbA1c of greater than or equal to 9.0; but only one subject of Treatment E had a baseline HbA1c of greater than or equal to 9.0. The number within and near the top of the solid bar graph associated with each treatment provides the baseline HbA1c % (e.g., Treatment F, left panel, 7.7). The number within and near the top of the stippled bar graph associated with each treatment provides the endpoint HbA1c % for the study (e.g., Treatment F, left panel, 7.2). The number within and near the horizontal axis of the stippled bar graph associated with each treatment provides the change of HbA1c for the study (e.g., Treatment F, left panel, −0.5).

Figure 19:
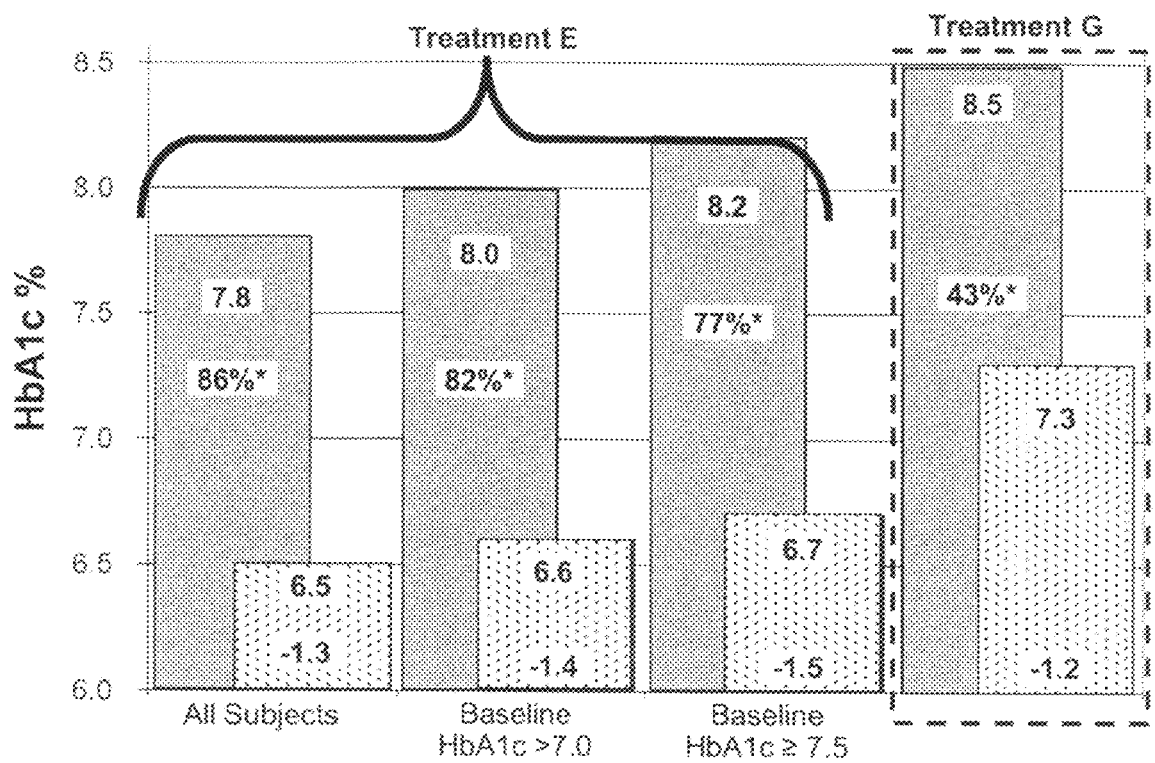

FIG. 19 presents a competitive profile among subjects on metformin-only background treatment combined either with continuous delivery of exenatide or with pioglitazone. The vertical axis is HbA1c %. The treatments are displayed toward the top of the figure, as follows: treatment using the methods and osmotic delivery devices of the present invention for continuous delivery of exenatide at 20 mcg/day and 60 mcg/day (Treatment E), which includes the first three sets of bar graphs; and treatment using pioglitazone (Treatment G), which is set off by a dotted-line box. On the horizontal axis, the subjects for Treatment E are broken down into groups based on baseline HbA1c as follows: All Subjects; Baseline HbA1c greater than 7.0; and Baseline HbA1c of greater than or equal to 7.5. The number within and near the top of the solid bar graph associated with each treatment provides the baseline HbA1c % (e.g., Treatment G, 8.5). The percent marked with an asterisk within the solid bar graph associated with each treatment provides the percentage of subjects who achieved an HbA1c of 7% or less (e.g., Treatment G, 43%*). The number within and near the top of the stippled bar graph associated with each treatment provides the endpoint HbA1c % for the study (e.g., Treatment G, 7.3). The number within and near the horizontal axis of the stippled bar graph associated with each treatment provides the change of HbA1c for the study (e.g., Treatment G, −1.2).

Figure 20:
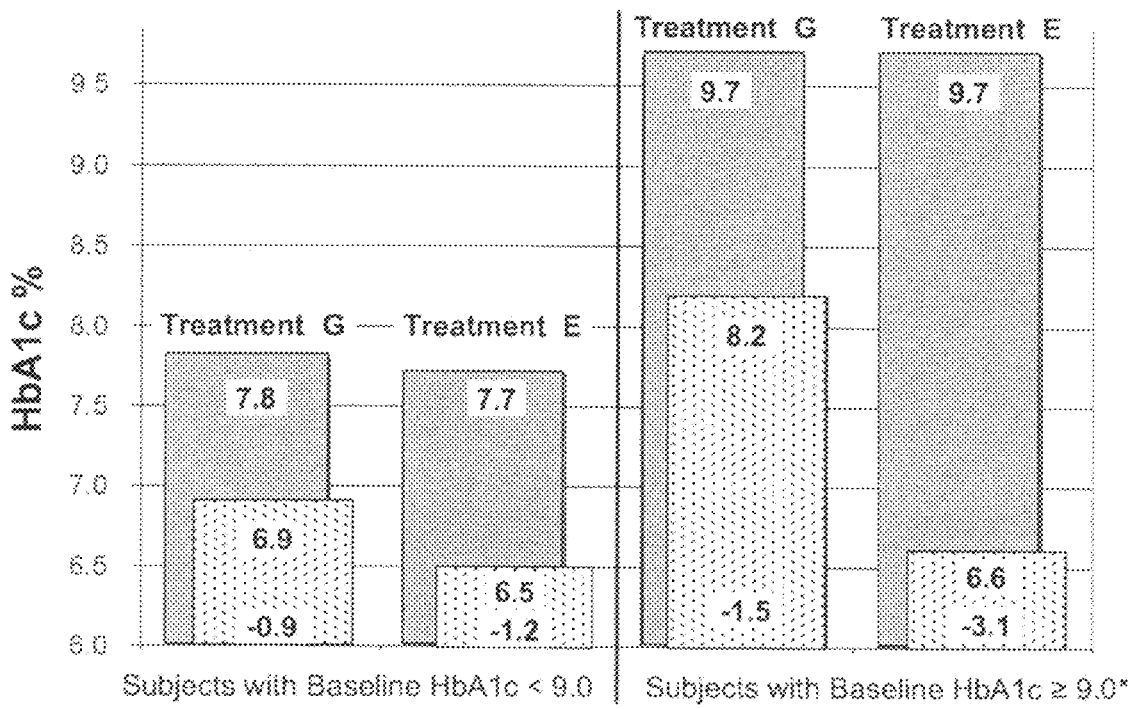

FIG. 20 presents a competitive profile among subjects on metformin-only background treatment combined either with continuous delivery of exenatide or with pioglitazone, wherein the baselines have been normalized. The vertical axis is HbA1c %. The treatments are displayed toward the top of the figure, as follows: treatment using pioglitazone (Treatment G); and treatment using the methods and osmotic delivery devices of the present invention for continuous delivery of exenatide at 20 mcg/day and 60 mcg/day (Treatment E). The figure is divided by a dark vertical line into two panels as follows: on the left side and labeled on the horizontal axis is data for subjects with a baseline HbA1c of less than 9.0; and on the right side and labeled on the horizontal axis is data for subjects with a baseline HbA1c of greater than or equal to 9.0. The asterisk following "Subjects with Baseline HbA1c≧9.0*" signifies that approximately one-third of subjects in Treatment G had baseline HbA1c of greater than or equal to 9.0; but only one subject of Treatment E had a baseline HbA1c of greater than or equal to 9.0. The number within and near the top of the solid bar graph associated with each treatment provides the baseline HbA1c % (e.g., Treatment G, left panel, 7.8). The number within and near the top of the stippled bar graph associated with each treatment provides the endpoint HbA1c % for the study (e.g., Treatment G, left panel, 6.9). The number within and near the horizontal axis of the stippled bar graph associated with each treatment provides the change of HbA1c for the study (e.g., Treatment G, left panel, −0.9).

FIG. 21 presents comparative weight loss data among subjects on metformin-only background treatment combined with a variety of type 2 diabetes mellitus treatments. The vertical axis is % Weight Loss. The treatments are displayed on the horizontal axis, as follows: treatment using pioglitazone (Treatment G); treatment using sitagliptin (Treatment F); exenatide administered by once-weekly injection (Treatment B); and treatment using the methods and osmotic delivery devices of the present invention for continuous delivery of exenatide at 20 mcg/day and 60 mcg/day (Treatment E). The number within the bar graph associated with each treatment provides the weight gain or loss for the study (e.g., Treatment G, +2.8 kg).

DETAILED DESCRIPTION OF THE INVENTION

All patents, publications, and patent applications cited in this specification are herein incorporated by reference as if each individual patent, publication, or patent application was specifically and individually indicated to be incorporated by reference in its entirety for all purposes.

1.0.0 Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a peptide" includes one or more peptides, or mixtures of peptides, reference to "a drug" includes one or more drugs, reference to "an osmotic device" includes one or more osmotic devices, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The terms "drug," "therapeutic agent," and "beneficial agent" are used interchangeably to refer to any therapeutically active substance that is delivered to a subject to produce a desired beneficial effect. In one embodiment of the present invention, the drug is a polypeptide. In another embodiment of the present invention, the drug is a small molecule, for example, hormones such as androgens or estrogens. The devices and methods of the present invention are well suited for the delivery of proteins, small molecules and combinations thereof.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogs, and/or amino acid mimetic). Peptides may be naturally occurring, synthetically produced, or recombinantly expressed. Peptides may also comprise additional groups modifying the amino acid chain, for example, functional groups added via post-translational modification. Examples of post-translation modifications include, but are not limited to, acetylation, alkylation (including, methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxy terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). The term peptide also includes modifications, such as but not limited to those described above, of amino acids falling between the amino and carboxy termini. In one embodiment, a peptide may be modified by addition of a small-molecule drug.

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

The phrase "amino acid residue" as used herein refers to an amino acid that is incorporated into a peptide by an amide bond or an amide bond mimetic.

The phrase "incretin mimetics" as used herein includes, but is not limited to, glucagon-like peptide 1 (GLP-1), as well as peptide derivatives and peptide analogs thereof; and exenatide, as well as peptide derivatives and peptide analogs thereof. Incretin mimetics are also known in the literature as "insulinotropic peptides" or "GLP-1 receptor agonists."

The term "insulinotropic" as used herein typically refers to the ability of a compound, e.g., a peptide, to stimulate or affect the production and/or activity of insulin (e.g., an insulinotropic hormone). Such compounds typically stimulate the secretion or biosynthesis of insulin in a subject.

The term "vehicle" as used herein refers to a medium used to carry a compound, e.g., a drug. Vehicles of the present invention typically comprise components such as polymers and solvents. The suspension vehicles of the present invention typically comprise solvents and polymers that are used to prepare suspension formulations further comprising drug particle formulations.

The phrase "phase separation" as used herein refers to the formation of multiple phases (e.g., liquid or gel phases) in the suspension vehicle, such as when the suspension vehicle contacts the aqueous environment. In some embodiments of the present invention, the suspension vehicle is formulated to exhibit phase separation upon contact with an aqueous environment having less than approximately 10% water.

The phrase "single-phase" as used herein refers to a solid, semisolid, or liquid homogeneous system that is physically and chemically uniform throughout.

The term "dispersed" as used herein refers to dissolving, dispersing, suspending, or otherwise distributing a compound, for example, a drug particle formulation, in a suspension vehicle.

The phrase "chemically stable" as used herein refers to formation in a formulation of an acceptable percentage of degradation products produced over a defined period of time by chemical pathways, such as deamidation (usually by hydrolysis), aggregation, or oxidation.

The phrase "physically stable" as used herein refers to formation in a formulation of an acceptable percentage of aggregates (e.g., dimers and other higher molecular weight products). Further, a physically stable formulation does not change its physical state as, for example, from liquid to solid, or from amorphous to crystal form.

The term "viscosity" as used herein typically refers to a value determined from the ratio of shear stress to shear rate (see, e.g., Considine, D. M. & Considine, G. D., Encyclopedia of Chemistry, 4th Edition, Van Nostrand, Reinhold, N.Y., 1984) essentially as follows:

$$F/A = \mu * V/L \qquad \text{(Equation 1)}$$

where F/A=shear stress (force per unit area),
μ=a proportionality constant (viscosity), and
V/L=the velocity per layer thickness (shear rate).

From this relationship, the ratio of shear stress to shear rate defines viscosity. Measurements of shear stress and shear rate are typically determined using parallel plate rheometery performed under selected conditions (for example, a temperature of about 37° C.). Other methods for the determination of viscosity include, measurement of a kinematic viscosity using viscometers, for example, a Cannon-Fenske viscometer, a Ubbelohde viscometer for the Cannon-Fenske opaque solution, or a Ostwald viscometer. Generally, suspension vehicles of the present invention have a viscosity sufficient to prevent a particle formulation suspended therein from settling during storage and use in a method of delivery, for example, in an implantable, drug delivery device.

The term "non-aqueous" as used herein refers to an overall moisture content, for example, of a suspension formulation, typically of less than or equal to about 10 wt %, preferably less than or equal to about 7 wt %, more preferably less than or equal to about 5 wt %, and more preferably less than about 4 wt %.

The term "subject" as used herein refers to any member of the subphylum Chordata, including, without limitation, humans and other primates, including non-human primates such as rhesus macaques and other monkey species and chimpanzees and other ape species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age or gender. Thus, both adult and newborn individuals are intended to be covered.

The term "osmotic delivery device" as used herein typically refers to a device used for delivery of a drug (e.g., an incretin mimetic) to a subject, wherein the device comprises, for example, a reservoir (made, e.g., from a titanium alloy) having a lumen that contains a suspension formulation comprising a drug (e.g., an incretin mimetic) and an osmotic agent formulation. A piston assembly positioned in the lumen isolates the suspension formulation from the osmotic agent formulation. A semi-permeable membrane is positioned at a first distal end of the reservoir adjacent the osmotic agent formulation and a diffusion moderator (which defines a delivery orifice through which the suspension formulation exits the device) is positioned at a second distal end of the reservoir adjacent the suspension formulation. Typically, the osmotic delivery device is implanted within the subject, for example, subcutaneously (e.g., in the inside, outside, or back of the upper arm; or in the abdominal area). An exemplary osmotic delivery device is the DUROS® (ALZA Corporation, Mountain View, Calif.) delivery device.

The term "continuous delivery" as used herein typically refers to a substantially continuous release of drug from an osmotic delivery device. For example, the DUROS® delivery device releases drug essentially at a predetermined rate based on the principle of osmosis. Extracellular fluid enters the DUROS® device through the semi-permeable membrane directly into the osmotic engine that expands to drive the piston at a slow and consistent rate of travel. Movement of the piston forces the drug formulation to be released through the orifice of the diffusion moderator. Thus release of the drug from the osmotic delivery device is at a slow, controlled, consistent rate.

The term "substantial steady-state delivery" as used herein typically refers to delivery of a drug at or near a target concentration over a defined period of time, wherein the amount of the drug being delivered from an osmotic device is substantially zero-order delivery. Substantial zero-order delivery of an active agent (e.g., exenatide) means that the rate of drug delivered is constant and is independent of the drug available in the delivery system; for example, for zero-order delivery, if the rate of drug delivered is graphed against time and a line is fitted to the data the line has a slope of approximately zero, as determined by standard methods (e.g., linear regression).

The phrase "drug half-life" as used herein refers how long it takes a drug to be eliminated from blood plasma by one half of its concentration. A drug's half-life is usually measured by monitoring how a drug degrades when it is administered via injection or intravenously. A drug is usually detected using, for example, a radioimmunoassay or chromatographic method.

2.0.0 General Overview of the Invention

Before describing the present invention in detail, it is to be understood that this invention is not limited to particular types of drug delivery devices, particular sources of drugs, particular solvents, particular polymers, and the like, as use of such particulars may be selected in view of the teachings of the present specification. It is also to be understood that the terminology used herein is for the purpose of describing particular embodiments of the invention only, and is not intended to be limiting.

In a first aspect, the present invention relates to a method of treating type 2 diabetes mellitus in a subject in need of treatment. The method comprises providing continuous delivery of an incretin mimetic from an osmotic delivery device, wherein substantial steady-state delivery of the incretin mimetic at a therapeutic concentration is achieved within a time period of about 7 days or less after implantation of the osmotic delivery device in the subject. The substantial steady-state delivery of the incretin mimetic from the osmotic delivery device is continuous over an administration period. Humans are preferred subjects for the practice of the present invention. The present invention includes an incretin mimetic (e.g., exenatide), as well as an osmotic device comprising an incretin mimetic (e.g., exenatide) for use in the present methods of treating type 2 diabetes mellitus in a subject in need of treatment.

In some embodiments of the present invention, the administration period is, for example, at least about 3 months, at least about 3 months to about a year, at least about 4 months to about a year, at least about 5 months to about a year, at least about 6 months to about a year, at least about 8 months to about a year, at least about 9 months to about a year, or at least about 10 months to about a year.

In some embodiments of the present invention, the substantial steady-state delivery of an incretin mimetic at therapeutic concentrations is achieved within about 5 days or less after implantation of the osmotic delivery device in the subject, within about 4 days or less after implantation of the osmotic delivery device in the subject, within about 3 days or less after implantation of the osmotic delivery device in the subject, within about 2 days or less after implantation of the osmotic delivery device in the subject, or within about 1 day or less after implantation of the osmotic delivery device in the subject. In preferred embodiments of the present invention, the substantial steady-state delivery of the incretin mimetic at therapeutic concentrations is achieved within about 2 days or less, more preferably within about 1 day or less after implantation of the osmotic delivery device in the subject.

In further embodiments, the treatment methods of the present invention provide significant decrease in the subject's fasting plasma glucose concentration after implantation of the osmotic delivery device in the subject (relative to the subject's fasting plasma glucose concentration before implantation of the osmotic delivery device) that is achieved within about 7 days or less after implantation of the osmotic delivery device in the subject, within about 6 days or less after implantation of the osmotic delivery device in the subject, within about 5 days or less after implantation of the osmotic delivery device in the subject, within about 4 days or less after implantation of the osmotic delivery device in the subject, within about 3 days or less after implantation of the osmotic delivery device in the subject, within about 2 days or less after implantation of the osmotic delivery device in the subject, or within about 1 day or less after implantation of the osmotic delivery device in the subject. In preferred embodiments of the present invention, the significant decrease in the subject's fasting plasma glucose concentration after implantation of the osmotic device, relative to the subject's fasting plasma glucose concentration before implantation, is achieved within about 2 days or less, preferably within about 1 day or less after implantation of the osmotic delivery device in the subject, or more preferably within about 1 day after implantation of the osmotic delivery device in the subject. The significant decrease in fasting plasma glucose is typically statistically significant as demonstrated by application of an appropriate statistical test or is considered significant for the subject by a medical practitioner. A significant decrease in fasting plasma glucose relative to the baseline before implantation is typically maintained over the administration period.

In yet further embodiments of the first aspect of the present invention, the treatment methods further comprise the capability to terminate the continuous delivery of the incretin mimetic such that the concentration of the incretin mimetic is substantially undetectable in a blood sample from the subject within about 6 half-lives or less of the incretin mimetic after termination of continuous delivery, within about 5 half-lives or less of the incretin mimetic after termination of continuous delivery, within about 4 half-lives or less of the incretin mimetic after termination of continuous delivery, or within about 3 half-lives or less of the incretin mimetic after termination of continuous delivery. Examples of incretin mimetic half-lives are exenatide, approximately 2.5 hours, and GLP-1, approximately 2 minutes. The incretin mimetic may be detected, for example, by a radioimmunoassay. Termination of the continuous delivery can be accomplished, for example, by removal of the osmotic delivery device from the subject.

In related embodiments of the present invention, the treatment methods further comprise the capability to terminate the continuous delivery of exenatide such that the concentration of exenatide is substantially undetectable in a blood sample from the subject in less than about 72 hours after termination of continuous delivery, in less than about 48 hours after termination of continuous delivery, in less than about 24 hours after termination of continuous delivery, in less than about 18 hours after termination of continuous delivery, in less than about 14 hours after termination of continuous delivery, in less than about 12 hours after termination of continuous delivery, in less than about 6 hours after termination of continuous delivery, or in less than about 4 hours after termination of continuous delivery. In preferred embodiments, exenatide is substantially undetectable in a blood sample from the subject in less than about 24 hours after termination of continuous delivery, in less than about 18 hours after termination of continuous delivery, or more preferably in less than about 14 hours after termination of continuous delivery.

In preferred embodiments of the first aspect of the present invention, the incretin mimetic comprises an exenatide peptide, a peptide analog thereof, or a peptide derivative thereof; a GLP-1 peptide (e.g., GLP-1(7-36)amide peptide), a peptide analog thereof, or a peptide derivative thereof. Specific examples of preferred incretin mimetics useful in the practice of the present invention include exenatide having the amino acid sequence of exendin-4, lixisenatide, GLP-1(7-36), liraglutide, albiglutide, and taspoglutide.

In some embodiments of the first aspect of the present invention, wherein the incretin mimetic is exenatide, the continuous delivery can provide to the subject a mcg/day dose of exenatide, for example, of about 10 mcg/day, about 20 mcg/day, about 30 mcg/day, about 40 mcg/day, about 60 mcg/day, or about 80 mcg/day.

In some embodiments of the first aspect of the present invention, wherein the incretin mimetic is exenatide, the method of treating type 2 diabetes mellitus further comprises the capability to terminate the continuous delivery such that the concentration of the exenatide is substantially undetectable in a blood sample from the subject after termination of continuous delivery, for example, in less than about 72 hours, in less than about 48 hours, in less than about 24, or in less than about 12 hours.

In additional embodiments of the first aspect of the present invention, the method of treating type 2 diabetes mellitus further comprises a first continuous administration period of the incretin mimetic at a first mcg/day dose that is followed by a second continuous administration period providing a dose escalation of the incretin mimetic to a second mcg/day dose, wherein the second mcg/day dose is greater than the first mcg/day dose. In some embodiments, the first mcg/day dose is delivered by a first osmotic delivery device and the second mcg/day dose is delivered by a second osmotic delivery device, and delivery of the incretin mimetic from at least the first or the second osmotic delivery device is continuous over the administration period of at least about 3 months. In one embodiment, the second mcg/day dose is at least two times greater than the first mcg/day dose. Further, the method can comprise at least one more continuous administration period providing a dose escalation of the incretin mimetic to a higher mcg/day dose relative to the second mcg/day dose. Dose escalation can be accomplished, for example, by removal of the first osmotic delivery device and implantation of a second osmotic delivery device, or by implantation of a second or further osmotic delivery device where the total dose delivered by the first and second osmotic delivery devices results in the desired dose escalation.

In a preferred embodiment of the present invention comprising dose escalation, the incretin mimetic is an exenatide, and the first mcg/day dose followed by the second mcg/day dose for continuous delivery are selected from the group consisting of: about 10 mcg/day followed by about 20 mcg/day; about 10 mcg/day followed by about 40 mcg/day; about 10 mcg/day followed by about 60 mcg/day; about 10 mcg/day followed by about 80 mcg/day; about 20 mcg/day followed by about 40 mcg/day; about 20 mcg/day followed by about 60 mcg/day; about 20 mcg/day followed by about 80 mcg/day; about 40 mcg/day followed by about 60 mcg/day; about 40 mcg/day followed by about 80 mcg/day; and about 60 mcg/day followed by about 80 mcg/day.

In a second aspect, the present invention relates to a method of treating type 2 diabetes mellitus in a subject in need of treatment. The method comprises providing continuous delivery of an incretin mimetic (e.g., exenatide) from an implanted osmotic delivery device, wherein (i) a significant decrease in fasting plasma glucose concentration is achieved after implantation of the osmotic device in the subject, relative to the fasting plasma glucose concentration before implantation, within about 7 days of implantation of the osmotic delivery device in the subject, (ii) the delivery of the incretin mimetic is continuous over an administration period, and (iii) a significant decrease in fasting plasma glucose is maintained over the period. The significant decrease in fasting plasma glucose is typically statistically significant as demonstrated by application of an appropriate statistical test or is considered significant for the subject by a medical practitioner.

In a third aspect, the present invention relates to a method of treating type 2 diabetes mellitus in a subject in need of treatment comprising the capability to terminate continuous delivery of an incretin mimetic such that the concentration of the incretin mimetic is substantially undetectable in a blood sample from the subject within about 6 half-lives or less of the incretin mimetic after termination of continuous delivery, within about 5 half-lives or less of the incretin mimetic after termination of continuous delivery, within about 4 half-lives or less of the incretin mimetic after termination of continuous delivery, or within about 3 half-lives or less of the incretin mimetic after termination of continuous delivery. Examples of incretin mimetic half-lives include exenatide, approximately 2.5 hours, and GLP-1, approximately 2 minutes.

In a fourth aspect, the present invention relates to a method of treating type 2 diabetes mellitus, comprising a first continuous administration period of an incretin mimetic at a first mcg/day dose that is followed by a second continuous administration period providing a dose escalation of the incretin mimetic to a second mcg/day dose, wherein the second mcg/day dose is greater than the first mcg/day dose. In some embodiments, the first mcg/day dose is delivered by a first osmotic delivery device and the second mcg/day dose is delivered by a second osmotic delivery device, and delivery of the incretin mimetic from at least the first or the second osmotic delivery device is continuous over the administration period of at least about 3 months. In one embodiment, the second mcg/day dose is at least two times greater than the first mcg/day dose. Further, the method can comprise at least one additional continuous administration period providing a dose escalation of the incretin mimetic to a higher mcg/day dose relative to the second mcg/day dose. Dose escalation can be accomplished, for example, by removal of the first osmotic delivery device and implantation of a second osmotic delivery device, or by implantation of a second or further osmotic delivery device where the total dose delivered by the first and second (or further) osmotic delivery devices results in the desired dose escalation. This aspect of the present invention (which comprises multiple, sequential continuous administration periods of escalating doses of the incretin mimetic) provides improved tolerization to dose escalation of the incretin mimetic relative to dose escalation based on injection of the incretin mimetic.

In embodiments of all aspects of the present invention relating to methods of treating type 2 diabetes mellitus, an exemplary osmotic delivery device comprises the following: an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a suspension formulation, wherein the second chamber comprises the suspension formulation and the suspension formulation is flowable and comprises the incretin mimetic; and a diffusion moderator inserted in the second open end of the reservoir, the diffusion moderator adjacent the suspension formulation. In preferred embodiments, the reservoir comprises titanium or a titanium alloy.

In embodiments of all aspects of the present invention relating to methods of treating type 2 diabetes mellitus, suspension formulations for use in the methods can, for example, comprise a particle formulation comprising an incretin mimetic, and a vehicle formulation. Examples of incretin mimetics include, but are not limited to, an exenatide peptide, a peptide analog thereof, or a peptide derivative thereof; a GLP-1 peptide, a peptide analog thereof, or a peptide derivative thereof. Specific examples of preferred incretin mimetics include exenatide having the amino acid sequence of exendin-4, lixisenatide, GLP-1(7-36), liraglutide, albiglutide, and taspoglutide. Vehicle formulations for use in forming the suspension formulations of the present invention can, for example, comprise a solvent and a polymer. Examples of solvents include, but are not limited to benzyl benzoate, lauryl lactate, lauryl alcohol, or combinations thereof. An example of a polymer is a polyvinvylpyrrolidone. In a preferred embodiment, the suspension vehicle consists essentially of one solvent and one polymer, for example, the solvent benzyl benzoate and the polymer polyvinvylpyrrolidone.

The reservoir of the osmotic delivery devices may, for example, comprise titanium or a titanium alloy.

In a fifth aspect, the present invention relates to a method of treating a disease or condition in a subject in need of treatment. The method comprises providing continuous delivery of a drug from an osmotic delivery device, wherein substantial steady-state delivery of the drug at therapeutic concentrations is achieved within a time period of about 7 days or less after implantation of the osmotic delivery device in the subject. The substantial steady-state delivery of the drug from the osmotic delivery device is continuous over an administration period of at least about 3 months. The drug has a known or determined half-life in a typical subject. Humans are preferred subjects for the practice of the present invention. The present invention includes a drug effective for treatment of the disease or condition, as well as an osmotic device comprising the drug for use in the present methods of treating the disease or condition in a subject in need of treatment. Advantages of the present invention include mitigation of peak-associated drug toxicities and attenuation of sub-optimal drug therapy associated with troughs.

In some embodiments of the present invention, the administration period is, for example, at least about 3 months, at least about 3 months to about a year, at least about 4 months to about a year, at least about 5 months to about a year, at least about 6 months to about a year, at least about 8 months to about a year, at least about 9 months to about a year, or at least about 10 months to about a year.

In one embodiment of this aspect of the present invention, the method of treating a disease or condition includes the proviso that the disease or condition is not prostate cancer.

In some embodiments of this aspect of the present invention, the substantial steady-state delivery of a drug at therapeutic concentrations is achieved within a period of about 7 days or less after implantation of the osmotic delivery device in the subject, about 5 days or less after implantation of the osmotic delivery device in the subject, about 4 days or less after implantation of the osmotic delivery device in the subject, about 3 days or less after implantation of the osmotic delivery device in the subject, about 2 days or less after implantation of the osmotic delivery device in the subject, or about 1 day or less after implantation of the osmotic delivery device in the subject.

In some embodiments of this aspect of the present invention, establishment of the substantial steady-state delivery of the drug at therapeutic concentrations, after implantation of the osmotic delivery device in the subject, may take a longer period of time, for example, a period of about 2 weeks or less, or within less than about 6 half-lives of the drug within the subject after implantation of the device.

In yet further embodiments of the fifth aspect of the present invention, the methods of treating a disease or condition further comprise the capability to terminate the continuous delivery of the drug such that the concentration of the drug is substantially undetectable in a blood sample from the subject within about 6 half-lives or less of the drug after termination of continuous delivery, within about 5 half-lives or less of the drug after termination of continuous delivery, within about 4 half-lives or less after termination of continuous delivery, or within about 3 half-lives or less of the drug after termination of continuous delivery. Some examples of drug half-lives are as follows: exenatide, approximately 2.5 hours; GLP-1, approximately 2 minutes; GIP, approximately 5 minutes; PYY, approximately 8 minutes; glucagon, approximately 6 minutes; oxynotomodulin, approximately 6 minutes; and GLP-2, approximately 6 minutes. In the situation where more than one drug is administered, the capability to terminate the continuous delivery of the more than one drug is such that the concentration of the more than one drug is substantially undetectable in a blood sample from the subject within about 6 half-lives or less of the more than one drug having the longest half-life after termination of continuous delivery. Termination of the continuous delivery can be accomplished, for example, by removal of the osmotic delivery device from the subject. In some embodiments, the drug is detected in a blood sample by a radioimmunoassay or chromatography.

In preferred embodiments of the fifth aspect of the present invention, the drug comprises a polypeptide, for example, selected from the following: recombinant antibodies, antibody fragments, humanized antibodies, single chain antibodies, monoclonal antibodies, and avimers; human growth hormone, epidermal growth factor, fibroblast growth factor, platelet-derived growth factor, transforming growth factor, and nerve growth factor; cytokines; and interferons. In other embodiments, the drug comprises a small molecule.

In additional embodiments of the fifth aspect of the present invention, the method of treating a disease or condition further comprises a first continuous administration period of the drug at a first dose/day that is followed by a second continuous administration period providing a dose escalation of the drug to a second dose/day, wherein the second dose/day is greater than the first dose/day. In some embodiments, the first dose/day is delivered by a first osmotic delivery device and the second dose/day is delivered by a second osmotic delivery device, and delivery of the drug from at least the first or the second osmotic delivery device is continuous over the administration period of at least about 3 months. In one embodiment, the second dose/day is at least two times greater than the first dose/day. Further, the method can comprise at least one more continuous administration period providing a dose escalation of the drug to a higher dose/day relative to the second dose/day. Dose escalation can be accomplished, for example, by removal of the first osmotic delivery device and implantation of a second osmotic delivery device, or by implantation of a second or further osmotic delivery device where the total dose delivered by the first and second osmotic delivery devices results in the desired dose escalation.

In a sixth aspect, the present invention relates to a method of treating a disease or condition in a subject in need of treatment comprising the capability to terminate continuous delivery of a drug such that the concentration of the drug is substantially undetectable in a blood sample from the subject within about 6 half-lives or less of the drug after termination of continuous delivery, within about 5 half-lives or less of the drug after termination of continuous delivery, within about 4 half-lives or less of the drug after termination of continuous delivery, or within about 3 half-lives or less of the drug after termination of continuous delivery. Some examples of drug half-lives are as follows: exenatide, approximately 2.5 hours; GLP-1, approximately 2 minutes; GIP, approximately 5 minutes; PYY, approximately 8 minutes; glucagon, approximately 6 minutes; oxyntomodulin, approximately 6 minutes; and GLP-2, approximately 6 minutes. In some embodiments, termination of continuous delivery comprises removal of the osmotic delivery device from the subject. In some embodiments, the drug is detected in a blood sample by a radioimmunoassay or chromatography.

In a seventh aspect, the present invention relates to a method of treating a disease or condition in a subject in need of treatment, comprising a first continuous administration period of a drug at a first dose/day that is followed by a second continuous administration period providing a dose escalation of the drug to a second dose/day, wherein the second dose/day is greater than the first dose/day. In some embodiments, the first dose/day is delivered by a first osmotic delivery device and the second dose/day is delivered by a second osmotic delivery device, and delivery of the drug from at least the first or the second osmotic delivery device is continuous over the administration period of at least about 3 months. In one embodiment, the second dose/day is at least two times greater than the first dose/day. Further, the method can comprise at least one additional continuous administration period providing a dose escalation of the drug to a higher dose/day relative to the second dose/day. Dose escalation can be accomplished, for example, by removal of the first osmotic delivery device and implantation of a second osmotic delivery device, or by implantation of a second or further osmotic delivery device where the total dose delivered by the first and second (or further) osmotic delivery devices results in the desired dose escalation. This aspect of the present invention (which comprises multiple, sequential continuous administration periods of escalating doses of the drug) provides improved tolerization to dose escalation of the drug relative to, for example, dose escalation based on injection of the drug.

In embodiments of all aspects of the present invention relating to methods of treating a disease or condition in a subject, an exemplary osmotic delivery device comprises the following: an impermeable reservoir comprising interior and exterior surfaces and first and second open ends; a semi-permeable membrane in sealing relationship with the first open end of the reservoir; an osmotic engine within the reservoir and adjacent the semi-permeable membrane; a piston adjacent the osmotic engine, wherein the piston forms a movable seal with the interior surface of the reservoir, the piston divides the reservoir into a first chamber and a second chamber, the first chamber comprising the osmotic engine; a drug formulation or suspension formulation comprising the drug, wherein the second chamber comprises the drug formulation or suspension formulation and the drug formulation or suspension formulation is flowable; and a diffusion moderator inserted in the second open end of the reservoir, the diffusion moderator adjacent the suspension formulation. In preferred embodiments, the reservoir comprises titanium or a titanium alloy.

In embodiments of all aspects of the present invention relating to methods of treating a disease or condition in a subject, the drug formulation can comprise the drug and a vehicle formulation. Alternatively, suspension formulations are used in the methods and can, for example, comprise a particle formulation comprising the drug and a vehicle formulation. Vehicle formulations for use in forming the suspension formulations of the present invention can, for example, comprise a solvent and a polymer. Examples of solvents include, but are not limited to benzyl benzoate, lauryl lactate, lauryl alcohol, or combinations thereof. An example of a polymer is a polyvinvylpyrrolidone. In a preferred embodiment, the suspension vehicle consists essentially of one solvent and one polymer, for example, the solvent benzyl benzoate and the polymer polyvinvylpyrrolidone.

The reservoir of the osmotic delivery devices may, for example, comprise titanium or a titanium alloy.

In embodiments of all aspects of the present invention the implanted osmotic delivery device can be used to provide subcutaneous delivery.

In embodiments of all aspects of the present invention the continuous delivery can, for example, be zero-order, controlled continuous delivery.

3.0.0 Formulations and Compositions

Drugs for use in the practice of the present invention are typically uniformly suspended, dissolved or dispersed in a suspension vehicle to form a suspension formulation.

3.1.0 Drug Particle Formulations

In one aspect, the present invention provides drug particle formulations for pharmaceutical use. The particle formulation typically comprises a drug and includes one or more stabilizing component. Examples of stabilizing components include, but are not limited to, carbohydrates, antioxidants, amino acids, buffers, inorganic compounds, and surfactants.

3.1.1 Exemplary Drugs

The drug particle formulations comprise a drug. The drug may be any physiologically or pharmacologically active substance, particularly those known to be delivered to the body of a human or an animal. Drugs that may be delivered by the osmotic delivery system of the present invention include, but are not limited to, drugs that act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system or the central nervous system. Further, drugs that may be delivered by the osmotic delivery system of the present invention include, but are not limited to, drugs used for the treatment of infectious diseases, chronic pain, diabetes, autoimmune disorders, endocrine disorders, metabolic disorders, and rheumatologic disorders.

Suitable drugs include, but are not limited to, the following: peptides, proteins, polypeptides (e.g., enzymes, hormones, cytokines), polynucleotides, nucleoproteins, polysaccharides, glycoproteins, lipoproteins, steroids, analgesics, local anesthetics, antibiotic agents, anti-inflammatory corticosteroids, ocular drugs, other small molecules for pharmaceutical use (e.g., ribavirin), or synthetic analogs of these species, as well as mixtures thereof.

In one embodiment, preferred drugs include macromolecules. Such macromolecules include, but are not limited to, pharmacologically active peptides proteins, polypeptides, genes, gene products, other gene therapy agents, or other small molecules. In a preferred embodiment the macromolecules are peptides, polypeptides or proteins. Numerous peptides, proteins, or polypeptides that are useful in the practice of the present invention are described herein. In addition to the peptides, proteins, or polypeptides described, modifications of these peptides, proteins, or polypeptides are also known to one of skill in the art and can be used in the practice of the present invention following the guidance presented herein. Such modifications include, but are not limited to, amino acid analogs, amino acid mimetics, analog polypeptides, or derivative polypeptides. Further, the drugs disclosed herein may be formulated or administered singly or in combination (e.g., using mixtures of drugs or multiple devices; U.S. Patent Publication No. 2009/0202608).

Examples of proteins that can be formulated into drug particle formulations of the present invention include, but are not limited to, the following: human growth hormone; somatostatin; somatropin, somatotropin, somatotropin analogs, somatomedin-C, somatotropin plus an amino acid, somatotropin plus a protein; follicle stimulating hormone; luteinizing hormone, luteinizing hormone-releasing hormone (LHRH), LHRH analogs such as leuprolide or leuprolide acetate, nafarelin and goserelin, LHRH agonists or antagonists; growth hormone releasing factor; calcitonin; colchicine; gonadotropic releasing hormone; gonadotropins such as chorionic gonadotropin; oxytocin, octreotide; vasopressin; adrenocorticotrophic hormone; epidermal growth factor; fibroblast growth factor; platelet-derived growth factor; transforming growth factor; nerve growth factor; prolactin; cosyntropin; lypressin polypeptides such as thyrotropin releasing hormone; thyroid stimulation hormone; secretin; pancreozymin; enkephalin; glucagon; incretin mimetics; endocrine agents secreted internally and distributed by way of the bloodstream; or the like.

Further proteins that may be formulated into drug particle formulations include, but are not limited to, the following: alpha antitrypsin; factor VII; factor VIII; factor IX and other coagulation factors; insulin and insulin related compounds (for example, isophane insulin suspension, protamine zinc insulin suspension, globin zinc insulin, extended insulin zinc suspension); peptide hormones; adrenal cortical stimulating hormone, thyroid stimulating hormone and other pituitary hormones; erythropoietin; growth factors such as granulocyte-colony stimulating factor, granulocyte-macrophage colony stimulating factor, insulin-like growth factor 1; tissue plasminogen activator; CD4; 1-deamino-8-D-arginine vasopressin; interleukin-1 receptor antagonist; tumor necrosis factor, tumor necrosis factor receptor; tumor suppressor proteins; pancreatic enzymes; lactase; cytokines, including lymphokines, chemokines or interleukins such as interleukin-1, interleukin-2; cytotoxic proteins; superoxide dismutase; endocrine agents secreted internally and distributed in an animal by way of the bloodstream; recombinant antibodies, antibody fragments, humanized antibodies, single chain antibodies, monoclonal antibodies; avimers; or the like.

Some embodiments of the present invention comprise use of peptide hormones, for example, incretin mimetics (e.g., GLP-1 or exenatide), as well as peptide analogs and peptide derivatives thereof; PYY (also known as peptide YY, peptide tyrosine tyrosine), as well as peptide analogs and peptide derivatives thereof, for example, PYY(3-36); oxyntomodulin, as well as peptide analogs and peptide derivatives thereof); and gastric inhibitory peptide (GIP), as well as peptide analogs and peptide derivatives thereof.

Other embodiments comprise use of interferon peptides (e.g., alpha, beta, gamma, lambda, omega, tau, consensus, and variant interferons, as well as peptide analogs or peptide derivatives thereof such as pegylated forms, as well as mixtures thereof; see, for example, The Interferons: Characterization and Application, by Anthony Meager (Editor), Wiley-VCH (May 1, 2006)).

GLP-1, including three forms of the peptide, GLP-1(1-37), GLP-1(7-37) and GLP-1(7-36)amide, as well as peptide analogs of GLP-1 have been shown to stimulate insulin secretion (i.e., is insulinotropic), which induces glucose uptake by cells and results in decreases in serum glucose concentrations (see, e.g., Mojsov, S., Int. J. Peptide Protein Research, 40:333-343 (1992)).

Numerous GLP-1 peptide derivatives and peptide analogs demonstrating insulinotropic action are known in the art (see, e.g., U.S. Pat. Nos. 5,118,666; 5,120,712; 5,512,549; 5,545,618; 5,574,008; 5,574,008; 5,614,492; 5,958,909; 6,191,102; 6,268,343; 6,329,336; 6,451,974; 6,458,924; 6,514,500; 6,593,295; 6,703,359; 6,706,689; 6,720,407; 6,821,949; 6,849,708; 6,849,714; 6,887,470; 6,887,849; 6,903,186; 7,022,674; 7,041,646; 7,084,243; 7,101,843; 7,138,486; 7,141,547; 7,144,863; and 7,199,217), as well as in clinical trials (e.g., taspoglutide and albiglutide). One example of a GLP-1 peptide derivative useful in the practice of the present invention is Victoza® (Novo Nordisk A/S, Bagsvaerd D K) (liraglutide; U.S. Pat. Nos. 6,268,343, 6,458,924, 7,235,627). Once-daily injectable Victoza® (liraglutide) is commercially available in the United States, Europe, and Japan. For ease of reference herein, the family of GLP-1 peptides, GLP-1 peptide derivatives and GLP-1 peptide analogs having insulinotropic activity is referred to collectively as "GLP-1."

The molecule exenatide has the amino acid sequence of exendin-4 (Kolterman O. G., et al., J. Clin. Endocrinol. Metab. 88(7):3082-9 (2003)) and is produced by chemical synthesis or recombinant expression. Twice-daily injectable exenatide is commercially available in the United States and Europe, and sold under the tradename of Byetta® (Amylin Pharmaceuticals, Inc., San Diego, Calif.). Exendin-3 and exendin-4 are known in the art and were originally isolated from *Heloderma* spp. (Eng, J., et al., J. Biol. Chem., 265: 20259-62 (1990); Eng., J., et al., J. Biol. Chem., 267:7402-05 (1992)). Use of exendin-3 and exendin-4 for the treatment of type 2 diabetes mellitus and the prevention of hyperglycemia has been proposed (see, e.g., U.S. Pat. No. 5,424,286). Numerous exenatide peptide derivatives and peptide analogs (including, e.g., exendin-4 agonists) are known in the art (see, e.g., U.S. Pat. Nos. 5,424,286; 6,268,343; 6,329,336; 6,506, 724; 6,514,500; 6,528,486; 6,593,295; 6,703,359; 6,706,689; 6,767,887; 6,821,949; 6,849,714; 6,858,576; 6,872,700; 6,887,470; 6,887,849; 6,924,264; 6,956,026; 6,989,366; 7,022,674; 7,041,646; 7,115,569; 7,138,375; 7,141,547; 7,153,825; and 7,157,555). One example of an exenatide derivative useful in the practice of the present invention is lixisenatide (also known as ZP10, AVE0010) (see, e.g., U.S. Pat. No. 6,528,486), which is in clinical trials. For ease of reference herein, the family of exenatide peptides (e.g., including exendin-3, exendin-4, and exendin-4-amide), exenatide peptide derivatives, and exenatide peptide analogs is referred to collectively as "exenatide."

PYY is a 36 amino acid residue peptide amide. PYY inhibits gut motility and blood flow (Laburthe, M., Trends Endocrinol Metab. 1(3):168-74 (1990), mediates intestinal secretion (Cox, H. M., et al., Br J Pharmacol 101(2):247-52 (1990); Playford, R. J., et al., Lancet 335(8705):1555-7 (1990)), and stimulate net absorption (MacFayden, R. J., et al., Neuropeptides 7(3):219-27 (1986)). Two major in vivo variants, PYY (1-36) and PYY(3-36), have been identified (e.g., Eberlein, G. A., et al., Peptides 10(4), 797-803 (1989)). The sequence of PYY, as well as peptide analogs and peptide derivatives thereof, are known in the art (e.g., U.S. Pat. Nos. 5,574,010 and 5,552,520).

Oxyntomodulin is a naturally occurring 37 amino acid peptide hormone found in the colon that has been found to suppress appetite and facilitate weight loss (Wynne K, et al., Int J Obes (Lond) 30(12):1729-36(2006)). The sequence of oxyntomodulin, as well as peptide analogs and peptide derivatives thereof, are known in the art (e.g., Bataille D, et al., Peptides 2(Suppl 2):41-44 (1981); and U.S. Patent Publication Nos. 2005/0070469 and 2006/0094652).

GIP is an insulinotropic peptide hormone (Efendic, S., et al., Horm Metab Res. 36:742-6 (2004)) and is secreted by the mucosa of the duodenum and jejunum in response to absorbed fat and carbohydrate that stimulate the pancreas to secrete insulin. GIP circulates as a biologically active 42-amino acid peptide. GIP is also known as glucose-dependent insulinotropic protein. GIP is a 42-amino acid gastrointestinal regulatory peptide that stimulates insulin secretion from pancreatic beta cells in the presence of glucose (Tseng, C., et al., PNAS 90:1992-1996 (1993)). The sequence of GIP, as well as peptide analogs and peptide derivatives thereof, are known in the art (e.g., Meier J. J., Diabetes Metab Res Rev. 21(2):91-117 (2005); Efendic S., Horm Metab Res. 36(11-12):742-6 (2004)).

Examples of half-lives of some of the peptides are as follows: exenatide, approximately 2.5 hours; GLP-1, approximately 2 minutes; GIP, approximately 5 minutes; PYY, approximately 8 minutes; glucagon, approximately 6 minutes; oxyntomodulin, approximately 6 minutes; and GLP-2, approximately 6 minutes.

Drug particle formulations for use in the practice of the present invention are exemplified using exenatide. The examples are not intended to be limiting.

In another embodiment, preferred drugs include small molecules. Examples of drugs that may be used in the practice of the present invention include, but are not limited to, the following: chemotherapeutics; hypnotics and sedatives such as pentobarbital sodium, phenobarbital, secobarbital, thiopental, amides and ureas exemplified by diethylisovaleramide and alpha-bromo-isovaleryl urea, urethanes, or disulfanes; heterocyclic hypnotics such as dioxopiperidines, and glutarimides; antidepressants such as isocarboxazid, nialamide, phenelzine, imipramine, tranylcypromine, pargyline); tranquilizers such as chloropromazine, promazine, fluphenazine reserpine, deserpidine, meprobamate, benzodiazepines such as chlordiazepoxide; anticonvulsants such as primidone, diphenylhydantoin, ethltoin, pheneturide, ethosuximide; muscle relaxants and anti-parkinson agents such as mephenesin, methocarbomal, trihexylphenidyl, biperiden, levodopa, also known as L-dopa and L-beta-3-4-dihydroxyphenylalanine; analgesics such as morphine, codeine, meperidine, nalorphine; antipyretics and anti-inflammatory agents such as aspirin, salicylamide, sodium salicylamide, naproxin, ibuprofen; local anesthetics such as procaine, lidocaine, naepaine, piperocaine, tetracaine, dibucane; antispasmodics and anti-ulcer agents such as atropine, scopolamine, methscopolamine, oxyphenonium, papaverine, prostaglandins such as $PGE_1$, $PGE_2$, $PGF_{1alpha}$, $PGF_{2alpha}$, PGA; anti-microbials such as penicillin, tetracycline, oxytetracycline, chlorotetracycline, chloramphenicol, sulfonamides, tetracycline, bacitracin, chlorotetracycline, erythromycin, isoniazid, rifampin, ethambutol, pyrazinamide, rifabutin, rifapentine, cycloserine, ethionamide, streptomycin, amikacin/kanamycin, capreomycin, p-aminosalicyclic acid, levofloxacin, moxifloxacin and gatifloxacin; anti-malarials such as 4-aminoquinolines, 8-aminoquinolines, pyrimethamine, chloroquine, sulfadoxine-pyrimethamine; mefloquine; atovaquone-proguanil; quinine; doxycycline; artemisinin (a sesquiterpene lactone) and derivatives; anti-leishmaniasis agents (e.g., meglumine antimoniate, sodium stibogluconate, amphotericin, miltefosine, and paromomycin); anti-trypanosomiasis agents (e.g., benznidazole and nifurtimox); antiamoebiasis agents (e.g., metronidazole, tinidazole, and diloxanide furoate); anti-protozoal diseases agents (e.g., eflornithine, furazolidone, melarsoprol, metronidazole, ornidazole, paromomycin sulfate, pentamidine, pyrimethamine and tinidazole); hormonal agents such as prednisolone, cortisone, cortisol and triamcinolone, androgenic steroids (for example, methyltestosterone, fluoxmesterone), estrogenic steroids (for example, 17-beta-estradoil and thinyl estradiol), progestational steroids (for example, 17-alpha-hydroxyprogesterone acetate, 19-nor-progesterone, norethindrone); sympathomimetic drugs such as epinephrine, amphetamine, ephedrine, norepinephrine; cardiovascular drugs such as procainamide, amyl nitrate, nitroglycerin, dipyridamole, sodium nitrate, mannitol nitrate; diuretics such as acetazolamide, chlorothiazide, flumethiazide; antiparasitic agents such as bephenium hydroxynaphthoate, dichlorophen, enitabas, dapsone; neoplastic agents such as mechloroethamine, uracil mustard, 5-fluorouracil, 6-thioguanine and procarbazine; hypoglycemic drugs such as tolbutamide, acetohexamide, tolazamide, chlorpropamide; nutritional agents such as vitamins, essential amino acids, and essential fats; eye drugs such as pilocarpine base, pilocarpine hydrochloride, pilocarpine nitrate; antiviral drugs such as disoproxil fumarate, aciclovir, cidofovir, docosanol, famciclovir, fomivirsen, foscarnet, ganciclovir, idoxuridine, penciclovir, trifluridine, tromantadine, valaciclovir, valganciclovir, vidarabine, amantadine, arbidol, oseltamivir, peramivir, rimantadine, zanamivir, abacavir, didanosine, emtricitabine, lamivudine, stavudine, zalcitabine, zidovudine, tenofovir, efavirenz, delavirdine, nevirapine, loviride, amprenavir, atazanavir, darunavir, fosamprenavir, indinavir, lopinavir, nelfinavir, ritonavir, saquinavir, tipranavir, enfuvirtide, adefovir, fomivirsen, imiquimod, inosine, podophyllotoxin, ribavirin, viramidine, fusion blockers specifically targeting viral surface proteins or viral receptors (for example, gp-41 inhibitor (T-20), CCR-5 inhibitor); anti-nausea such as scopolamine, dimenhydrinate); iodoxuridine, hydrocortisone, eserine, phospholine, iodide, as well as other beneficial drugs.

The drugs can also be in various forms including, but not limited to, the following: uncharged molecules; components of molecular complexes; and pharmacologically acceptable salts such as hydrochloride, hydrobromide, sulfate, laurates, palmatates, phosphate, nitrate, borate, acetate, maleate, tartrate, oleates, or salicylates. For acidic drugs, salts of metals, amines or organic cations, for example, quaternary ammonium, can be employed. Furthermore, simple derivatives of the drug such as esters, ethers, amides and the like that have solubility characteristics suitable for the purpose of the invention can also be used herein.

The above drugs and other drugs known to those of skill in the art are useful in methods of treatment for a variety of conditions including but not limited to the following: chronic pain, hemophilia and other blood disorders, endocrine disorders, metabolic disorders, rheumatologic disorders, diabetes (including type 1 and type 2 diabetes mellitus), leukemia, hepatitis, renal failure, infectious diseases (including bacterial infection, viral infection (e.g., infection by human immunodeficiency virus, hepatitis C virus, hepatitis B virus, yellow fever virus, West Nile virus, Dengue virus, Marburg virus, Ebola virus, etc.), and parasitic infection), hereditary diseases (such as cerbrosidase deficiency and adenosine deaminase deficiency), hypertension, septic shock, autoimmune diseases (e.g., Grave's disease, systemic lupus erythematosus, multiple sclerosis, and rheumatoid arthritis), shock and wasting disorders, cystic fibrosis, lactose intolerance, Crohn's diseases, inflammatory bowel disease, gastrointestinal cancers (including colon cancer and rectal cancer), breast cancer, leukemia, lung cancer, bladder cancer, kidney cancer, non-Hodgkin lymphoma, pancreatic cancer, thyroid cancer, endometrial cancer, and other cancers. Further, some of the above agents are useful for the treatment of infectious diseases requiring chronic treatments including, but not limited to, tuberculosis, malaria, leishmaniasis, trypanosomiasis (sleeping sickness and Chagas disease), and parasitic worms.

The amount of drug in drug particle formulations is that amount necessary to deliver a therapeutically effective amount of the agent to achieve the desired therapeutic result in the subject to which the drug is being delivered. In practice, this will vary depending upon such variables, for example, as the particular agent, the severity of the condition, and the desired therapeutic effect. Beneficial agents and their dosage unit amounts are known to the prior art in Goodman & Gilman's The Pharmacological Basis of Therapeutics, 11th Ed., (2005), McGraw Hill; Remington's Pharmaceutical Sciences, 18th Ed., (1995), Mack Publishing Co.; and Martin's Physical Pharmacy and Pharmaceutical Sciences, 1.00 edition (2005), Lippincott Williams & Wilkins. Further, highly concentrated drug particles are described in U.S. Patent Publication No. 2010/0092566. Typically, for an osmotic delivery system, the volume of the chamber comprising the drug formulation is between about 100 µl to about 1000 µl, more preferably between about 140 µl and about 200 µl. In one embodiment, the volume of the chamber comprising the drug formulation is about 150 µl.

Drug particle formulations of the invention are preferably chemically and physically stable for at least 1 month, preferably at least 3 months, more preferably at least 6 months, more preferably at least 12 months at delivery temperature. The delivery temperature is typically normal human body temperature, for example, about 37° C., or slightly higher, for example, about 40° C. Further, drug particle formulations of the present invention are preferably chemically and physically stable for at least 3 months, preferably at least 6 months, more preferably at least 12 months, at storage temperature. Examples of storage temperatures include refrigeration temperature, for example, about 5° C.; or room temperature, for example, about 25° C.

A drug particle formulation may be considered chemically stable if less than about 25%; preferably less than about 20%, more preferably less than about 15%, more preferably less than about 10%, and more preferably less than about 5% breakdown products of the drug particles are formed after about 3 months, preferably after about 6 months, preferably after about 12 months at delivery temperature and after about 6 months, after about 12 months, and preferably after about 24 months at storage temperature.

A drug particle formulation may be considered physically stable if less than about 10%, preferably less than about 5%, more preferably less than about 3%, more preferably less than 1% aggregates of the drug are formed after about 3 months, preferably after about 6 months, at delivery temperature and about 6 months, preferably about 12 months, at storage temperature.

When the drug in the drug particle formulation is a protein, the protein solution is kept in a frozen condition and lyophilized or spray dried to a solid state. Tg (glass transition temperature) may be one factor to consider in achieving stable compositions of protein. While not intending to be bound by any particular theory, the theory of formation of a high Tg amorphous solid to stabilize peptides, polypeptides, or proteins has been utilized in pharmaceutical industry. Generally, if an amorphous solid has a higher Tg, such as 100° C., peptide products will not have mobility when stored at room temp or even at 40° C. because the storage temperature is below the Tg. Calculations using molecular information have shown that if a glass transition temperature is above a storage temperature of 50° C. that there is zero mobility for molecules. Zero mobility of molecules correlates with better stability. Tg is also dependent on the moisture concentration in the product formulation. Generally, the more moisture, the lower the Tg of the composition.

Accordingly, in some aspects of the present invention, excipients with higher Tg may be included in the protein formulation to improve stability, for example, sucrose (Tg=75° C.) and trehalose (Tg=110° C.). Preferably, particle formulations are formable into particles using processes such as spray drying, lyophilization, desiccation, freeze-drying, milling, granulation, ultrasonic drop creation, crystallization, precipitation, or other techniques available in the art for forming particles from a mixture of components. In one embodiment of the invention the particles are spray dried. The particles are preferably substantially uniform in shape and size.

The particles are typically sized such that they can be delivered via an implantable osmotic drug delivery device. Uniform shape and size of the particles typically helps to provide a consistent and uniform rate of release from such a delivery device; however, a particle preparation having a non-normal particle size distribution profile may also be used. For example, in a typical implantable osmotic delivery device having a delivery orifice, the size of the particles is less than about 30%, more preferably is less than about 20%, more preferably is less than about than 10%, of the diameter of the delivery orifice. In an embodiment of the particle formulation for use with an osmotic delivery system, wherein the delivery orifice diameter of the implant is about 0.5 mm, particle sizes may be, for example, less than about 150 microns to about 50 microns. In an embodiment of the particle formulation for use with an osmotic delivery system, wherein the delivery orifice diameter of the implant is about 0.1 mm, particle sizes may be, for example, less than about 30 microns to about 10 microns. In one embodiment, the orifice is about 0.25 mm (250 microns) and the particle size is about 2 microns to about 5 microns.

Typically, the particles of the particle formulations, when incorporated in a suspension vehicle, do not settle in less than about 3 months, preferably do not settle in less than about 6 months, more preferably do not settle in less than about 12 months, more preferably do not settle in less than about 24 months at delivery temperature, and most preferably do not settle in less than about 36 months at delivery temperature. The suspension vehicles typically have a viscosity of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise. Generally speaking, smaller particles tend to have a lower settling rate in viscous suspension vehicles than larger particles. Accordingly, micron- to nano-sized particles are typically desirable. In viscous suspension formulation, particles of about 2 microns to about 7 microns of the present invention will not settle for at least 20 years at room temperature based on simulation modeling studies. In an embodiment of the particle formulation of the present invention, for use in an implantable osmotic delivery device, comprises particles of sizes less than about 50 microns, more preferably less than about 10 microns, more preferably in a range from about 2 microns to about 7 microns.

In one embodiment, a drug particle formulation comprises a drug, as described above, one or more stabilizers, and optionally a buffer. The stabilizers may be, for example, carbohydrate, antioxidant, amino acid, buffer, inorganic compound, or surfactant. The amounts of stabilizers and buffer in the particle formulation can be determined experimentally based on the activities of the stabilizers and buffers and the desired characteristics of the formulation, in view of the teachings of the present specification. Typically, the amount of carbohydrate in the formulation is determined by aggregation concerns. In general, the carbohydrate amount should not be too high so as to avoid promoting crystal growth in the presence of water due to excess carbohydrate unbound to drug. Typically, the amount of antioxidant in the formulation is determined by oxidation concerns, while the amount of amino acid in the formulation is determined by oxidation concerns and/or formability of particles during spray drying. Typically, the amount of buffer in the formulation is determined by pre-processing concerns, stability concerns, and formability of particles during spray drying. Buffer may be required to stabilize drug during processing, e.g., solution preparation and spray drying, when all excipients are solubilized.

Examples of carbohydrates that may be included in the particle formulation include, but are not limited to, monosaccharides (e.g., fructose, maltose, galactose, glucose, D-mannose, and sorbose), disaccharides (e.g., lactose, sucrose, trehalose, and cellobiose), polysaccharides (e.g., raffinose, melezitose, maltodextrins, dextrans, and starches), and alditols (acyclic polyols; e.g., mannitol, xylitol, maltitol, lactitol, xylitol sorbitol, pyranosyl sorbitol, and myoinsitol). Preferred carbohydrates include disaccharides and/or non-reducing sugars, such as sucrose, trehalose, and raffinose.

Examples of antioxidants that may be included in the particle formulation include, but are not limited to, methionine, ascorbic acid, sodium thiosulfate, catalase, platinum, ethylenediaminetetraacetic acid (EDTA), citric acid, cysteins, thioglycerol, thioglycolic acid, thiosorbitol, butylated hydroxanisol, butylated hydroxyltoluene, and propyl gallate. Further, amino acids that readily oxidize can be used as antioxidants, for example, cysteine, methionine, and tryptophan. A preferred antioxidant is methionine.

Examples of amino acids that may be included in the particle formulation include, but are not limited to, arginine, methionine, glycine, histidine, alanine, L-leucine, glutamic acid, iso-leucine, L-threonine, 2-phenylamine, valine, norvaline, praline, phenylalanine, trytophan, serine, asparagines, cysteine, tyrosine, lysine, and norleucine. Preferred amino acids include those that readily oxidize, e.g., cysteine, methionine, and trytophan.

Examples of buffers that may be included in the particle formulation include, but are not limited to, citrate, histidine, succinate, phosphate, maleate, tris, acetate, carbohydrate, and gly-gly. Preferred buffers include citrate, histidine, succinate, and tris.

Examples of inorganic compounds that may be included in the particle formulation include, but are not limited to, NaCl, $Na_2SO4$, $NaHCO_3$, KCl, $KH_2PO4$, $CaCl_2$, and $MgCl_2$.

In addition, the particle formulation may include other excipients, such as surfactants, and salts. Examples of surfactants include, but are not limited to, Polysorbate 20, Polysorbate 80, PLURONIC® (BASF Corporation, Mount Olive, N.J.) F68, and sodium docecyl sulfate (SDS). Examples of salts include, but are not limited to, sodium chloride, calcium chloride, and magnesium chloride.

All components included in the particle formulation are typically acceptable for pharmaceutical use in mammals, in particular, in humans.

In summary, a selected drug or combination of drugs is formulated into dried powders in solid state, which preserve maximum chemical and biological stability of the drug. The particle formulation offers long-term storage stability at high temperature, and therefore, allows delivery to a subject of stable and biologically effective drug for extended periods of time.

3.2.0 Vehicle Formulations and Suspension Formulations

In one aspect, the suspension vehicle provides a stable environment in which the drug particle formulation is dispersed. The drug particle formulations are chemically and physically stable (as described above) in the suspension vehicle. The suspension vehicle typically comprises one or more polymer and one or more solvent that form a solution of sufficient viscosity to uniformly suspend the particles comprising the drug. The suspension vehicle may comprise further components, including, but not limited to, surfactants, antioxidants, and/or other compounds soluble in the vehicle.

The viscosity of the suspension vehicle is typically sufficient to prevent the drug particle formulation from settling during storage and use in a method of delivery, for example, in an implantable, osmotic delivery device. The suspension vehicle is biodegradable in that the suspension vehicle disintegrates or breaks down over a period of time in response to a biological environment, while the drug particle is dissolved in the biological environment and the active pharmaceutical ingredient (i.e., the drug) in the particle is absorbed.

The solvent in which the polymer is dissolved may affect characteristics of the suspension formulation, such as the behavior of drug particle formulation during storage. A solvent may be selected in combination with a polymer so that the resulting suspension vehicle exhibits phase separation upon contact with the aqueous environment. In some embodiments of the invention, the solvent may be selected in combination with the polymer so that the resulting suspension vehicle exhibits phase separation upon contact with the aqueous environment having less than approximately about 10% water.

The solvent may be an acceptable solvent that is not miscible with water. The solvent may also be selected so that the polymer is soluble in the solvent at high concentrations, such as at a polymer concentration of greater than about 30%. Examples of solvents useful in the practice of the present invention include, but are not limited to, lauryl alcohol, benzyl benzoate, benzyl alcohol, lauryl lactate, decanol (also called decyl alcohol), ethyl hexyl lactate, and long chain ($C_8$ to $C_{24}$) aliphatic alcohols, esters, or mixtures thereof. The solvent used in the suspension vehicle may be "dry," in that it has a low moisture content. Preferred solvents for use in formulation of the suspension vehicle include lauryl lactate, lauryl alcohol, benzyl benzoate, and mixtures thereof.

Examples of polymers for formulation of the suspension vehicles of the present invention include, but are not limited to, a polyester (e.g., polylactic acid or polylacticpolyglycolic acid), a polymer comprising pyrrolidones (e.g., polyvinylpyrrolidone having a molecular weight ranging from approximately 2,000 to approximately 1,000,000), ester or ether of an unsaturated alcohol (e.g., vinyl acetate), polyoxyethylenepolyoxypropylene block copolymer, or mixtures thereof. Polyvinylpyrrolidone can be characterized by its K-value (e.g., K-17), which is a viscosity index. In one embodiment, the polymer is polyvinylpyrrolidone having a molecular weight of 2,000 to 1,000,000. In a preferred embodiment the polymer is polyvinylpyrrolidone K-17 (typically having an approximate average molecular weight range of 7,900-10,800). The polymer used in the suspension vehicle may include one or more different polymers or may include different grades of a single polymer. The polymer used in the suspension vehicle may also be dry or have a low moisture content.

Generally speaking, a suspension vehicle for use in the present invention may vary in composition based on the desired performance characteristics. In one embodiment, the suspension vehicle may comprise about 40 wt % to about 80 wt % polymer(s) and about 20 wt % to about 60 wt % solvent(s). Preferred embodiments of a suspension vehicle include vehicles formed of polymer(s) and solvent(s) combined at the following ratios: about 25 wt % solvent and about 75 wt % polymer; about 50 wt % solvent and about 50 wt % polymer; about 75 wt % solvent and about 25 wt % polymer. Accordingly, in some embodiments the suspension vehicle may comprise selected components and in other embodiments consist essentially of selected components.

The suspension vehicle may exhibit Newtonian behavior. The suspension vehicle is typically formulated to provide a viscosity that maintains a uniform dispersion of the particle formulation for a predetermined period of time. This helps facilitate making a suspension formulation tailored to provide controlled delivery of the drug contained in the drug particle formulation. The viscosity of the suspension vehicle may vary depending on the desired application, the size and type of the particle formulation, and the loading of the particle formulation in the suspension vehicle. The viscosity of the suspension vehicle may be varied by altering the type or relative amount of the solvent or polymer used.

The suspension vehicle may have a viscosity ranging from about 100 poise to about 1,000,000 poise, preferably from about 1,000 poise to about 100,000 poise. In preferred embodiments, the suspension vehicles typically have a viscosity, at 33° C., of between about 5,000 to about 30,000 poise, preferably between about 8,000 to about 25,000 poise, more preferably between about 10,000 to about 20,000 poise. In one embodiment, the suspension vehicle has a viscosity of about 15,000 poise, plus or minus about 3,000 poise, at 33° C. The viscosity may be measured at 33° C., at a shear rate of $10^{-4}$/sec, using a parallel plate rheometer.

The suspension vehicle may exhibit phase separation when contacted with the aqueous environment; however, typically the suspension vehicle exhibits substantially no phase separation as a function of temperature. For example, at a temperature ranging from approximately 0° C. to approximately 70° C. and upon temperature cycling, such as cycling from 4° C. to 37° C. to 4° C., the suspension vehicle typically exhibits no phase separation.

The suspension vehicle may be prepared by combining the polymer and the solvent under dry conditions, such as in a dry box. The polymer and solvent may be combined at an elevated temperature, such as from approximately 40° C. to approximately 70° C., and allowed to liquefy and form the single phase. The ingredients may be blended under vacuum to remove air bubbles produced from the dry ingredients. The ingredients may be combined using a conventional mixer, such as a dual helix blade or similar mixer, set at a speed of approximately 40 rpm. However, higher speeds may also be used to mix the ingredients. Once a liquid solution of the ingredients is achieved, the suspension vehicle may be cooled to room temperature. Differential scanning calorimetry (DSC) may be used to verify that the suspension vehicle is a single phase. Further, the components of the vehicle (e.g., the solvent and/or the polymer) may be treated to substantially reduce or substantially remove peroxides (e.g., by treatment with methionine; see, e.g., U.S., Patent Application Publication No. 2007-0027105).

The drug particle formulation is added to the suspension vehicle to form a suspension formulation. In some embodiments the suspension formulation may comprise a drug particle formulation and a suspension vehicle and in other embodiments consist essentially of a drug particle formulation and a suspension vehicle.

The suspension formulation may be prepared by dispersing the particle formulation in the suspension vehicle. The suspension vehicle may be heated and the particle formulation added to the suspension vehicle under dry conditions. The ingredients may be mixed under vacuum at an elevated temperature, such as from about 40° C. to about 70° C. The ingredients may be mixed at a sufficient speed, such as from about 40 rpm to about 120 rpm, and for a sufficient amount of time, such as about 15 minutes, to achieve a uniform dispersion of the particle formulation in the suspension vehicle. The mixer may be a dual helix blade or other suitable mixer. The resulting mixture may be removed from the mixer, sealed in a dry container to prevent water from contaminating the suspension formulation, and allowed to cool to room temperature before further use, for example, loading into an implantable, drug delivery device, unit dose container, or multiple-dose container.

The suspension formulation typically has an overall moisture content of less than about 10 wt %, preferably less than about 5 wt %, and more preferably less than about 4 wt %.

In preferred embodiments, the suspension formulations of the present invention are substantially homogeneous and flowable to provide delivery of the drug particle formulation from the osmotic delivery device to the subject.

In summary, the components of the suspension vehicle provide biocompatibility. Components of the suspension vehicle offer suitable chemico-physical properties to form stable suspensions of drug particle formulations. These properties include, but are not limited to, the following: viscosity of the suspension; purity of the vehicle; residual moisture of the vehicle; density of the vehicle; compatibility with the dry powders; compatibility with implantable devices; molecular weight of the polymer; stability of the vehicle; and hydrophobicity and hydrophilicity of the vehicle. Thee properties can be manipulated and controlled, for example, by variation of the vehicle composition and manipulation of the ratio of components used in the suspension vehicle.

4.0.0 Delivery of Suspension Formulations

The suspension formulations described herein may be used in an implantable, osmotic drug delivery device to provide zero-order, continuous, controlled, and sustained delivery of a compound over an extended period of time, such as over weeks, months, or up to about one year or more. Such an implantable osmotic drug delivery device is typically capable of delivering the suspension formulation, comprising the drug, at a desired flow rate over a desired period of time. The suspension formulation may be loaded into the implantable, osmotic drug delivery device by conventional techniques.

A dose and delivery rate can be selected to achieve a desired blood concentration of a drug generally within less than about 6 half-lives of the drug within the subject after implantation of the device. The blood concentration of the drug is selected to give the optimal therapeutic effects of the drug while avoiding undesirable side effects that may be induced by excess concentration of the drug, while at the same time avoiding peaks and troughs that may induce side effects associated with peak or trough plasma concentrations of the drug.

The implantable, osmotic drug delivery device typically includes a reservoir having at least one orifice through which the suspension formulation is delivered. The suspension formulation may be stored within the reservoir. In a preferred embodiment, the implantable, drug delivery device is an osmotic delivery device, wherein delivery of the drug is osmotically driven. Some osmotic delivery devices and their component parts have been described, for example, the DUROS® delivery device or similar devices (see, e.g., U.S. Pat. Nos. 5,609,885; 5,728,396; 5,985,305; 5,997,527; 6,113,938; 6,132,420; 6,156,331; 6,217,906; 6,261,584; 6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; 7,112,335; 7,163,688; U.S. Patent Publication Nos. 2005/0175701, 2007/0281024, 2008/0091176, and 2009/0202608).

The DUROS® delivery device typically consists of a cylindrical reservoir which contains the osmotic engine, piston, and drug formulation. The reservoir is capped at one end by a controlled-rate, semi-permeable membrane and capped at the other end by a diffusion moderator through which suspension formulation, comprising the drug, is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The DUROS® device releases a drug at a predetermined rate based on the principle of osmosis. Extracellular fluid enters the DUROS® device through a semi-permeable membrane directly into a salt engine that expands to drive the piston at a slow and even delivery rate. Movement of the piston forces the drug formulation to be released through the orifice or exit port at a predetermined sheer rate. In one embodiment of the present invention, the reservoir of the DUROS® device is load with a suspension formulation wherein the device is capable of delivering the suspension formulation to a subject over an extended period of time (e.g., about 1, about 3, about 6, about 9, about 10, or about 12 months) at a pre-determined, therapeutically effective delivery rate.

The release rate of the drug from the osmotic delivery device typically provides a subject with a predetermined target dose of a drug, for example, a therapeutically effective daily dose delivered over the course of a day; that is, the release rate of the drug from the device, provides substantial steady-state delivery of the drug at a therapeutic concentration to the subject.

Typically, for an osmotic delivery device, the volume of a beneficial agent chamber comprising the beneficial agent formulation is between about 100 µl to about 1000 µl, more preferably between about 120 µl and about 500 µl, more preferably between about 150 µl and about 200 µl.

Typically, the osmotic delivery device is implanted within the subject, for example, subcutaneously to provide subcutaneous drug delivery. The device(s) can be implanted subcutaneously into either or both arms (e.g., in the inside, outside, or back of the upper arm) or the abdomen. Preferred locations in the abdominal area are under the abdominal skin in the area extending below the ribs and above the belt line. To provide a number of locations for implantation of one or more osmotic delivery device within the abdomen, the abdominal wall can be divided into 4 quadrants as follows: the upper right quadrant extending 5-8 centimeters below the right ribs and about 5-8 centimeters to the right of the midline, the lower right quadrant extending 5-8 centimeters above the belt line and 5-8 centimeters to the right of the midline, the upper left quadrant extending 5-8 centimeters below the left ribs and about 5-8 centimeters to the left of the midline, and the lower left quadrant extending 5-8 centimeters above the belt line and 5-8 centimeters to the left of the midline. This provides multiple available locations for implantation of one or more devices on one or more occasions. Implantation and removal of osmotic delivery devices are generally carried out by medical professionals using local anesthesia (e.g., lidocaine).

Termination of treatment by removal of an osmotic delivery device from a subject is straightforward, and provides the important advantage of immediate cessation of delivery of the drug to the subject.

The suspension formulations may also be used in infusion pumps, for example, the ALZET® (DURECT Corporation, Cupertino, Calif.) osmotic pumps which are miniature, infusion pumps for the continuous dosing of laboratory animals (e.g., mice and rats).

5.0.0 Exemplary Advantages of Certain Aspects of the Present Invention

In one aspect, the present invention relates to methods of treatment with continuous delivery of incretin mimetics (e.g., exenatide), for example, by use of an implantable osmotic delivery device. Experiments described herein have demonstrated that continuous delivery of exenatide using an implantable osmotic delivery device, provided the following benefits for subjects in need of treatment: treating type 2 diabetes mellitus, improving glycemic control (as measured, e.g., by glucose levels, HbA1c, and/or fructosamine), reducing HbA1c, reducing fasting plasma glucose, reducing postprandial blood glucose levels, reducing adverse gastrointestinal events (e.g., nausea and vomiting) relative to twice-daily injections, weight loss, reducing LDL-C, reducing systolic blood pressure, treating hypertension, reducing fructosamine levels, and improving of quality of life for subjects undergoing treatment.

In addition, the continuous delivery of incretin mimetics (e.g., exenatide) may be used in the practice of the following methods: treating obesity, controlling appetite, reducing caloric intake, reducing food intake, suppressing appetite, inducing anorexia, treating impaired glucose tolerance, treating post-prandial hyperglycemia, treating post-prandial dumping syndrome, treating hyperglycemic conditions, reducing triglycerides, reducing cholesterol, increasing urine flow, decreasing potassium concentration in the urine, alleviating toxic hypervolemia, inducing rapid diuresis, pre-surgical patient preparation, post-surgical patient treatment, increasing renal plasma flow and glomerular filtration rate, treating pre-eclampsia or eclampsia during pregnancy, increasing cardiac contractility, treating renal failure, treating congestive heart failure, treating nephrotic syndrome, treating pulmonary edema, treating systemic edema, treating cirrhosis, treating impaired glucose tolerance, treating pre-diabetes (blood glucose levels that are higher than normal but not yet high enough to be diagnosed as diabetes), treating type 1 diabetes mellitus (e.g., in combination with insulin), reducing risk of a cardiovascular event due to impaired glucose tolerance, reducing risk of a cerebrovascular event due to impaired glucose tolerance, delaying the progression of diabetes, ameliorating diabetes, delaying diabetes onset, inducing β cell regeneration, restoring normoglycemia, providing euglycemic control, treating peripheral vascular disease, treating acute coronary syndrome, treating cardiomyopathy, treating gestational diabetes, treating polycystic ovary syndrome, treating or preventing nephropathy, and treating diabetes induced by a variety of diseases or conditions (for example, steroid induced diabetes, human immunodeficiency virus treatment-induced diabetes, latent autoimmune diabetes in adults, nonalcoholic steatohepatitis, nonalcoholic fatty liver disease, hypoglycemia unawareness, restrictive lung disease, chronic obstructive pulmonary disease, lipoatrophy and metabolic syndrome).

The present invention also provides treatment methods for delivery of an incretin mimetic having the following advantages. The continuous delivery from, for example, an osmotic delivery device, ensures 100% treatment compliance for subjects and avoids the need for twice-daily, daily, weekly, or even monthly injections because the devices described herein can deliver an incretin mimetic for time periods of up to a about year or more. The avoidance of self-injection is a particular advantage for a subject who is needle phobic. Further, use of implantable devices for continuous delivery provides treatment convenience and avoids scheduling conflicts, for example, with meals, and also eliminates the inconvenience of administration of a drug by injection, for example, when subjects are in public or busy with daily activities. Also, frequent self-administration of a drug reminds subjects of their disease state and carries a stigma associated with the disease and/or treatment; whereas continuous delivery of a drug from an implanted osmotic device may offer subjects some respite from such reminders and stigma.

The present invention also provides methods to treat subjects at dosage levels of incretin mimetics previously thought to be higher than tolerable dosage levels. For example, continuous delivery of exenatide is described herein for dosages tolerated at least up to 80 mcg/day.

In another aspect the present invention provides methods of dosage escalation. In one embodiment, multiple devices for continuous delivery of a drug, for example, an incretin mimetic, are provided. Each device is capable of delivering a particular drug dose per day. A low-dose device is initially implanted, followed by removal and implantation of a higher daily dose device. Alternatively, the first device may be kept in place and a second device implanted to increase the daily dose. In another alternative, a subject may be started by dosing with an injectable form of the drug (e.g., twice-daily, once-daily, once-weekly, or once- or twice-monthly injection) and transitioned to an implantable device to provide continuous delivery after an initial period. Such transitioning from injectable to implantable may, for example, allow subjects or physicians to try a drug and perhaps be observed for any immediate adverse effects before implantation of a device. Injectable to implantable transitions may also be useful for treatment of subjects who are particularly nervous about possible drug side effects. Also, providing the drug by injection or by continuous delivery at low dose may permit tolerization of the drug at low dose before changing to higher and more efficacious therapeutic doses.

Optimal time periods are determined for a drug concerning how long an initial device remains in place before replacement with a higher dose delivery device. Similarly optimal time periods are determined for how long an initial phase of treatment by injection goes on before implantation of an osmotic delivery device. For example, treatment is commenced at a low dose with low incidence of side effects (e.g., for about 2 weeks, about 3 months, about 6 months, about 9 months, about a year). The subject adjusts to that dose and subsequently a higher dose delivery device is implanted providing dose escalation. Alternatively, a subject who has been treated with an injectable form dose escalates to an implantable osmotic delivery device. Such dose escalations were shown from the data presented herein to achieve additional benefits in glucose regulation and weight loss. Examples of initial dosages include, but are not limited to, delivery of about 1 mcg/day to about 20 mcg/day, followed by dose escalation to about 5 mcg/day to about 1,000 mcg/day. Preferably, escalation of incretin mimetic doses include, but are not limited to, the following: about 10 mcg/day followed by about 20 mcg/day; about 10 mcg/day followed by about 40 mcg/day; about 10 mcg/day followed by about 60 mcg/day; about 10 mcg/day followed by about 80 mcg/day; about 20 mcg/day followed by about 40 mcg/day; about 20 mcg/day followed by about 60 mcg/day; about 20 mcg/day followed by about 80 mcg/day; about 40 mcg/day followed by about 60 mcg/day; about 40 mcg/day followed by about 80 mcg/day; and about 60 mcg/day followed by about 80 mcg/day. In one embodiment, the present invention includes kits and methods for manufacturing kits comprising one or more lower dose osmotic delivery devices and one or more higher dose osmotic delivery devices (the lower and higher dosages being relative to the other devices in the kit). Such kits may optionally include an implanter, lidocaine, and sterile field/supplies.

Generally, dose escalation is from a low dose of incretin mimetic, for example, about 1 mcg/day to about 30 mcg/day, to a high dose of greater than the low dose to about 80 mcg/day.

In another aspect, the present invention provides a method of treating diabetes without a substantial increase in insulin secretion using an incretin mimetic. In a preferred embodiment of this aspect of the present invention the incretin mimetic is exenatide. Data obtained in the course of the studies described herein demonstrated that, at higher doses of continuous delivery of exenatide (e.g., 20 mcg/day, 40 mcg/day, and 80 mcg/day), effective treatment of diabetes was achieved in the absence of an increase in insulin production. Insulin levels were measured by radioimmunoassay.

In another aspect, the methods of the present invention allow for the administration of a drug, e.g., an incretin mimetic, without a substantial initial drug burst that typically occurs with depot injections (e.g., initial drug burst of from about 5% of total drug in depot formulation to about 1% of total drug in depot formulation) that provide sustained delivery over a period of time (e.g., depot injections formulated using poly(lactides), poly(glycolides), poly(lactide-co-glycolides), poly(lactic acid)s, poly(glycolic acid)s, poly(lactic acid-co-glycolic acid)s and blends and copolymers thereof).

In a further aspect the present invention is directed to methods of providing greater reduction in plasma blood glucose in a shorter time period (e.g. within 1-5 days) than can be achieved using twice-daily daily injections, comprising providing continuous delivery of an incretin mimetic, for example, exenatide. In one embodiment, continuous delivery is achieved by use of an implantable osmotic delivery device.

Another advantage of the present invention is the ability to remove the delivery device providing continuous delivery of the drug and provide rapid termination of drug delivery for any reason, for example, in the case of myocardial infarction, pregnancy, pancreatitis or suspected pancreatitis, emergency medical care (e.g., termination of drug therapies), or adverse drug reactions.

The present invention uniquely addresses unmet needs relative to injectable incretin mimetics. For example, one shortcoming of twice-daily injectable exenatide is that greater than 65% of subjects are not treated to or maintained at HbA1c treatment goals. Another disadvantage of twice-daily injectable exenatide is that greater than 65% of these subjects become noncompliant between 6-12 months when attempting to adhere to the injection treatment schedule. Also, 65% of subjects treated with twice-daily injectable exenatide are overweight and need sustained weight loss.

Experiments described herein (e.g., Example 3) demonstrated that the methods of and osmotic devices comprising an incretin mimetic for use in methods of treating type 2 diabetes mellitus by continuous delivery as set forth by the present invention provide sustained treatment of subjects at target doses, complete subject compliance with the treatment, and sustained weight loss. A target dose typically provides substantial steady-state delivery of the incretin mimetic at a therapeutic concentration to the subject.

The data presented in the Experimental section herein demonstrate that the present invention provides methods of and osmotic devices comprising incretin mimetics for use in methods of treating type 2 diabetes mellitus by continuous delivery, wherein substantial steady-state delivery of the incretin mimetic at therapeutic concentrations is achieved within a time period of about 7 days or less, about 6 days or less, about 5 days or less, about 4 days or less, about 3 days or less, preferably about 2 days or less, and more preferably about 1 day or less, after implantation of the osmotic delivery device in the subject.

The data also demonstrate that the present invention provides methods of and osmotic devices comprising incretin mimetics for use in methods of treating type 2 diabetes mellitus by continuous delivery, wherein a significant decrease in fasting plasma glucose concentration, relative to the fasting plasma glucose concentration before implantation, is achieved after implantation of the osmotic delivery device in the subject within a time period of about 7 days or less, about 6 days or less, about 5 days or less, about 4 days or less, about 3 days or less, preferably about 2 days or less, and more preferably about 1 day or less, after implantation of the osmotic delivery device in the subject.

The data also demonstrate that the present invention provides the capability to terminate the continuous delivery such that the concentration of an incretin mimetic is substantially undetectable in a blood sample from the subject, after termination of continuous delivery, in less than about 6 half-lives of the drug after termination of continuous delivery, in less than about 5 half-lives of the drug after termination of continuous delivery, in less than about 4 half-lives of the drug after termination of continuous delivery, or in less than about 3 half-lives of the drug after termination of continuous delivery. Further, the data show that treatment by continuous delivery of an incretin mimetic provided better decreases in HbA1c than treatment by injection.

Also, the data illustrate that the methods of and osmotic devices comprising an incretin mimetic for use in methods of treating type 2 diabetes mellitus by continuous delivery as described herein provide improved tolerization to dose escalation of the incretin mimetic relative to injection of the incretin mimetic.

In addition, these data presented herein demonstrate a significant advantage of the implanted osmotic delivery device of the present invention over incretin mimetic administration via injection in terms of reported quality of life for treated subjects.

The comparative data described below demonstrate the superior treatment outcomes using the methods of and osmotic devices comprising an incretin mimetic for use in methods of treating type 2 diabetes mellitus by continuous delivery of the present invention, in combination with metformin therapy, relative to other treatment methods. Such other treatment methods include twice-daily injection of exenatide, once-weekly injection of exenatide, once-daily injection of liraglutide, once-weekly injection of taspoglutide, once-daily orally administered sitagliptin, and once-daily orally administered pioglitazone.

In summary, the methods of and osmotic devices comprising an incretin mimetic, for example, exenatide, for use in methods of treating type 2 diabetes mellitus by continuous delivery as described herein provide a new standard of effective treatment. The present invention provides superior HbA1c reduction, improved weight loss, and complete compliance, as well as long-term glycemic control relative to the use of dipeptidyl peptidase-4 (DPP-4) inhibitors (e.g., sitagliptin), thiazolidinediones (TZDs) (e.g., pioglitazone), other injectable incretin mimetics (e.g., liraglutide and taspoglutide), and twice-daily or once-weekly injection of exenatide. Further, the present invention provides better incretin mimetic treatment tolerability because no self-injections are required and the methods of and osmotic devices comprising an incretin mimetic for use in methods of treating type 2 diabetes mellitus by continuous delivery provide improved gastrointestinal tolerance.

Experimental

The following examples are put forth so as to provide those of ordinary skill in the art with a complete disclosure and description of how to practice the present invention, and are not intended to limit the scope of what the inventors regard as the invention. Efforts have been made to ensure accuracy with respect to numbers used (e.g., amounts, concentrations, percent changes, etc.) but some experimental errors and deviations should be accounted for. Unless indicated otherwise, temperature is in degrees Centigrade and pressure is at or near atmospheric.

The compositions used to practice the methods of the present invention meet the specifications for content and purity required of pharmaceutical products. Further examples of suspension formulations comprising incretin mimetics can be found in U.S. Patent Publication Nos. 2006/0193918, 2008/0260840, and 2010/0092566.

EXAMPLE 1

Description of a Typical Osmotic Delivery Device

Suspension formulations comprising exenatide particles suspended in solvent/polymer vehicles were developed for the treatment of type 2 diabetes mellitus. Suspension formulations were loaded into a DUROS® device for subcutaneous implantation to deliver exenatide at a continuous and consistent rate.

Figure 4:
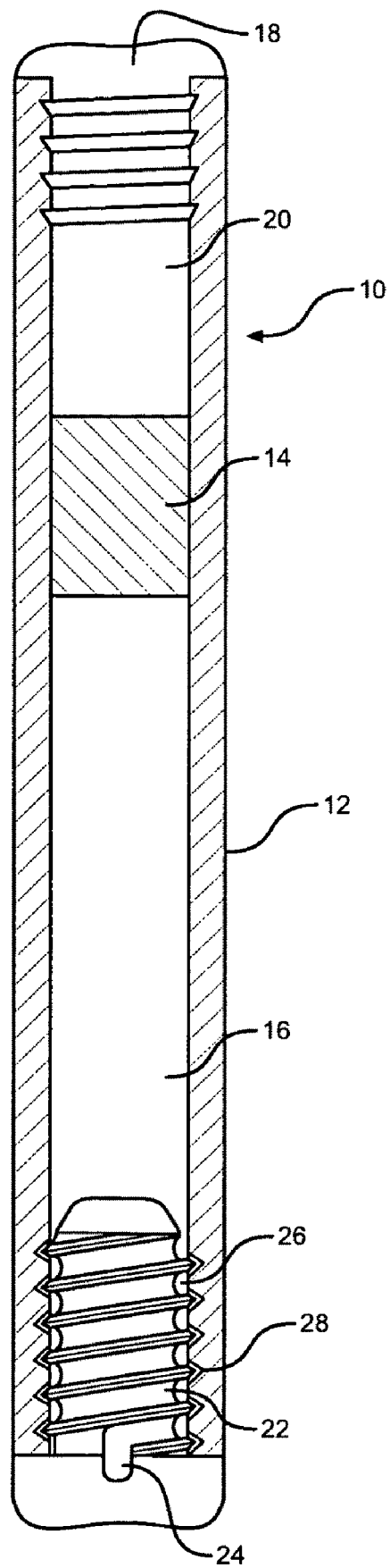
FIG. 4 presents a partial cross-sectional view of one embodiment of an osmotic delivery device useful in the practice of the present invention.

FIG. 4 depicts an example of a DUROS® delivery system useful in the practice of the present invention. In FIG. 4, the osmotic delivery device 10 is shown comprising a reservoir 12. A piston assembly 14 is positioned in the lumen of the reservoir and divides the lumen into two chambers. In this example, the chamber 16 contains a beneficial agent formulation and the chamber 20 contains an osmotic agent formulation. A semi-permeable membrane 18 is positioned at a first distal end of the reservoir, adjacent the chamber 20 containing the osmotic agent formulation. A diffusion moderator 22 is positioned in mating relationship at a second distal end of the reservoir 12, adjacent the chamber 16 containing the suspension formulation, comprising the drug. The diffusion moderator 22 includes a delivery orifice 24. The diffusion moderator 22 may be any suitable flow device having a delivery orifice. In this embodiment, the flow path 26 is formed between a threaded diffusion moderator 22 and threads 28 formed on the interior surface of the reservoir 12. In alternative embodiments, the diffusion moderator can, for example, (i) be press-fit (or friction fit) through an opening and contacting a smooth interior surface of the reservoir, or (ii) comprise two pieces with an outer shell constructed and arranged for positioning in an opening, an inner core inserted in the outer shell, and a fluid channel having a spiral shape defined between the outer shell and the inner core (e.g., U.S. Patent Publication No. 2007/0281024).

Fluid is imbibed into the chamber 20 through the semi-permeable membrane 18. The beneficial agent formulation is dispensed from the chamber 16 through the delivery orifice 24 in the diffusion moderator 22. The piston assembly 14 engages and seals against the interior wall of the reservoir 12, thereby isolating the osmotic agent formulation in chamber 20 and fluid imbibed through the semi-permeable membrane 18 from the beneficial agent formulation in chamber 16. At steady-state, the suspension formulation is released through the delivery orifice 24 in the diffusion moderator 22 at a rate corresponding to the rate at which external fluid is imbibed into the chamber 20 through the semi-permeable membrane 18. That is, the DUROS® delivery device releases drug at a predetermined rate based on the principle of osmosis. Extracellular fluid enters the DUROS® delivery device through the semi-permeable membrane directly into the osmotic engine that expands to drive the piston at a slow and consistent rate of travel. Movement of the piston forces the drug formulation to be released through the orifice of the diffusion moderator.

The semi-permeable membrane 18 may be in the form of a plug that is resiliently engaged in sealing relationship with the interior surface of the reservoir 12. In FIG. 4, it is shown to have ridges that serve to frictionally engage the semi-permeable membrane 18 with the interior surface of the reservoir 12.

These DUROS® delivery devices allow for zero-order, continuous, and controlled subcutaneous delivery of exenatide at consistent rate, which provides several advantages as a treatment of type 2 diabetes mellitus; for example, relatively constant blood therapeutic concentrations of exenatide allow for better control of blood glucose concentrations and may moderate the risk of secondary disease otherwise associated with poorly controlled type 2 diabetes mellitus. These DUROS® delivery devices provide treatment durations of about 3 to about 12 months over a broad range of dosages with preserved stability of the exenatide.

Unlike daily or twice-daily injections of exenatide, the DUROS® delivery devices maintain consistent blood concentrations of exenatide. This is particularly important during all meal periods and overnight. The DUROS® delivery device does not require any action on the part of the subject to ensure therapeutic compliance.

In addition, these DUROS® delivery devices may have safety advantages compared to daily or twice-daily injections of exenatide or depot formulations of exenatide. Zero-order delivery eliminates the peak blood concentrations of exenatide typically observed with daily or twice-daily injections that appear to be associated with adverse reactions, e.g., frequent nausea, and the trough concentrations that may be associated with reduced efficacy. A further desirable feature of these DUROS® delivery devices is that they can be quickly and easily removed in a doctor's office to terminate drug administration in the event of adverse drug reaction or any event requiring cessation of treatment.

EXAMPLE 2

Phase 1b Clinical Trial Data for Continuous Delivery of Exenatide

A Phase 1b clinical trial was designed as a multi-center, randomized, open-label study with three sites and a total of 44 subjects. The Phase 1b clinical trial was designed and conducted to evaluate the safety and tolerability of continuous subcutaneous delivery of unmodified, synthetic exenatide having the amino acid sequence of exendin-4 via DUROS® delivery devices (ITCA 650) in subjects with inadequately controlled type 2 diabetes mellitus. In this study, osmotic delivery devices were implanted subcutaneously in the abdominal area under the abdominal skin.

In the study, subjects were randomized to receive doses of 10 mcg/day, 20 mcg/day, 40 mcg/day, or 80 mcg/day of ITCA 650. There were 10-12 subjects per group for each of four dose groups. Treatment was for 28 days with a 7-day follow-up period. Thus, this was a 29-day study that corresponded to a total of 28 days of treatment.

A. Demographics of Study Group

Inclusion/exclusion criteria were as follows: subjects were 30-70 years of age and diagnosed as having type 2 diabetes mellitus for greater than 6 months prior to screening. Subjects had inadequately controlled type 2 diabetes mellitus but were on stable treatment regimens of diet and exercise alone or in combination with metformin monotherapy, TZD monotherapy, or metformin plus TZD combination therapy. Subjects' hemoglobin A1c (HbA1c) levels were greater than or equal to 6.5% and less than or equal to 10%. Subjects had fasting plasma glucose of less than 270 mg/dL and fasting C-peptide of greater than 0.8 ng/ml.

The following 4 dose groups were investigated: Group 1, 10 mcg/day exenatide delivered by DUROS® delivery devices; Group 2, 20 mcg/day exenatide delivered by DUROS® delivery devices; Group 3, 40 mcg/day exenatide delivered by DUROS® delivery devices; and Group 4, 80 mcg/day exenatide delivered by DUROS® delivery devices.

The demographics of the study groups are presented in Table 1.

TABLE 1

|  | Group 1 | Group 2 | Group 3 | Group 4 |
|---|---|---|---|---|
| Age (years) | | | | |
| Mean | 56.4 | 57.4 | 52.1 | 56.7 |
| Range | 44-68 | 47-70 | 37-67 | 49-63 |
| Sex (M/F) | 8/4 | 7/4 | 4/6 | 7/4 |
| Weight (kg) | | | | |
| Mean | 95.7 | 94.3 | 88.5 | 89.5 |
| Range | 75.5-130.2 | 55.7-120.4 | 56.1-125.8 | 58.1-130.3 |
| HbA1c (%) | | | | |
| Mean | 7.7% | 7.9% | 7.4% | 7.4% |
| Range | 6.5-10.2 | 6.7-9.8 | 6.5-9.4 | 6.6-9.4 |
| Previous Treatment: | | | | |
| Diet & Exercise | 8.3% | | 20.0% | 36.4% |
| Metformin | 91.7% | 90.9% | 80.0% | 45.4% |
| Metformin + TZD | | 9.1% | | 18.2% |

The disposition of the subjects in the study is presented in Table 2.

TABLE 2

|  | Group 1 | Group 2 | Group 3 | Group 4 |
|---|---|---|---|---|
| n | 12 | 11 | 10 | 11 |
| Completed the Study | 11 (92%) | 11 (100%) | 10 (100%) | 7 (64%) |
| Subjects Discontinued | 1 (8%) | 0 (0%) | 0 (0%) | 4 (36%) |
| Adverse Events | 1 | 0 | 0 | 1 |
| Withdrew Consent | 0 | 0 | 0 | 3 |

B. Pharmacodynamic Data

The following pharmacodynamic measurement data were obtained from the study of exenatide delivered by DUROS® delivery devices.

Figure 1:
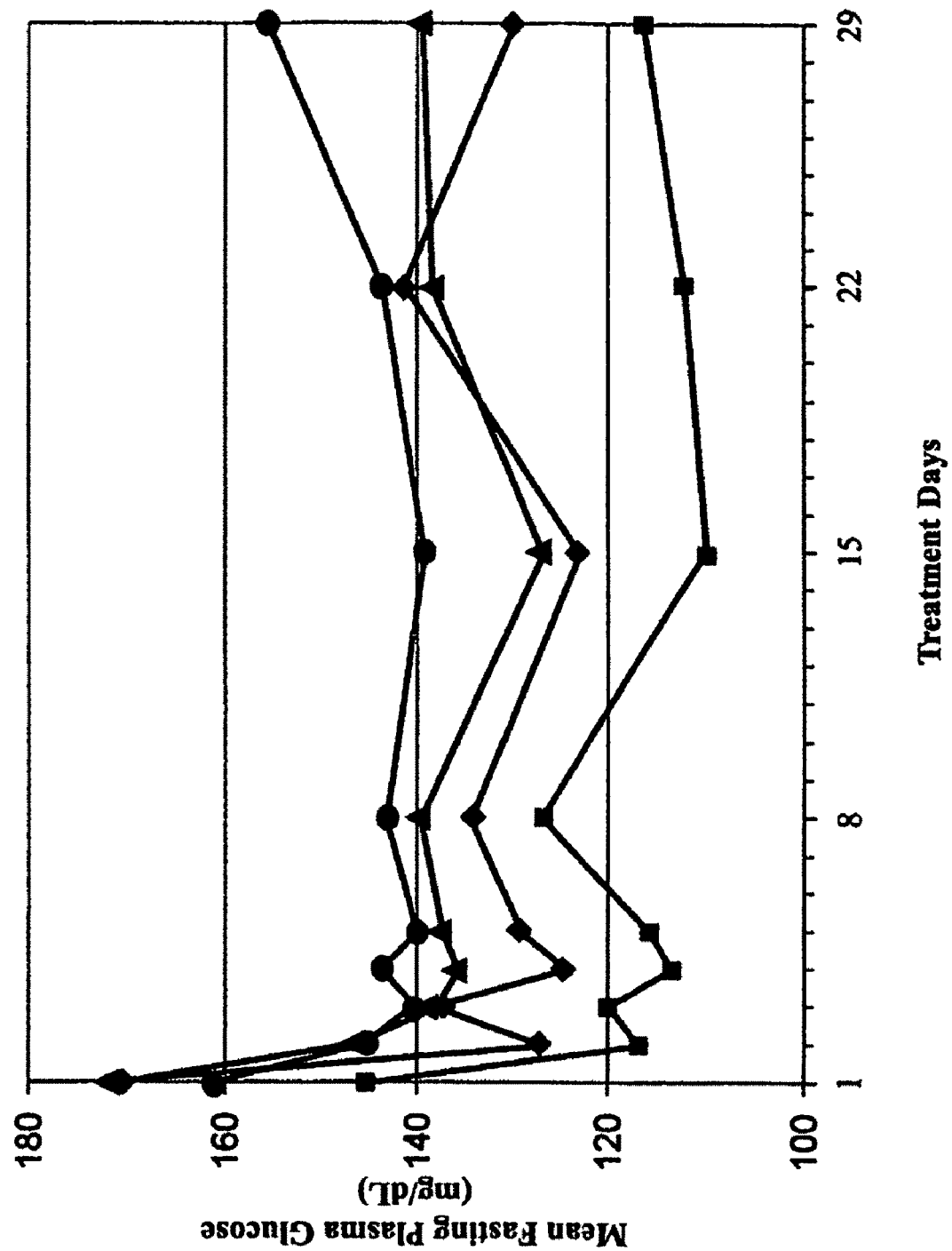
FIG. 1 presents the data from a randomized, open-label 29-day study of continuous subcutaneous delivery of exenatide using an osmotic delivery device. The figure shows fasting plasma glucose concentration versus time over 28 days of treatment. In the figure, the vertical axis is the Mean Fasting Plasma Glucose (mg/dL) and the horizontal axis is Treatment Days. Closed circles show data points for an osmotic device delivering 10 mcg/day. Closed triangles show data points for an osmotic device delivering 20 mcg/day. Closed diamonds show data points for an osmotic device delivering 40 mcg/day. Closed squares show data points for an osmotic device delivering 80 mcg/day.

Fasting plasma glucose (determined by standard methods) decreased within 24 hours (FIG. 1) following initiation of treatment (i.e., implantation of the DUROS® delivery devices) and was significantly different from baseline to endpoint in the 20 mcg/day group, the 40 mcg/day group, and the 80 mcg/day group as shown in Table 3. In Table 3 the data are shown from the randomized, open-label 29-day study of continuous subcutaneous delivery of exenatide using an osmotic delivery device. The table shows the change in fasting plasma glucose concentrations at the end of the 28-day treatment for osmotic devices delivering 10 mcg/day, 20 mcg/day, 40 mcg/day, and 80 mcg/day. Mean values in the table are given in mg/dL units. The decreases in fasting plasma glucose concentrations for the osmotic devices delivering 20 mcg/day, 40 mcg/day, and 80 mcg/day were statistically significant.

Accordingly, in one embodiment, the present invention relates to methods of and osmotic devices comprising exenatide for use in methods of treating type 2 diabetes mellitus by continuous delivery of exenatide wherein substantial steady-state delivery of the exenatide at therapeutic concentrations is achieved within a time period of about 7 days or less, preferably about 2 days or less, and more preferably about 1 day or less, after implantation of the osmotic delivery device in the subject. In a related embodiment the invention provides a significant decrease in fasting plasma glucose concentration, relative to the fasting plasma glucose concentration before implantation, achieved after implantation of the osmotic delivery device in the subject within a time period of about 7 days or less, preferably about 2 days or less, and more preferably about 1 day or less, after implantation of the osmotic delivery device in the subject.

TABLE 3

|  | Mean ± S.D. | p-value |
|---|---|---|
| 10 mcg/day | −5.6 ± 34.33 | 0.5175 |
| 20 mcg/day | −31.2 ± 24.20 | 0.0039 |
| 40 mcg/day | −42.0 ± 33.16 | 0.0003 |
| 80 mcg/day | −28.8 ± 32.25 | 0.0014 |

Treatment with exenatide delivered by DUROS® delivery devices at 20 mcg/day, 40 mcg/day and 80 mcg/day resulted in clinically and significant mean reductions in two-hour post-prandial glucose from pre-treatment to endpoint as shown in Table 4. An obvious dose-response relationship was observed. Measurement of reductions in two-hour post-prandial glucose was performed by standard methods. In Table 4 the data show the change in 2-hour postprandial glucose concentrations at the end of the 28-day treatment for osmotic devices delivering 10 mcg/day, 20 mcg/day, 40 mcg/day, and 80 mcg/day. Mean values in the table are given in mg/dL units. The decreases in 2 hour postprandial glucose concentrations for the osmotic devices delivering 20 mcg/day, 40 mcg/day, and 80 mcg/day were statistically significant.

TABLE 4

|  | Mean ± S.D. | p-value |
|---|---|---|
| 10 mcg/day | −16.3 ± 24.78 | 0.1699 |
| 20 mcg/day | −34.7 ± 32.39 | 0.0135 |
| 40 mcg/day | −47.1 ± 70.45 | 0.0012 |
| 80 mcg/day | −69.6 ± 44.35 | <0.0001 |

Glucose AUC (area under the curve) and the ratio of endpoint over pre-treatment was significantly different from baseline AUC in the 20 mcg/day group, the 40 mcg/day group, and the 80 mcg/day group; there was a trend toward reduction in these parameters at the 10 mcg/day dose. AUC calculations were performed by standard methods.

Figure 2:
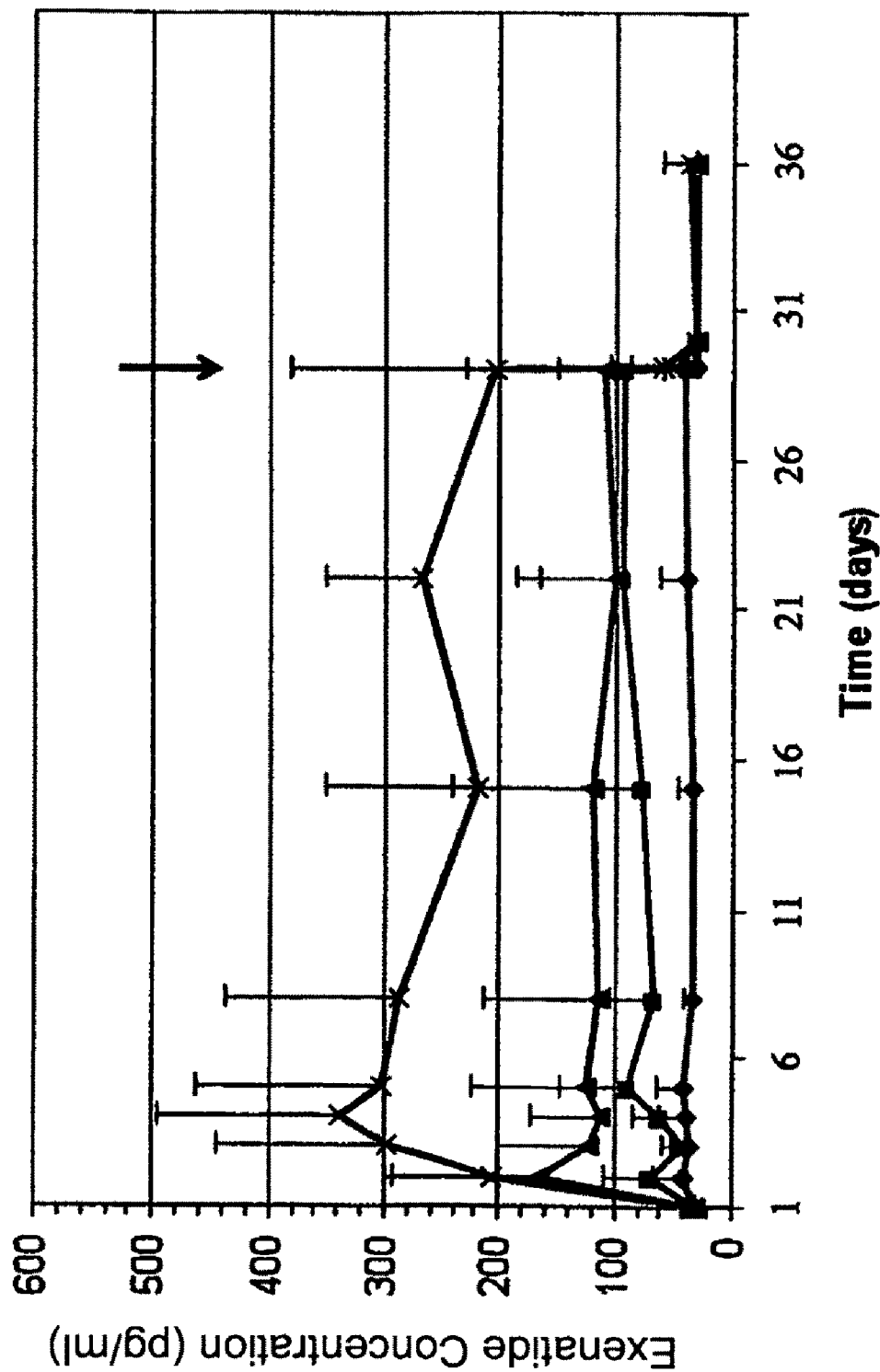
FIG. 2 presents the data from a randomized, open-label 29-day study of continuous subcutaneous delivery of exenatide using an osmotic delivery device. The figure shows pharmacokinetic data related to plasma exenatide concentration versus time over 28 days of treatment ending on day 29 and at 7 days following removal. In the figure, the vertical axis is the Exenatide Concentration (pg/ml) and the horizontal axis is Time (days). Closed diamonds show data points for an osmotic device delivering 10 mcg/day. Closed squares show data points for an osmotic device delivering 20 mcg/day. Closed triangles show data points for an osmotic device delivering 40 mcg/day. "X"s show data points for an osmotic device delivering 80 mcg/day. On day 29, removal of the osmotic delivery device and the accompanying drop in plasma exenatide concentration is indicated with a vertical arrow.

After implantation of the DUROS® delivery devices, exenatide plasma concentrations rose to the steady-state exposure concentration within 24-48 hours and were maintained throughout the treatment period (FIG. 2). Following removal of the DUROS® delivery devices, exenatide concentrations fell to undetectable concentrations within 24 hours (FIG. 2). Exenatide was detected using a radioimmunoassay. Accordingly, in one embodiment, the present invention relates to methods of and osmotic devices comprising exenatide for use in methods of treating type 2 diabetes mellitus by continuous delivery of exenatide that provide the capability to terminate the continuous delivery such that the concentration of exenatide is substantially undetectable in a blood sample from the subject after termination of continuous delivery in less than about 72 hours, preferably less than about 24.

HbA1c (as shown in Table 5) and fructosamine levels were significantly different from baseline to endpoint in the all treatment groups. Hb1Ac and fructosamine determinations were made by standard methods. In Table 5 the data are shown from the randomized, open-label 29-day study of continuous subcutaneous delivery of exenatide using an osmotic delivery device. The table shows the change in HbA1c at day 29 (relative to day 1 of the study; i.e., the initiation of continuous delivery) for osmotic devices delivering 10 mcg/day, 20 mcg/day, 40 mcg/day, and 80 mcg/day. Mean values in the table are change in HbA1c plus or minus the standard deviation (S.D.). The decreases in HbA1c for all osmotic devices (i.e., delivering 10 mcg/day, 20 mcg/day, 40 mcg/day, and 80 mcg/day) were statistically significant.

TABLE 5

| Dose | Mean Change in HbA1c ± S.D. | p-value |
| --- | --- | --- |
| 10 mcg/day | −0.54 ± 0.39 | 0.0010 |
| 20 mcg/day | −0.62 ± 0.31 | <0.0001 |
| 40 mcg/day | −0.45 ± 0.31 | 0.0013 |
| 80 mcg/day | −0.73 ± 0.36 | 0.0018 |

Body weight decreased in all treatment groups and was significantly different from baseline to endpoint in the 80 mcg/day group (Table 6). In Table 6 the data are shown from the randomized, open-label 29-day study of continuous subcutaneous delivery of exenatide using an osmotic delivery device. The table shows the change in body weight at the end of the 28-day treatment for osmotic devices delivering 10 mcg/day, 20 mcg/day, 40 mcg/day, and 80 mcg/day. Mean values in the table are given in dilograms (kg).

TABLE 6

| Dose | Mean ± S.D. | p-value |
| --- | --- | --- |
| 10 mcg/day | −0.27 ± .91 | 0.3415 |
| 20 mcg/day | −0.28 ± 1.51 | 0.5485 |
| 40 mcg/day | −1.13 ± 1.60 | 0.0524 |
| 80 mcg/day | −3.09 ± 2.13 | 0.0086 |

Figure 3:
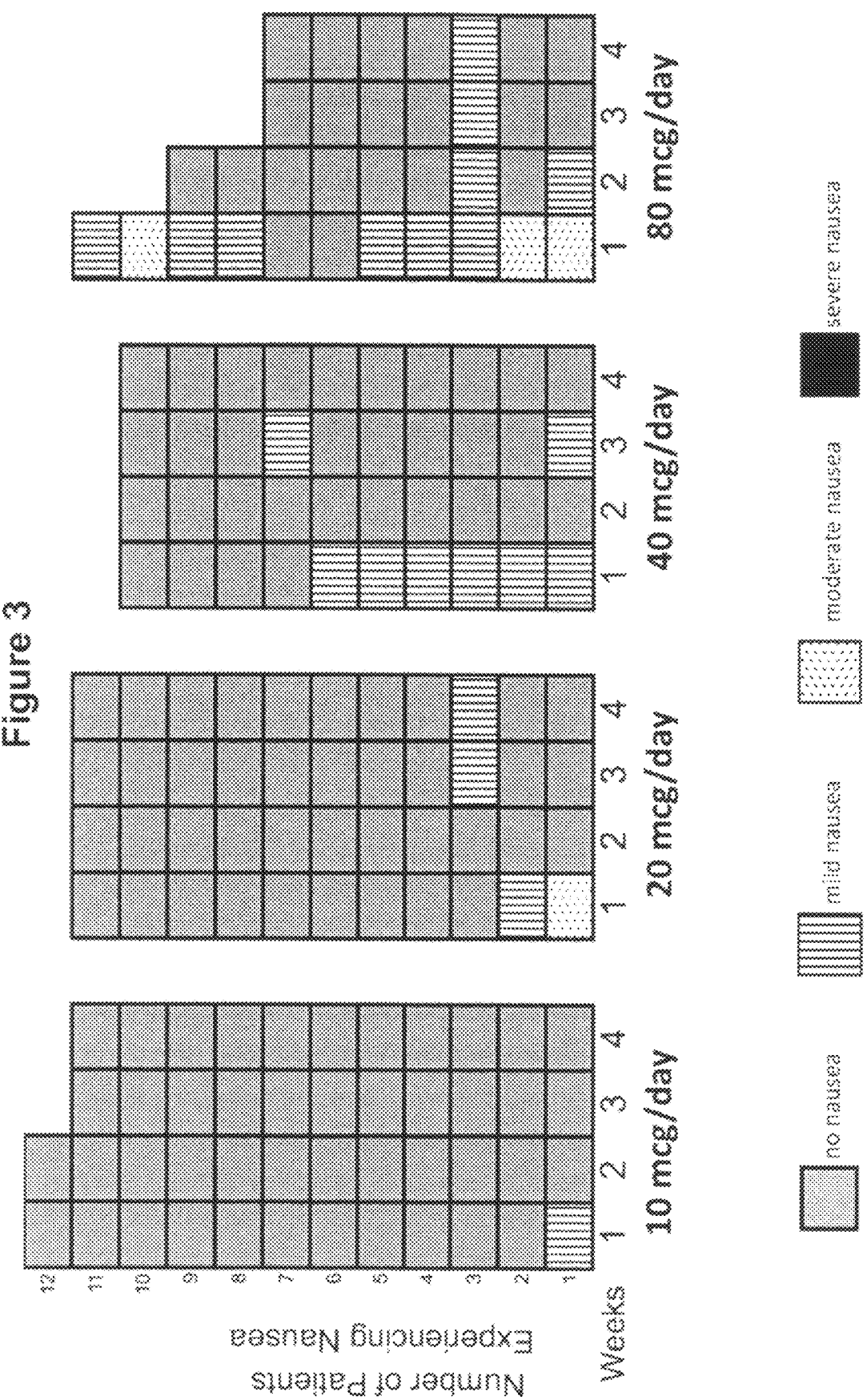
FIG. 3 presents the data from a randomized, open-label 29-day study of continuous subcutaneous delivery of exenatide using an osmotic delivery device. The figure shows nausea versus time in individual subjects for osmotic devices delivering 10 mcg/day, 20 mcg/day, 40 mcg/day, and 80 mcg/day. The vertical axis is the Number of Patients (subjects) Experiencing Nausea, the horizontal axis for each concentration of exenatide being delivered is presented in Weeks. The degree of nausea is given below the figure as no nausea (light grey), mild nausea (vertical lines), moderate nausea (stippling), and severe nausea (black).

While there was an apparent dose-response relationship with respect to gastrointestinal adverse events (nausea and vomiting), these effects occurred early after implantation of the device(s) and abated within the first week in most subjects. The data for nausea versus time in individual subjects is presented in FIG. 3.

In summary, therapy with exenatide delivered using DUROS® delivery devices at doses of 10, 20, and 40 mcg/day was well tolerated for 28 days of treatment. Steady-state concentrations of exenatide were rapidly achieved and maintained throughout the course of treatment. Removal of the DUROS® delivery devices provided rapid termination of treatment and exenatide concentrations fell to undetectable concentrations within 24 hours. Significant decreases in fasting plasma glucose and 2-hour post-prandial glucose were observed within 1-5 days and were maintained throughout the 28-day treatment period in the 20, 40, 80 mcg/day dose groups. Significant decreases in HbA1c were observed in all treatment groups. Body weight decreased in all treatment groups.

Treatment of subjects having type 2 diabetes mellitus with the DUROS® delivery devices providing 10 mcg/day, 20 mcg/day, 40 mcg/day, and 80 mcg/day was safe and well-tolerated; no clinically significant treatment-associated trends in safety, vital signs, or physical examination findings were observed. While there was an apparent dose-response relationship with respect to gastrointestinal adverse events (nausea and vomiting), these effects appeared to occur early (within the first week) after implantation of the device(s) and tended to abate with time.

These data demonstrated that DUROS® delivery devices providing continuous delivery of exenatide offered the following benefits: highly effective control of glucose; reduction in frequency, severity, and persistence of side effects; elimination of need for self-injection; significant weight loss; and 100% compliance with prescribed therapy. Further advantages for treatment of type 2 diabetes mellitus with these devices were the ability to rapidly achieve steady-state therapeutic concentrations of exenatide in a subject after implantation; the ability to provide long-term steady-state delivery of exenatide; the ability to provide a significant decrease in fasting plasma glucose concentration (relative to the fasting plasma glucose concentration before implantation of the osmotic device); and the capability of quickly terminating treatment if desirable.

EXAMPLE 3

Phase 2 Clinical Trial Data for Continuous Delivery of Exenatide

A Phase 2 clinical trial was designed as a multi-center randomized, open-label study with 50 sites and a total of 155 subjects. The Phase 2 study was designed and conducted to compare the efficacy, safety and tolerability of treatment with continuous subcutaneous delivery of unmodified, synthetic exenatide having the amino acid sequence of exendin-4 via DUROS® delivery devices (ITCA 650) versus twice-daily injections of unmodified, synthetic exenatide having the amino acid sequence of exendin-4 in subjects with inadequately controlled, metformin-treated type 2 diabetes mellitus. In the study, subjects were initially randomized to receive either 20 or 40 mcg/day of ITCA 650 for 12 weeks or twice-daily (BID) exenatide injections at 5 mcg BID for 4 weeks followed by 10 mcg BID for 8 weeks. Subsequently, subjects were randomized to receive 20, 40, 60 or 80 mcg/day of ITCA 650 for an additional 12 weeks. In this study, osmotic delivery devices (ITCA 650) were implanted subcutaneously in the abdominal area under the abdominal skin.

There were approximately 50 subjects per group for each of three groups as follows: Group 1, a group treated with implanted osmotic delivery devices of the present invention that delivered 20 mcg/day; Group 2, a group treated with implanted osmotic delivery devices of the present invention that delivered 40 mcg/day; and Group 3, a group treated with twice-daily exenatide injections at 5 mcg BID for 4 weeks followed by 10 mcg BID for 8 weeks. An overview of the study design is presented in FIG. 5. The extension phase was weeks 13-24 and the groups were randomized 1:1 to continuous delivery of exenatide as indicated in the figure. At the beginning of the extension phase for each subject, any implanted osmotic delivery device was removed and an osmotic delivery device providing continuous delivery of exenatide at the assigned dose was implanted. For example, if a subject was initially in Group 1 being treated by continuous delivery of exenatide at 20 mcg/day and was being increased to a dose of 60 mcg/day, then at the beginning of the extension phase the osmotic device delivering 20 mcg/day was removed and a new device delivering 60 mcg/day was implanted. For subjects initially being treated by injection, the injections were discontinued and osmotic delivery devices were implanted at the beginning of the extension phase. The study was completed on 15 Jul. 2010.

Accordingly, results of the Phase 2 study allow evaluation of the safety and efficacy of treatment using continuous delivery of exenatide versus exenatide twice-daily injections in type 2 diabetes mellitus over a 13-24 week treatment period. Further, the study allows evaluation of treatment dose escalation by continuous delivery of exenatide and the ability to transition subjects from treatment with exenatide twice-daily injections to treatment by continuous delivery.

A. Demographics of Study Group

Inclusion/exclusion criteria were as follows. Subjects were 18-70 years of age and diagnosed as having type 2 diabetes mellitus for greater than 6 months prior to screening. Subjects had inadequately controlled type 2 diabetes mellitus but were on stable treatment regimens of diet and exercise alone or in combination with metformin monotherapy. Subjects' HbA1c levels were greater than or equal to 7.0% and less than or equal to 10%. Subjects had fasting plasma glucose of less than 240 mg/dL and a body/mass index (BMI) of less than or equal to 40 kg/m$^2$.

The demographics of the study groups are presented in Table 7.

TABLE 7

|  | Group 1 | Group 2 | Group 3 |
|---|---|---|---|
| N (sample size) | 51 | 51 | 53 |
| Age (years) | 54.0 | 53.3 | 53.8 |
| Gender (M/F) | 25/26 | 23/28 | 29/24 |
| Duration of Diabetes (years) | 6.2 | 8.4 | 5.2 |
| HbA1c (%) | 7.9 | 8.0 | 8.0 |
| Weight (kg) | 93.5 | 91.5 | 93.4 |
| BMI (kg/m$^2$) | 33.5 | 31.8 | 33.0 |

The disposition of the subjects in the study at 12 weeks is presented in Table 8.

TABLE 8

|  | Group 1 N (%) | Group 2 N (%) | Group 3 N (%) | Total N (%) |
|---|---|---|---|---|
| Randomized and treated | 51 | 51 | 53 | 155 |
| Completed treatment | 47 (92.2) | 48 (94.1) | 47 (88.7) | 142 (91.6) |
| Early Withdrawal | 4 (7.8) | 3 (5.9) | 6 (11.3) | 13 (8.4) |
| Withdrew Consent | 2 (3.9) | 1 (2.0) | 2 (3.8) | 5 (3.2) |
| Adverse Event | 1 (2.0) | 2 (3.9) | 2 (3.8) | 5 (3.2) |
| Other | 1 (2.0) | 0 (0.0) | 2 (3.8) | 3 (1.9) |

B. Pharmacodynamic Data (i) Data at Week 12

The following pharmacodynamic measurement data were obtained from this Phase 2 clinical study of exenatide.

The changes in HbA1c after 12 weeks of treatment are presented in Table 9.

TABLE 9

|  | Sample Size | Baseline HbA1c % | Week 12 HbA1c % | Change in HbA1c |
|---|---|---|---|---|
| Group 1 | n = 47 | 7.90 | 6.94 | −0.96* |
| Group 2 | n = 47 | 8.00 | 6.96 | −1.04* |
| Group 3 | n = 47 | 8.01 | 7.19 | −0.82* |

*$p < 0.001$ relative to baseline

The data demonstrated that after 12 weeks of treatment all groups showed a reduction in HbA1c from baseline to endpoint. Exenatide treatment by continuous delivery (Groups 1 and 2) provided better decreases in HbA1c than exenatide treatment by injection (Group 3). All decreases in HbA1c were statistically different at 12 weeks compared to baseline; but not between each other. The study was not powered to detect differences between groups.

Further analysis of the data showed that a higher percentage of subjects reached HbA1c less than or equal to 7% and less than or equal to 6.5% at 12 weeks when treated following the methods of the present invention using continuous delivery of exenatide from an osmotic delivery device versus twice-daily injection (Table 10).

TABLE 10

|  | Subjects (at or below 7% of Total) | Percent | Subjects (at or below 6.5% of Total) | Percent |
|---|---|---|---|---|
| Group 1 | 30 of 47 | 64 | 15 of 47 | 32 |
| Group 2 | 32 of 47 | 68 | 12 of 47 | 26 |
| Group 3 | 24 of 47 | 51 | 8 of 47 | 17 |

Body weight decreased in all treatment groups and was significantly different from baseline to endpoint after 12 weeks of treatment in all groups (Table 11).

TABLE 11

|  | Subjects | Mean Weight Loss (in kg) | Percent Change (%) |
|---|---|---|---|
| Group 1 | n = 47 | −0.8 ± 2.4** | −0.9 ± 2.7 |
| Group 2 | n = 48 | −2.0 ± 3.0* | −2.6 ± 3.5 |
| Group 3 | n = 47 | −1.3 ± 2.5* | −1.5 ± 2.8 |

*$p < 0.001$ relative to baseline
**$p < 0.05$ relative to baseline

Figure 6:
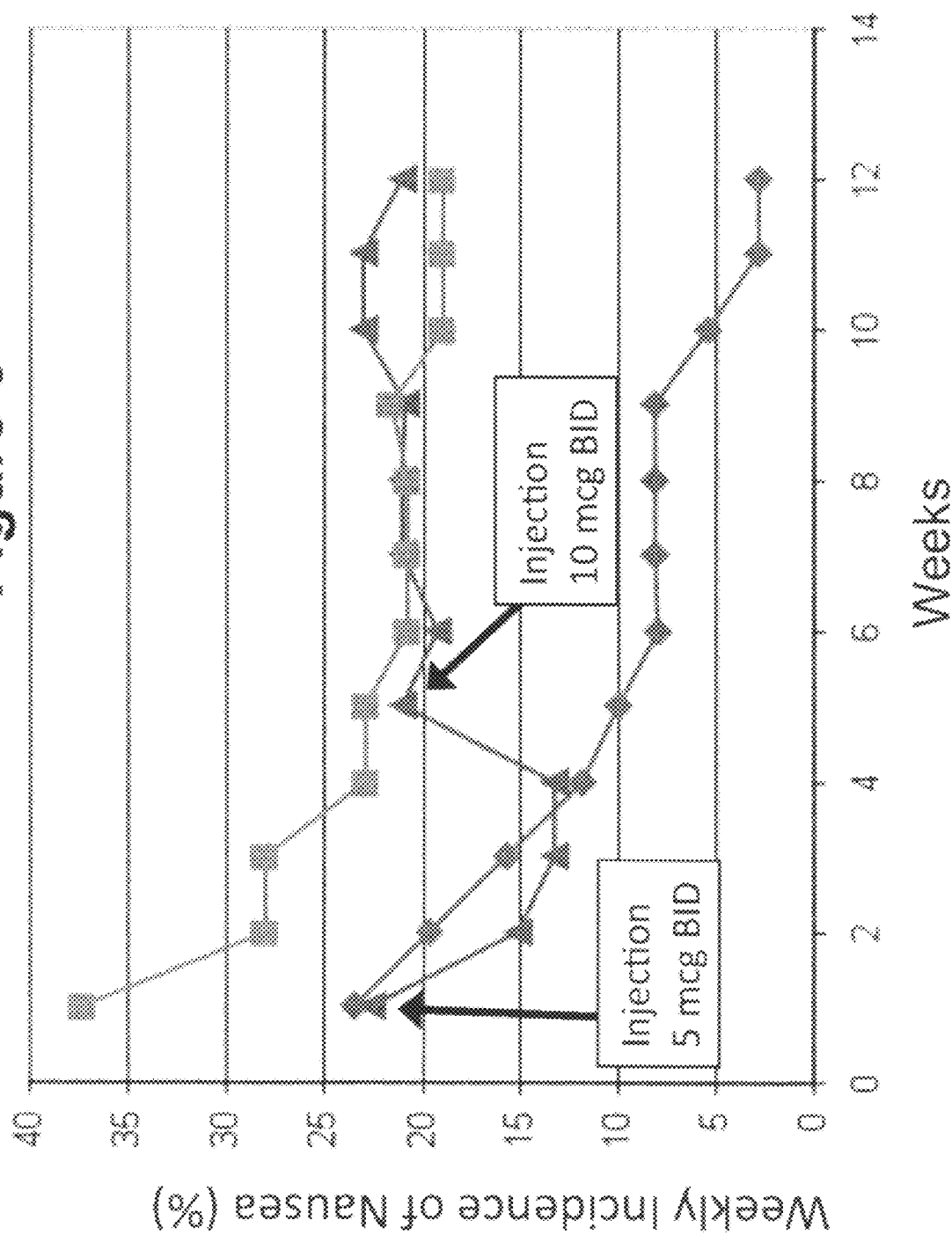
FIG. 6 presents the data for incidence of nausea over time for treatment by continuous delivery of exenatide (Groups 1 and 2) versus treatment by twice-daily injection with exenatide (Group 3). The vertical axis is the Weekly Incidence of Nausea (%) and the horizontal axis is the time of treatment in Weeks. In the figure, Group 1, treatment by continuous delivery of 20 mcg/day of exenatide, is represented by diamonds; Group 2, treatment by continuous delivery of 40 mcg/day of exenatide, is represented by squares; and Group 3, treatment by injection with 5 mcg BID (twice-daily injection) for 4 weeks (arrow approximately illustrates starting time point) followed by 10 mcg BID for 8 weeks (arrow approximately illustrates starting time point), is represented by triangles.

While there was an apparent dose-response relationship with respect to gastrointestinal adverse events (nausea and vomiting), these effects occurred early after implantation of the device(s) and typically abated within the several weeks in most subjects (FIG. 6). In FIG. 6 it can be seen that, when the dose of the twice-daily injections was increased from 5 mcg/day to 10 mcg/day, the incidence of nausea increased and remained higher than the with the initial treatment dosage level. That result was in contrast to the data seen with continuous delivery wherein the overall trend was toward a decreased incidence of nausea over time.

Referring to FIG. 6, the initial frequency of nausea with exenatide injections was above 20% at the starting dose of 5 mcg BID. At four weeks when the dose was increased to 10 mcg BID, the frequency of nausea increased again to greater than 20% and persisted at that rate for the remainder of the 12-week period.

With treatment at 20 mcg/day by continuous delivery, the initial frequency of nausea was about 25% and gradually decreased every week. Over the first four weeks, the frequency of nausea was similar to exenatide injections even though twice the amount of exenatide was being delivered. From week 6 onward, the frequency of nausea continued to fall and was less than 10% at the end of week 12. The duration of nausea was much less in the 20 mcg/day continuous delivery group with a mean duration of nausea of 17 days versus 47.7 days with exenatide injections.

At the higher dose of 40 mcg/day administered by continuous delivery, the frequency of nausea was higher but fell to a similar rate compared to exenatide injections from week six onward even though the amount of exenatide that the subject received was twice that of exenatide injections. Most of the nausea was mild to moderate.

The data in FIG. 6 demonstrate that delivery of 20 mcg/day by continuous delivery from an osmotic delivery device resulted in continuing improvement of nausea symptoms over the 12-week treatment period. Further, the data demonstrate that over time delivery of 40 mcg/day by continuous delivery from an osmotic delivery device resulted in no greater nausea than lower dose exenatide twice-daily injection. These data show improved tolerability of exenatide treatment using continuous delivery versus twice-daily injections of exenatide. Accordingly, in one embodiment, the present invention relates to methods of and osmotic devices comprising exenatide for use in methods of treating type 2 diabetes mellitus by continuous delivery of exenatide that provide improved tolerization to dose escalation of exenatide.

In addition, quality of life was assessed among study subjects at baseline and week 8 using the validated DM-SAT Quality of Life survey (Anderson, R T, et al., Diabetes Care 32:51 (2009)). Sixteen criteria were examined and subjects self-scored on a scale of 0-10. Comparisons of change were made from baseline across all treatment arms (n~50 subjects/arm) and an aggregate total score obtained from the 16 criteria. In addition, the 16 criteria were grouped by four subscales of well-being, lifestyle, medical control and convenience.

Figure 7:
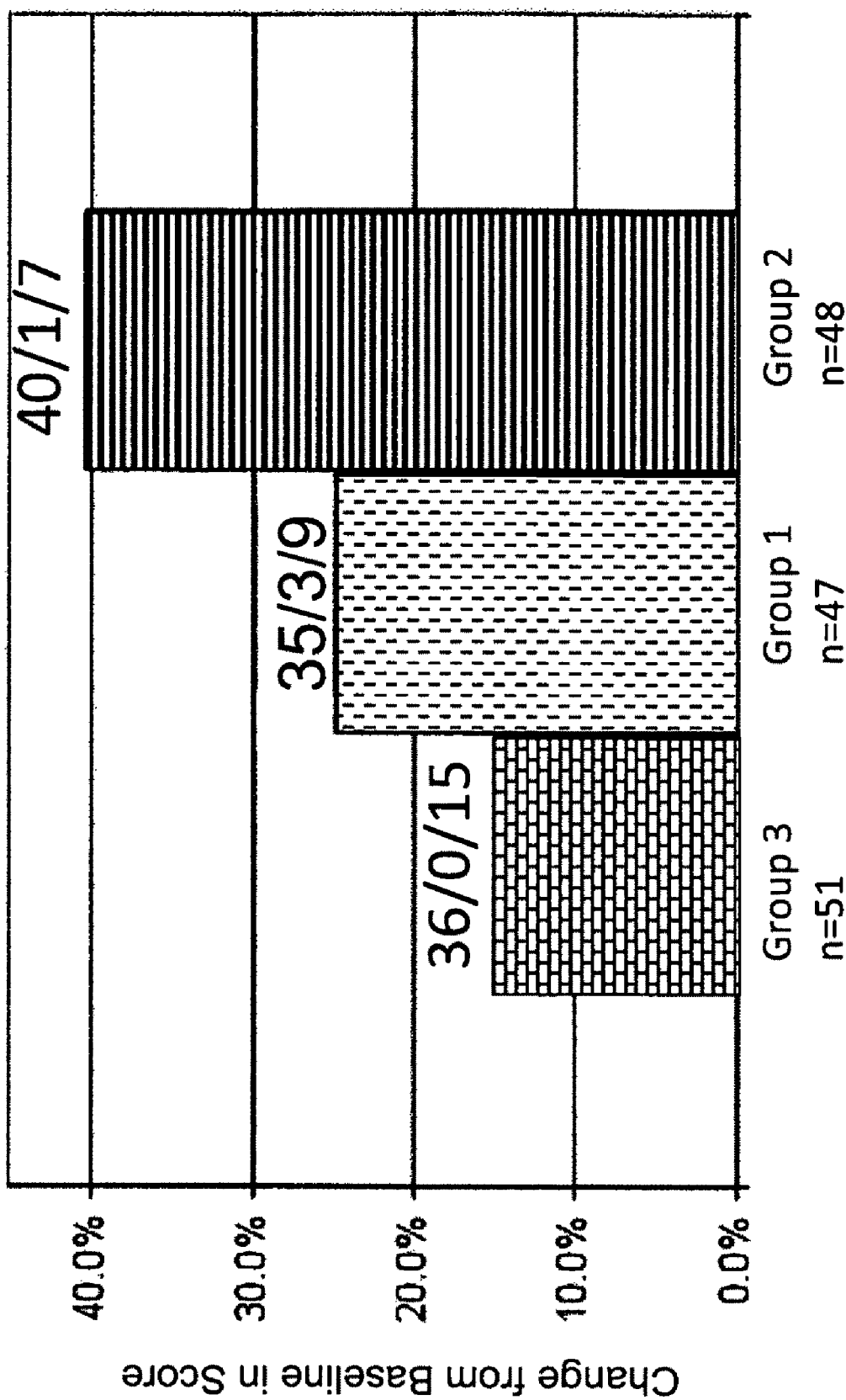
FIG. 7 presents data showing the percent change from baseline in overall Quality of Life (QOL) assessment at week 8. In the figure the numbers over the bar graphs represent the following: n with improved QOL score/n with stable QOL score/n with decreased QOL score, respectively; for Group 3, 36/0/15; for Group 1, 35/3/9; and for Group 2, 40/1/7. The vertical axis is the Change from Baseline in Score (%; the overall QOL score). The groups are arranged along the horizontal axis and the group sizes are provided under each group: Group 3, n=51; Group 1, n=47; and Group 2, n=48.

The data presented in FIG. 7 shows the percent change from baseline in the overall QOL assessment at week 8. In the figure the numbers over the bar graphs represent the following: n with improved QOL score/n with stable QOL score/n with decreased QOL score, respectively; for Group 3, 36/0/15; for Group 1, 35/3/9; and for Group 2, 40/1/7. The data indicated that on average subjects gave an overall higher QOL assessment to exenatide treatment when the treatment was provided by continuous delivery at 20 mcg/day (Group 1) and 40 mcg/day (Group 2) using an implanted osmotic delivery device versus when exenatide was administered by twice-daily injections (Group 3). For exenatide injections (Group 3), the QOL improvement was a little more than 10%. For Groups 1 and 2 the improvement in QOL was greater, from 20-30%. A greater fraction of the subjects receiving exenatide injections (Group 3) reported a decrease in QOL than either of the continuous delivery groups (Groups 1 and 2). These data demonstrated a significant advantage of the implanted osmotic delivery device over exenatide administration via injection in terms of reported quality of life for treated subjects.

Figure 8:
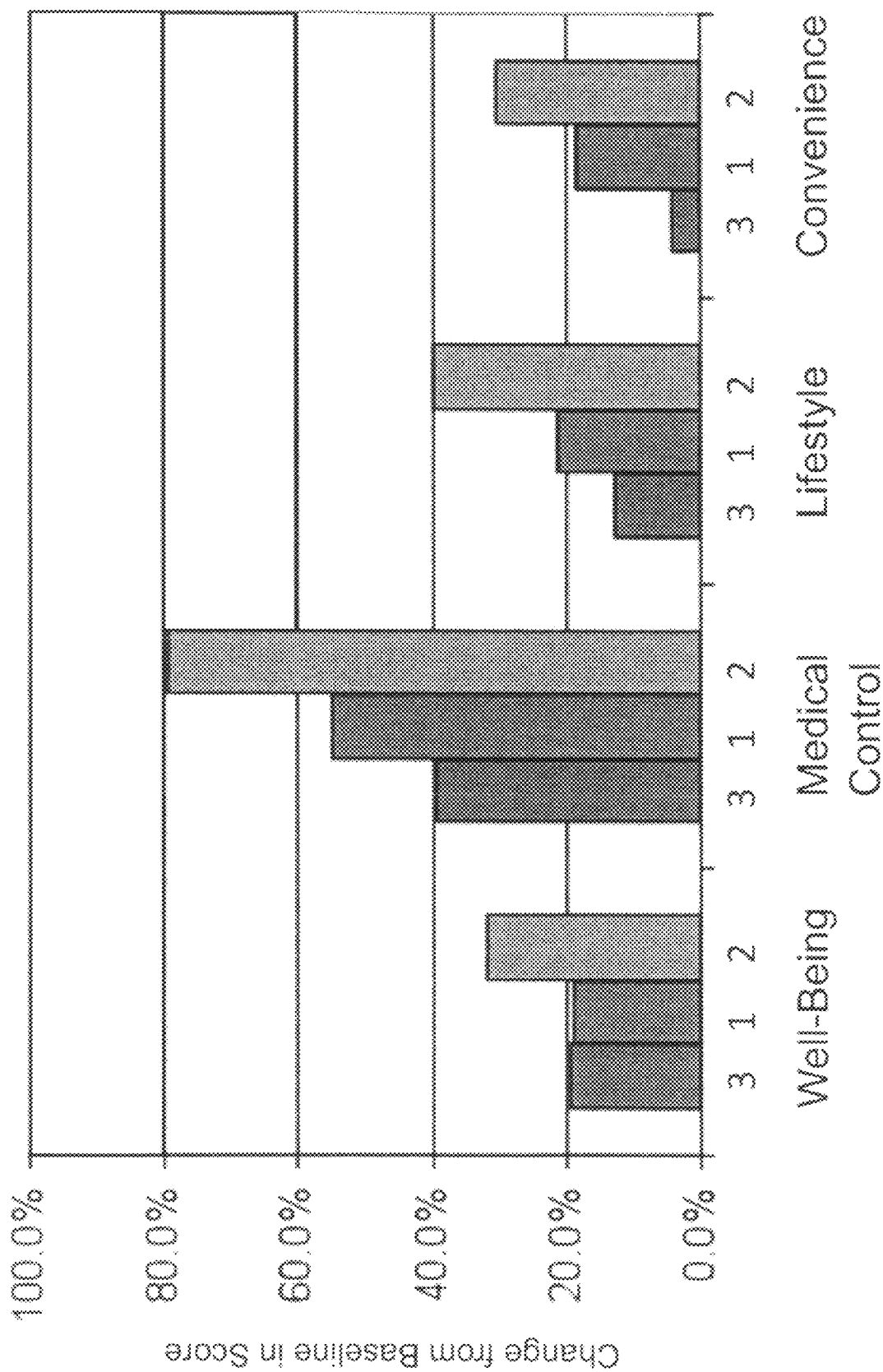
FIG. 8 presents data from a subscale analysis of QOL performed at week 8. The vertical axis is the percent Change from Baseline in Score for each of the four QOL subscales: Well-Being, Medical Control, Lifestyle, and Convenience. The four QOL subscales are arranged along the horizontal axis. In the figure, each bar of the graph is labeled with the Group number. Within each subscale, the bar graphs are arrayed in the following order: Group 3, Group 1, and Group 2.

Further, a subscale analysis of QOL was performed at week 8 and the percent changes from baseline are presented in FIG. 8. In the figure, the bars are labeled with the Group number, that is, Groups 3, 1, and 2, respectively. The data showed that subjects rated continuous delivery of exenatide using an osmotic pump as providing consistently higher QOL than exenatide administered by injection by each of the four subscales of well-being, medical control, lifestyle, and convenience. These data demonstrated a significant advantage of the implanted osmotic delivery device over exenatide administration via injection in terms of reported quality of life in each of the four subscales for treated subjects.

Treatment with exenatide by continuous delivery resulted in potential beneficial changes in other parameters relative to treatment with exenatide injections at week 12. For example, the change of low density lipoprotein cholesterol (LDL-C) values from baseline to week 8 were as shown in Table 12.

TABLE 12

| | Change in LDL from Baseline | Percent Change |
|---|---|---|
| Group 1 | −4.8 mg/dL | −1.63 |
| Group 2 | −5.4 mg/dL | −4.33 |
| Group 3 | +1.2 mg/dL | 15.26 |

LDL-C decreased 4.8 and 5.4 mg/dL with exenatide treatment by continuous delivery at 20 and 40 mcg/day, respectively, whereas it increased 1.2 mg/dL with exenatide treatment by injections. These data demonstrated a more favorable effect on reduction of LDL-C by treatment using continuous delivery of exenatide versus twice-daily injection.

Further, the change of seated systolic blood pressure values from baseline to week 8 were as shown in Table 13.

TABLE 13

| Group 1 | −3.6 mmHg |
|---|---|
| Group 2 | −6.8 mmHg |
| Group 3 | −4.2 mmHg |

Systolic blood pressure decreased 3.6 and 6.8 mmHg with exenatide treatment by continuous delivery at 20 and 40 mcg/day, respectively, and decreased 4.2 mmHg with exenatide treatment by injections. These data demonstrated that all treatment methods provided similar, favorable effect on reduction of systolic blood pressure by treatment using continuous delivery of exenatide and twice-daily injection.

(ii) Data at Week 20

Figure 9:
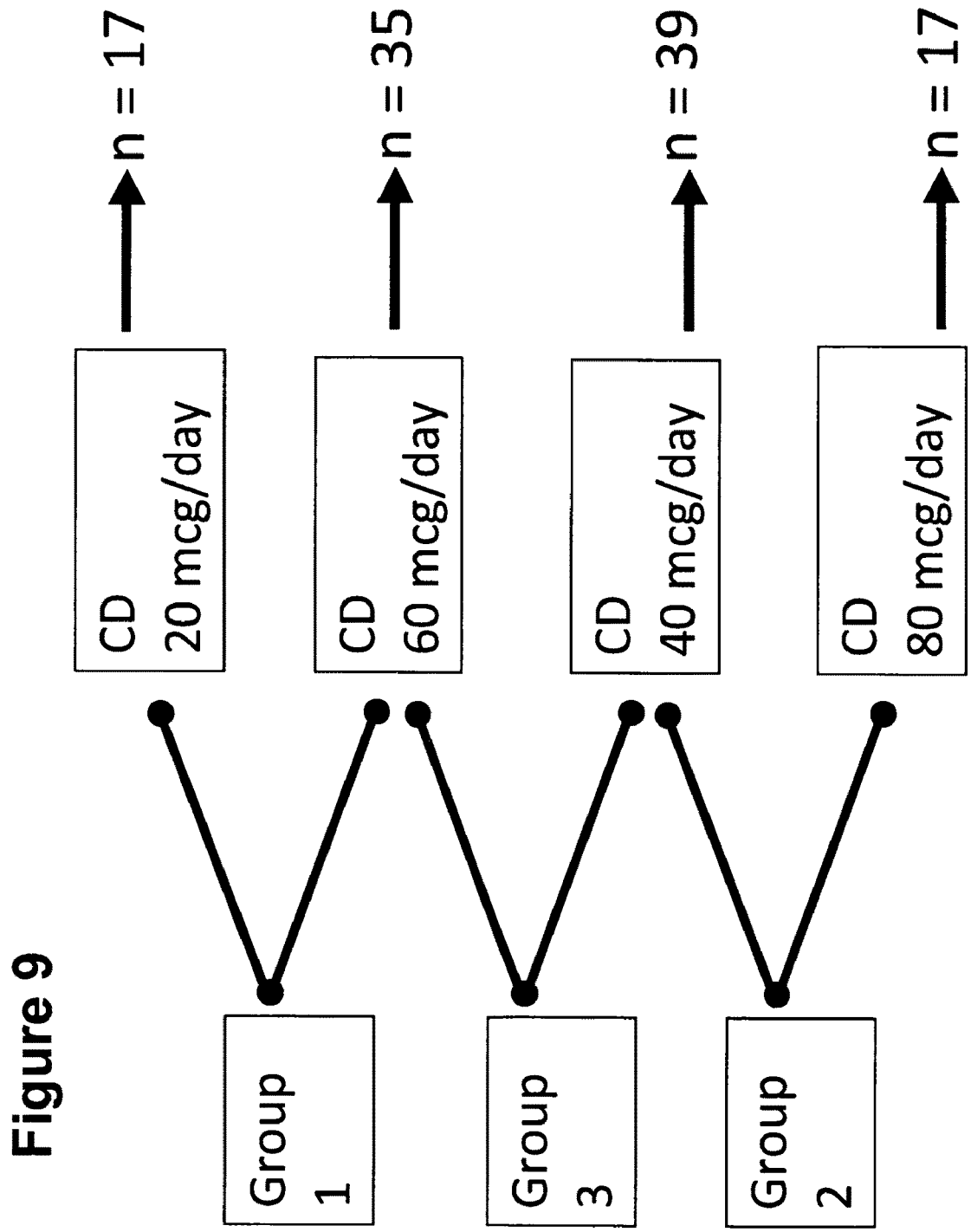
FIG. 9 presents an overview of the extension phase for subject status at week 20. In the figure, continuous delivery of exenatide at the indicated dosages is shown as "CD." The group sizes are presented next to the extension phase dosage. In the extension phase for weeks 13-24, subjects from each treatment group were randomized to receive continuous delivery of exenatide at 20, 40, 60 or 80 mcg/day. In the figure, Group 1 is treatment by continuous delivery of 20 mcg/day of exenatide for the first 12 weeks; Group 2 is treatment by continuous delivery of 40 mcg/day of exenatide for the first 12 weeks; and Group 3 is treatment by injection with 5 mcg BID (twice-daily) injection for 4 weeks followed by 10 mcg BID for 8 weeks for the first 12 weeks. The split in the group indicates the randomization of the group at week 12 and the boxes show the dosages for the dose escalation after week 12. The number in each group at week 20 is shown as "n."

Extension phase data for subject status at week 20 is presented in FIG. 9. In the extension phase for weeks 13-24, subjects from each treatment group were randomized to receive continuous delivery of exenatide at 20, 40, 60 or 80 mcg/day. The changes in HbA1c percent at week 20 of treatment are presented in Table 14.

TABLE 14

| Dosage Delivered by Continuous Delivery to Randomized Groups | Sample Size | Baseline HbA1c % | Week 20 HbA1c % | Change in HbA1c |
|---|---|---|---|---|
| 20 mcg/day | n = 17 | 7.88 | 7.03 | −0.85 |
| 40 mcg/day | n = 39 | 7.83 | 6.77 | −1.06 |
| 60 mcg/day | n = 35 | 8.06 | 6.79 | −1.27 |
| 80 mcg/day | n = 17 | 8.07 | 6.68 | −1.39 |

These data demonstrated that dose escalation to continuous delivery at the higher doses of 60-80 mcg/day resulted in further reduction in HbA1c relative to baseline. In addition, continued weight loss was observed.

The data presented in Table 15 show subjects reaching HbA1c treatment goals at 20 weeks. The data demonstrated continuing reduction of HbA1c in the randomized groups. Further, the data demonstrated that dose escalation resulted in more subjects reaching HbA1c treatment goals.

TABLE 15

| | Subjects (at or below 7% of Total) | Percent | Subjects (at or below 6.5% of Total) | Percent |
|---|---|---|---|---|
| 20 mcg/day | 10 of 20 | 50% | 4 of 20 | 20% |
| 40 mcg/day | 31 of 39 | 79% | 18 of 39 | 46% |
| 60 mcg/day | 28 of 38 | 74% | 18 of 38 | 47% |
| 80 mcg/day | 13 of 17 | 76% | 9 of 17 | 53% |

In summary, exenatide treatment by continuous delivery using an implantable osmotic delivery device at doses of 20 and 40 mcg/day was well tolerated over 12 weeks with robust glucose-lowering activity. HbA1c decreased by 0.96% and 1.04% with exenatide treatment by continuous delivery at doses of 20 and 40 mcg/day, respectively, compared to a decrease of 0.82% with exenatide injections. More subjects reached HbA1c treatment goals of 7% or 6.5% with exenatide treatment by continuous delivery than with exenatide injections. Weight loss was observed in all treatment groups. Despite receiving twice as much exenatide during the initial 4 weeks of treatment, nausea decreased progressively over the first six weeks with exenatide treatment by continuous delivery at 20 mcg/day compared to treatment with exenatide injections where nausea persisted from weeks 4-12 with a weekly incidence of ≥20%. Both doses of exenatide treatment by continuous delivery performed better than exenatide injections overall and in all four subscales (well-being, medical control, lifestyle, convenience) of a QOL survey conducted after 8 weeks of treatment.

In addition, dose escalation with exenatide treatment by continuous delivery at week 13 resulted in further reduction of HbA1c after 8 weeks of therapy. Subjects treated with exenatide treatment by continuous delivery at 60 mcg/day from weeks 13-20 had a decrease in HbA1c of 1.27% from baseline. Subjects treated with exenatide treatment by continuous delivery at 80 mcg/day from weeks 13-20 had a decrease in HbA1c of 1.39% from baseline.

(iii) Final Data at Completion of Phase 2 Study

The overall disposition of the subjects at completion of the study is presented in Table 16.

TABLE 16

| | Groups 1 and 2 | Group 3 |
|---|---|---|
| Weeks 1-12 | | |
| Completion Rate | 93% | 89% |
| Withdrawals due to nausea | 3.9% | 5.7% |

TABLE 16-continued

| | Groups 1 and 2 | Group 3 |
|---|---|---|
| Withdrawals prior to re-randomization | 8.4% | 6.4% |
| Completion Rate | 95% | NA* |
| Withdrawals due to nausea | <1% | NA* |

*NA—not applicable

In Table 16, "Weeks 1-12" presents the study disposition over the first treatment period. There was a very high completion rate, 93%, in the treatment groups providing continuous delivery (Groups 1 and 2). Groups 1 and 2 each had two subjects withdraw due to nausea, and Group 3 had three subjects withdraw due to nausea. In the table, "Withdrawals prior to re-randomization" are subjects that completed the first 12 weeks of treatment, but opted not to continue through the 12-week extension phase treatment period. No specific reasons were given for these withdrawals.

In Table 16, for "Weeks 13-24," all subjects were treated using continuous delivery from implanted osmotic delivery devices. This treatment period of the study had a very high completion rate. Only one subject withdrew because of nausea. This subject had been on exenatide injections and then received treatment by continuous delivery at 60 mcg/day. The subject noted nausea for five days and withdrew from study.

The changes in HbA1c percent for weeks 13-24 of treatment are presented in Table 17.

TABLE 17

| Dose Delivered by Continuous Delivery Weeks 13-24 (mcg/day) | Sample Size | Baseline HbA1c % | Week 12 HbA1c % | Week 24 HbA1c % | Change in HbA1c | Percent of Subjects who achieved HbA1c: ≤7% | ≤6.5% |
|---|---|---|---|---|---|---|---|
| 20 | n = 20 | 7.96 | 7.10 | 7.07 | −0.89* | 60% | 20% |
| 40 | n = 42 | 7.79 | 7.07 | 6.93 | −0.86* | 71% | 43% |
| 60 | n = 41 | 8.05 | 7.08 | 6.67 | −1.38* | 73% | 49% |
| 80 | n = 19 | 8.03 | 6.83 | 6.67 | −1.36* | 79% | 63% |

*$p < 0.0001$ relative to baseline

Figure 5:
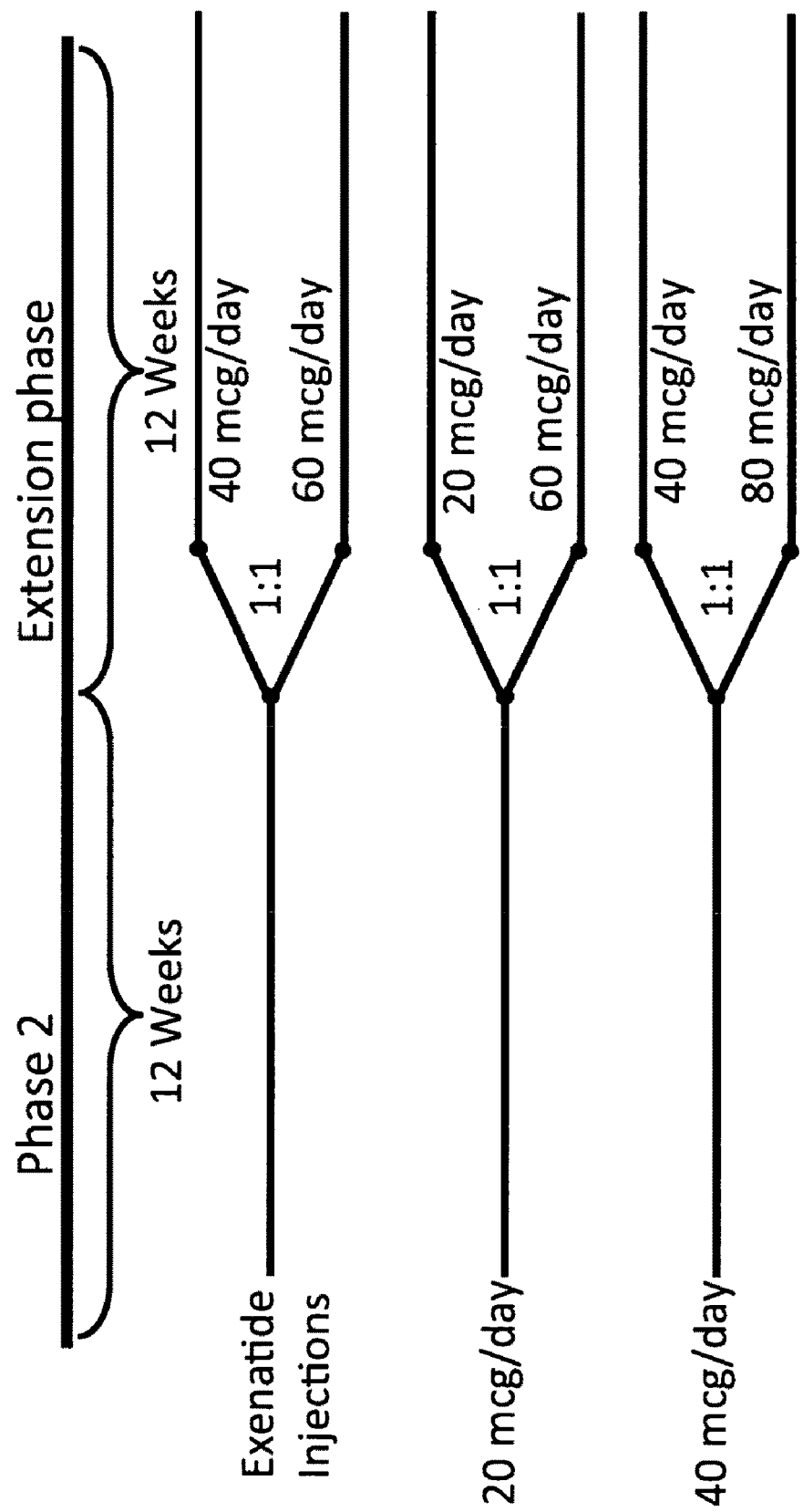
FIG. 5 presents an overview of a Phase 2 clinical study design. In the figure, the top line shows a timeline of the Phase 2 study (12 weeks) and the 12-week extension phase. The extension phase is weeks 13-24 and the groups were randomized 1:1 to continuous delivery of exenatide as indicated in the figure. Group 3, exenatide administered via injection, is the second line. The split in the line indicates the randomization of the group and the switch to continuous delivery at 40 mcg/day and 60 mcg/day. Group 1, exenatide administered using an osmotic delivery device to provide continuous delivery at 20 mcg/day, is the third line. The split in the line indicates the randomization of the group to continue 20 mcg/day or escalate to the elevated dosage of 60 mcg/day. Group 2, exenatide administered using an osmotic delivery device to provide continuous delivery at 40 mcg/day, is the fourth line. The split in the line indicates the randomization of the group to continue 40 mcg/day or escalate to the elevated dosage of 80 mcg/day.

In Table 17, the data given for Week 12 shows the average change in HbA1c values from initiation of treatment (baseline) to week 12 (the end of the first treatment period) for the subjects after randomization and before entry into the extension phase treatment period (weeks 13-24) (see FIG. 5). The data shown for Week 24 show the changes in HbA1c associated with each dose at the end of treatment by continuous delivery at the specified doses. After treatment with exenatide by continuous delivery, at 24 weeks further decreases in HbA1c were seen in all treatment groups. All of these reductions in HbA1c are statistically significant relative to the baseline and demonstrate that continued reduction of HbA1c can be obtained using continuous delivery of exenatide. For the two highest doses (i.e., 60 mcg/day and 80 mcg/day), both groups had a change of greater than 1.3% demonstrating that increasing the dose of exenatide administered by continuous delivery provided continued reduction in HbA1c over the treatment period. The percentage of subjects with HbA1c at 7% or less demonstrated good treatment outcome for all groups, with the greatest improvements seen at the higher doses (60 mcg/day, 73%; and 80 mcg/day, 79%). The study was not powered to detect differences between groups.

The reductions in HbA1c and the percent of subjects who achieved an HbA1c of less than 7% demonstrate the clinical value of treatment of subjects having type 2 diabetes mellitus using continuous delivery of exenatide over a range of different doses.

Further analysis of the HbA1c data from weeks 13-24 for subjects receiving continuous delivery of 60 mcg/day of exenatide showed that the higher the initial HbA1c baseline at the beginning of the extension phase treatment period the greater the reduction in HbA1c that was seen at the end of the extension phase treatment period (Table 18).

TABLE 18

| Subjects treated by continuous delivery of 60 mcg/day | Sample Size | Baseline HbA1c | Week 24 HbA1c | Change in HbA1c | Percent of Subjects achieving HbA1c of 7% or less |
|---|---|---|---|---|---|
| All Subjects | n = 41 | 8.05 | 6.67 | −1.38* | 73% |
| Subjects having a baseline HbA1c > 7.0 | n = 36 | 8.22 | 6.73 | −1.49* | 69% |
| Subjects having a baseline HbA1c ≧ 7.5 | n = 27 | 8.54 | 6.77 | −1.77* | 63% |

*p < 0.0001 relative to baseline

In Table 18, the "Baseline" is the mean HbA1c of the subjects at initiation of treatment at the beginning of the clinical study. For the 41 subjects who received treatment by continuous delivery of 60 mcg/day of exenatide from weeks 13-24, the mean HbA1c was 8.05% with a 1.38% drop after treatment. Of these 41 subjects, 36 subjects who had a baseline HbA1c of greater than 7 had a mean HbA1c of 8.22% with a 1.49% drop after treatment. Of the 41 subjects, 27 subjects who had a baseline HbA1c of greater than or equal to 7.5 had a mean HbA1c of 8.54% with an even bigger drop of 1.77% after treatment. These results further demonstrate that treatment of type 2 diabetes mellitus subjects using continuous delivery of exenatide provides desirable treatment outcome because continued improvement in HbA1c was seen over the treatment period and subjects with higher baselines at the beginning of the treatment period showed the desirable outcome of greater reductions in HbA1c than subjects with lower baselines.

Body weight decreased in all treatment groups and was significantly different from baseline to endpoint at 24 weeks of treatment in all groups (Table 19).

TABLE 19

| Dose Delivered by Continuous Delivery Weeks 13-24 (mcg/day) | Sample Size | Mean Weight Loss (in kg) | Percent Change (in %) |
|---|---|---|---|
| 20 | n = 20 | −0.8 | −0.85 |
| 40 | n = 42 | −3.6* | −4.0 |
| 60 | n = 41 | −3.1* | −3.4 |
| 80 | n = 19 | −3.5** | −3.8 |

*p < 0.0001 relative to baseline
**p < 0.01 relative to baseline

The lowest dose of 20 mcg/day had an average weight loss of 0.8 kg. All the higher doses had greater than 3 kg weight loss; the values were also statistically significant.

The data presented in FIG. 10 show the incidence of nausea over the treatment period of weeks 13-24. In the figure, the first time point (−1 week) shows the incidence of nausea the week prior to subject randomization for extension phase dosing. With continuous delivery of 20 mcg/day of exenatide, the incidence of nausea remained very low throughout the treatment period. With an increase in the continuous delivery dose from 20 mcg/day to 60 mcg/day of exenatide, there was an increase in the incidence of nausea; but treatment was well-tolerated as described below. When subjects receiving 20 mcg/day of exenatide as twice-daily injections were treated in the extension phase using continuous delivery of 60 mcg/day of exenatide, the incidence of nausea was much higher reaching 50% during the fourth week after dose escalation. Thus, treatment with twice-daily exenatide injections was not helpful in tolerization of subjects to the gastrointestinal side effects of increased doses of exenatide, whereas treatment using continuous delivery of exenatide did provide tolerization of subjects to the gastrointestinal side effects of increased doses of exenatide. Accordingly, in one embodiment, the present invention relates to methods of and osmotic devices comprising exenatide for use in methods of treating type 2 diabetes mellitus by continuous delivery of exenatide that provide improved tolerization to dose escalation of exenatide.

Regarding the treatment being well tolerated, for subjects treated using continuous delivery of 20 to 60 mcg/day of exenatide, there were no withdrawals from treatment, six subjects reported nausea during weeks 13-24, and four reported nausea during weeks 1-12. There were no reports of vomiting. Four of these subjects were at sites participating in a continuation phase allowing treatment from weeks 25-48 and all four elected to continue treatment using continuous delivery. Further, 85% of all eligible subjects in all of the treatment groups elected to continue treatment in the continuation phase.

In addition, changes in subjects' QOL score in the extension phase of the study were evaluated essentially as described above. With reference to FIG. 9, the data presented in FIG. 11 presents changes from baseline for QOL scores based on subsequent randomization to two treatment groups (i.e., continuous delivery of either 40 mcg/day or 60 mcg/day exenatide) in the extension phase of the original subjects in Group 3 (twice-daily injection of exenatide). QOL for original subjects of Group 3 who were randomized to continuous delivery of 40 mcg/day were compared using their QOL data from week 8 and their QOL data obtained at week 20. QOL data for original subjects of Group 3 who were randomized to continuous delivery of 60 mcg/day were compared using their QOL data from week 8 and their QOL data obtained at week 20. As can been seen from the data in FIG. 11, subjects who switched from twice-daily exenatide injections (Group 3) to continuous delivery from an implanted osmotic device (at doses of 40 mcg/day or 60 mcg/day of exenatide) reported substantial increase in QOL scores.

With reference to FIG. 9, the data presented in FIG. 12 presents changes from baseline for QOL scores based on the original subjects of Group 1 (continuous delivery of 20 mcg/day of exenatide) who were subsequently randomized to continuous delivery at 60 mcg/day in the extension phase, and the original subjects of Group 2 (continuous delivery of 40 mcg/day of exenatide) who were subsequently randomized to continuous delivery of 80 mcg/day in the extension phase. QOL data for these subjects were compared using their QOL data from week 8 and their QOL data obtained at week 20. As can be seen from the data presented in FIG. 12, the QOL scores for subjects treated by continuous delivery who had their dose increased 2-3 fold in the extension phase maintained higher QOL scores (relative to those treated by twice-daily injection, compare to FIG. 7 and FIG. 8) even at the higher doses. Thus, treatment using continuous delivery from implanted osmotic delivery devices was compared to treatment outcomes for twice-daily and once-weekly exenatide injections, as well as oral anti-diabetic agents.

FIG. 13 to FIG. 21 present comparative treatment data for the drugs and treatment methods set forth in Table 20.

TABLE 20

| Treatment Designation in Figures | Drug/ Dosing Schedule | Source of Data/Studies |
|---|---|---|
| Treatment A | Exenatide, twice-daily injection (5 mcg per injection) | DeFronzo RA, et al., Diabetes Care 28(5): 1092-1100 (2005) |
| Treatment B | Exenatide, once-weekly injection (2 mg/week) | Bergenstal RM, et al., Lancet 376(9739): 431-439 (2010) |
| Treatment C | Liraglutide, once-daily injection (1.2 or 1.8 mg/day) | Pratley RE, et al., Lancet 375(9724): 1447-1456 (2010) |
| Treatment D | Taspoglutide, once-weekly injection (10 or 20 mg/week) | Rosenstock J, et al., American Diabetes Association (ADA) 70th Scientific Sessions, Orlando FL, Abstract 62-OR (2010); Nauck M, et al., American Diabetes Association (ADA) 70th Scientific Sessions, Orlando FL, Abstract 60-OR (2010); Bergenstal R, et al., American Diabetes Association (ADA) 70th Scientific Sessions, Orlando FL, Abstract 58-OR (2010). |
| Treatment E | Exenatide, continuous delivery of 20 mcg/ day or 60 mcg/day using an implantable osmotic device (i.e., embodiments of the present invention) | The Phase 2 clinical trial described herein. |
| Treatment F | Sitagliptin, taken orally once a day (100 mg/day) | Bergenstal RM, et al., Lancet 376(9739): 431-439 (2010) |
| Treatment G | Pioglitazone, taken orally once a day (15 mg, 30 mg, or 45 mg) | Bergenstal RM, et al., Lancet 376(9739): 431-439 (2010) | the present invention provides methods of and osmotic devices comprising exenatide for use in methods of treating type 2 diabetes mellitus by continuous delivery of exenatide that provide improved QOL to subjects being treated with exenatide.

In summary, treatment of type 2 diabetes mellitus using continuous delivery of exenatide from implanted osmotic devices provides glycemic control at all doses. Subjects started on continuous delivery of 20 mcg/day followed by dose escalation to 60 mcg/day experienced superior tolerability and reductions in HbA1c and weight. In addition, improvement in subject-reported QOL was observed at all exenatide doses administered by continuous delivery versus twice-daily injection of exenatide. A greater improvement in QOL was observed in subjects treated by continuous delivery of exenatide versus twice-daily exenatide injection. Also, marked QOL improvement was seen in subjects switching from twice-daily exenatide injection to continuous delivery using implanted osmotic delivery devices.

The methods and implantable osmotic delivery devices of the present invention provide unique potential for long-term optimal treatment of type 2 diabetes mellitus because it is the first incretin mimetic therapy that ensures subject adherence and eliminates the need self injection.

C. Comparative Treatment Data

This example discusses comparisons of different therapeutic approaches for the treatment of type 2 diabetes mellitus among subjects on a metformin-only treatment background. The data from the above-described Phase 2 clinical study of Liraglutide and taspoglutide are both peptides and incretin mimetics. Sitagliptin is a small molecule DPP-4 inhibitor. Pioglitazone is a TZD and a potent agonist for peroxisome proliferator-activated receptor-gamma.

The comparative data presented in FIG. 13 demonstrates that treatment using the methods and osmotic delivery devices of the present invention for continuous delivery of exenatide (Treatment E) provided the best reduction in HbA1c over the treatment periods of the studies. Accordingly, the continuous delivery of exenatide as described herein provided superior HbA1c reductions relative to exenatide administered by injection either twice-daily (Treatment A) or once-weekly (Treatment B), as well as superior reductions in HbA1c relative to treatment by two different incretin mimetics, liraglutide (once-daily injection; Treatment C) and taspoglutide (once-weekly injection; Treatment D).

The comparative data presented in FIG. 14 demonstrates that treatment using the methods and osmotic delivery devices of the present invention for continuous delivery of exenatide (Treatment E) provided excellent HbA1C drop despite a lower baseline at study initiation than treatment with sitagliptin (Treatment F), pioglitazone (Treatment G), or once-weekly injections of exenatide (Treatment B). In the Bergenstal R M, et al., study about one-third of subjects had a HbA1c of greater than 9%; however, in the experiments described herein using continuous delivery of 20 mcg/day or 60 mcg/day of exenatide, there was only one subject above having a HbA1c above 9. This explains the difference in the mean HbA1c baselines.

The comparative data presented in FIG. 15 demonstrates that treatment using the methods and osmotic delivery devices of the present invention for continuous delivery of exenatide (Treatment E) provided an increased reduction in HbA1c despite lower baselines when compared to once-weekly administration of exenatide. Unlike the Phase 2 clinical trial described herein, which was conducted entirely in the United States, the Bergenstal R M, et al., study was conducted in the United States, Mexico and India. This geographic distribution resulted in an enrollment of subjects who were less well controlled on metformin monotherapy and who entered the study with higher baseline HbA1c levels. The mean baseline HbA1c in subjects treated with once-weekly injections of exenatide (Treatment B) from the Bergenstal R M, et al., study, and one-third of the subjects enrolled in the Bergenstal R M, et al., study had baseline HbA1c levels higher than 9%. Analyzing only subjects from Treatment E who had higher baseline HbA1c levels demonstrated that the absolute drop in HbA1c is higher among subjects on treatment using the methods and osmotic delivery devices of the present invention for continuous delivery of exenatide (Treatment E). This suggests that the continuous delivery of exenatide as described by the present invention may outperform once-weekly injection of exenatide in similar study populations who have high baseline HbA1c.

The comparative data presented in FIG. 16 demonstrates that treatment using the methods and osmotic delivery devices of the present invention for continuous delivery of exenatide (Treatment E) provided robust reductions of HbA1c relative to treatment with once-weekly injections of exenatide (Treatment B). The HbA1c changes from the Bergenstal R M, et al., study were further analyzed between subjects with baseline HbA1c less than 9% and subjects with baseline HbA1c greater than or equal to 9%. Comparing the results of exenatide treatment by continuous delivery of the present invention (Treatment E) to treatment using once-weekly exenatide injection (Treatment B) following the same analysis showed that HbA1c reductions following the treatment methods of the present invention are as good or better than those seen using once-weekly exenatide injection.

The same comparison of results of the treatment methods of the present invention (Treatment E) with the results from subjects on sitagliptin from the Bergenstal R M, et al., study suggested an even greater advantage for the continuous delivery of exenatide to provide better reductions in HbA1c relative to sitagliptin (FIG. 17). These results support use of the osmotic delivery devices of the present invention for treatment providing continuous delivery as a preferred add-on therapy to metformin relative to DPP-4 inhibitors (e.g., sitagliptin). Further, when comparing subjects with HbA1c of less than or equal to 9% from the Bergenstal R M, et al., study to similar subjects from the Phase 2 clinical study described herein, it was seen that the treatment methods and osmotic devices of the present invention provide much more substantial reductions in HbA1c (FIG. 18).

Similarly, the same comparison of results of the treatment methods of the present invention (Treatment E) with the results from subjects on pioglitazone from the Bergenstal R M, et al., study suggested that the continuous delivery of exenatide provides greater reductions in HbA1c relative to pioglitazone (FIG. 19). These results support use of the osmotic delivery devices of the present invention for treatment providing continuous delivery as a preferred add-on therapy to metformin relative to TZDs (e.g., pioglitazone). Further, when comparing subjects with HbA1c of less than or equal to 9% from the Bergenstal R M, et al., study to similar subjects from the Phase 2 clinical study described herein, it was seen that the treatment methods and osmotic devices of the present invention provided much more substantial reductions in HbA1c (FIG. 20).

Further, FIG. 21 presents a comparison of weight loss obtained using sitagliptin (Treatment F), pioglitazone (Treatment G), or once-weekly injections of exenatide (Treatment B) to treatment using the methods and osmotic delivery devices of the present invention for continuous delivery of exenatide (Treatment E). The data presented in the figure demonstrate that, when comparing the treatments, the methods and osmotic delivery devices of the present invention provide the best weight loss.

Finally, all the subjects enrolled into the Phase 2 clinical study were receiving only metformin therapy for treatment of their type 2 diabetes mellitus before initiation of the study. The metformin doses were not modified over the course of the Phase 2 clinical study. Subjects were treated using continuous delivery of 20 mcg/day or 40 mcg/day of exenatide for 12 weeks or were randomized to a group that was treated by twice-daily, self-injected exenatide (4 weeks at 5 mcg BID followed by 10 mcg BID for 8 weeks).

Metformin is known to cause certain gastrointestinal adverse events such as diarrhea, nausea and vomiting. Subjects treated by continuous administration of 20 mcg/day of exenatide and whose dose of exenatide was then escalated to higher doses of continuously administered exenatide had fewer adverse gastrointestinal side effects than those subjects who received exenatide injections at 20 mcg/day and were then escalated to higher doses of continuously administered exenatide.

Thus, subjects who started on exenatide continuous delivery therapy were better tolerized to the effects of the combination of exenatide given with metformin than those who initially received exenatide injections given with metformin. Accordingly, using continuous administration of exenatide from an osmotic delivery device is the best exenatide treatment option for combination with metformin therapy relative to twice-daily injections of exenatide.

The Phase 2 clinical trial data illustrates that exenatide treatment by continuous delivery provided the following potential benefits: highly effective control of glucose; reduction in the gastrointestinal side effects relative to treatment by injection; elimination of the need for self-injection; substantial weight-loss; and 100% compliance to prescribed therapy.

EXAMPLE 4

Phase 3 Clinical Trial Study Designs for Continuous Delivery of Exenatide

The following study designs are presented for illustrative purposes only and other Phase 3 clinical trial designs are feasible as will be understood by one of ordinary skill in the art.

A. First Study Design

One Phase 3 clinical trial study design is as follows. The study is a randomized, double-blind, placebo-controlled study. The study group includes subjects with type 2 diabetes mellitus treated with metformin, TZD, sulfonylurea, and any combination of metformin, TZD or sulfonylurea. Subjects have an HbA1c of greater than 7%. Subjects are randomized 1:2 between placebo versus continuous delivery of unmodified, synthetic exenatide having the amino acid sequence of exendin-4 using implantable osmotic delivery devices, respectively. There are a total of 300 subjects. The dose of exenatide used for continuous delivery is selected based on the results at completion of the Phase 2 study including tolerability, glucose-lowering activity, and weight loss activity. The dose for continuous delivery will likely include 3 months of treatment with 20 mcg/day and 3 months of treatment with 60 mcg/day. Randomization is stratified based on sulfonylurea use and HbA1c (less than 9% versus greater than or equal to 9%).

The data to be obtained and assessed includes the following: HbA1c (primary endpoint), fasting plasma glucose, weight, lipids, blood pressure, adiponectin, C-reactive protein (CRP), calcitonin, and amylase/lipase. In addition QOL assessment will be performed.

There will be either an open-label or a blinded 26-week extension phase for long-term treatment using continuous delivery from implanted osmotic delivery devices.

B. Second Study Design

A second Phase 3 clinical trial study design is as follows. The study is a randomized, double-blind, placebo-controlled Phase 3 study having a 26-week blinded study and a mandatory 26-week extension. The study group includes subjects with type 2 diabetes mellitus treated with diet and exercise and/or an oral treatment selected from the following: a TZD, a sulfonylurea, a TZD and metformin, a sulfonylurea and metformin, or a TZD and a sulfonylurea; with the exclusion of metformin-only treatment. The exclusion of metformin-only treatment provides a larger sulfonylurea subset for safety evaluation. Inclusion criteria for subjects include stable maximum dose background therapy. There will be no exclusion for cardiovascular risk.

Subjects have an HbA1c of greater than or equal to 7.5%. Subjects are randomized 1:2 between placebo versus continuous delivery of unmodified, synthetic exenatide having the amino acid sequence of exendin-4 using implantable osmotic delivery devices, respectively. There are a total of 375 subjects. The doses used for continuous delivery of exenatide include: Group A (n=150), 13 weeks of treatment with 20 mcg/day followed by 13 weeks of treatment with 60 mcg/day; Group B (n=150), 13 weeks of treatment with 20 mcg/day followed by 13 weeks of treatment with 40 mcg/day; and, Group C (n=75), the placebo control group, 13 weeks of treatment with placebo followed by 13 weeks of treatment with placebo. The primary endpoint of the study is week 26. There is a mandatory blinded extension phase with treatment as follows: Group A, 26 weeks of treatment with 60 mcg/day; Group B, 26 weeks of treatment with 40 mcg/day; and Group C, 26 weeks of treatment with 20 mcg/day.

The data to be obtained and assessed includes the following: HbA1c (primary endpoint), fasting plasma glucose, weight, lipids, blood pressure, adiponectin, C-reactive protein (CRP), calcitonin, and amylase/lipase. In addition QOL assessment will be performed.

Further modifications of this study may include the following. Addition of a randomized, double-blind, placebo-controlled phase 3 clinical trial, wherein the study group includes subjects with type 2 diabetes mellitus treated with DPP-4 inhibitors or TZDs as add-ons to metformin treatment (i.e., subjects are treated with a DPP-4 inhibitor and metformin or a TZD and metformin). The study is a 26-week blinded study with a mandatory 26-week extension. The study is placebo-controlled with placebos for both continuous delivery of exenatide and for orally administered drugs. The total number of this group of subjects is approximately 500. The treatment doses include: Group A (n=170), 13 weeks of treatment by continuous delivery of exenatide at 20 mcg/day followed by 13 weeks of treatment with 60 mcg/day; Group B (n=170), 26 weeks of treatment with 45 mg/day pioglitazone (a TZD); and, Group C (n=170), 26 weeks of treatment with 100 mg/day sitagliptin (a DPP-4 inhibitor). The primary endpoint of the study is week 26. There is a mandatory blinded extension phase with treatment as follows: Group A, 26 weeks of treatment with continuous delivery of exenatide at 60 mcg/day; Group B, 26 weeks of treatment with 45 mg/day pioglitazone; and Group C, 26 weeks of treatment with 100 mg/day sitagliptin.

The purpose of this study is to demonstrate superiority of treatment with continuous delivery of exenatide using osmotic delivery devices to treatment with DPP-4 inhibitors and TZDs.

As is apparent to one of skill in the art, various modification and variations of the above embodiments can be made without departing from the spirit and scope of this invention. Such modifications and variations are within the scope of this invention.

What is claimed is:

1. A method of treating type 2 diabetes mellitus in a subject in need of treatment, comprising:
   providing continuous delivery of exenatide from an osmotic delivery device, the osmotic delivery device comprising
      an impermeable reservoir comprising interior and exterior surfaces and first and second open ends,
      a semi-permeable membrane in sealing relationship with the first open end of the reservoir,
      an osmotic engine within the reservoir, the osmotic engine adjacent the semi-permeable membrane,
      a piston adjacent the osmotic engine, wherein the piston forms a movable seal with the interior surface of the reservoir, the piston divides the reservoir into
   a first chamber and a second chamber, the first chamber containing the osmotic engine,
      a suspension formulation contained in the second chamber, the suspension formulation comprising a particle formulation and a vehicle formulation, wherein
         the particle formulation comprises particles comprising exenatide in particles of less than 10 microns in diameter, and
         the vehicle formulation comprises a solvent and a polymer, wherein the solvent is selected from the group consisting of benzyl benzoate, lauryl lactate, and lauryl alcohol, and the polymer is polyvinylpyrrolidone, the vehicle formulation having a viscosity between about 10,000 poise and about 20,000 poise at 37° C., and
      a diffusion moderator that defines a delivery orifice inserted in the second open end of the reservoir, the diffusion moderator adjacent the suspension formulation;
   wherein (i) substantial steady-state delivery of the exenatide at a therapeutic concentration is achieved within a time period of 5 days or less after implantation of the osmotic delivery device in the subject, and (ii) the substantial steady-state delivery of the exenatide from the osmotic delivery device is continuous over an administration period of at least about 3 months at a mcg/day dose of exenatide selected from the group consisting of about 10 mcg/day, about 20 mcg/day, about 30 mcg/day, about 40 mcg/day, about 60 mcg/day, and about 80 mcg/day.

2. The method of claim 1, wherein substantial steady-state delivery of exenatide at therapeutic concentrations is achieved after implantation of the osmotic delivery device in the subject within a time period selected from the group consisting of about 4 days or less, about 3 days or less, and about 2 days or less, and about 1 day or less.

3. The method of claim 1, wherein the substantial steady-state delivery of exenatide from the osmotic delivery device is continuous over an administration period selected from the group consisting of at least about 3 months to about a year, at least about 4 months to about a year, at least about 5 months to about a year, at least about 6 months to about a year, at least about 8 months to about a year, and at least about 9 months to about a year.

4. The method of claim 1, further comprising providing a significant decrease in the subject's fasting plasma glucose concentration after implantation of the osmotic delivery device in the subject, relative to the subject's fasting plasma glucose concentration before implantation of the osmotic delivery device, within a number of days selected from the group consisting of about 7 days or less, about 6 days or less, about 5 days or less, about 4 days or less, about 3 days or less, about 2 days or less, and about 1 day or less.

5. The method of claim 4, wherein the significant decrease in the subject's fasting plasma glucose concentration is achieved, relative to the subject's fasting plasma glucose concentration before implantation of the osmotic device, within about 1 day of implantation of the osmotic delivery device in the subject.

6. The method of claim 4, wherein the significant decrease in fasting plasma glucose is maintained over the administration period.

7. The method of claim 1, further comprising termination of continuous delivery by removal of the osmotic delivery device from the subject such that the concentration of exenatide is substantially undetectable in a blood sample from the subject after termination of continuous delivery in a number of hours selected from the group consisting of less than 72 hours, less than 48 hours, less than 24 hours, and less than 12 hours.

8. The method of claim 7, wherein exenatide is detected by a radioimmunoassay.

9. The method of claim 1, wherein the reservoir comprises titanium or a titanium alloy.

10. The method of claim 1, wherein the method further comprises a first continuous administration period of exenatide at a first mcg/day dose that is followed by a second continuous administration period providing a dose escalation of exenatide to a second mcg/day dose, wherein the second mcg/day dose is greater than the first mcg/day dose.

11. The method of claim 10, wherein the first mcg/day dose is delivered by the osmotic delivery device and the second mcg/day dose is delivered by a second osmotic delivery device.

12. The method of claim 10, wherein the method further comprises at least one more continuous administration period providing a dose escalation of exenatide to a higher mcg/day dose relative to the second mcg/day dose.

13. The method of claim 10, wherein the first mcg/day dose followed by the second mcg/day dose for continuous delivery are selected from the group consisting of: about 10 mcg/day followed by about 20 mcg/day; about 10 mcg/day followed by about 40 mcg/day; about 10 mcg/day followed by about 60 mcg/day; about 10 mcg/day followed by about 80 mcg/day; about 20 mcg/day followed by about 40 mcg/day; about 20 mcg/day followed by about 60 mcg/day; about 20 mcg/day followed by about 80 mcg/day; about 40 mcg/day followed by about 60 mcg/day; about 40 mcg/day followed by about 80 mcg/day; and about 60 mcg/day followed by about 80 mcg/day.

14. The method of claim 1, wherein the subject is a human.

* * * * *

UNITED STATES PATENT AND TRADEMARK OFFICE
CERTIFICATE OF CORRECTION

PATENT NO. : 8,298,561 B2
APPLICATION NO. : 12/924175
DATED : October 30, 2012
INVENTOR(S) : Thomas R. Alessi et al.

Page 1 of 3

It is certified that error appears in the above-identified patent and that said Letters Patent is hereby corrected as shown below:

In the Specifications

In col. 18, line 2, delete "polyvinvylpyrrolidone", and insert -- polyvinylpyrrolidone --, therefor.

In col. 18, line 5, delete "polyvinvylpyrrolidone", and insert -- polyvinylpyrrolidone --, therefor.

In col. 20, line 59, delete "polyvinvylpyrrolidone", and insert -- polyvinylpyrrolidone --, therefor.

In col. 20, line 62, delete "polyvinvylpyrrolidone", and insert -- polyvinylpyrrolidone --, therefor.

In col. 28, lines 38-39, delete "NaCl, $N_2SO4$, $NaHCO_3$, KCl, $KH_2PO4$, $CaCl_2$, and $MgCl_2$.", and insert -- NaCl, $Na_2SO_4$, $NaHCO_3$, KCl, $KH_2PO4$, $CaCl_2$, and $MgCl_2$. --, therefor.

In col. 39, lines 11-13, delete

"
TABLE 1

|  | Group 1 | Group 2 | Group 3 | Group 4 |
|---|---|---|---|---|
| Age (years) | | | | |
| Mean | 56.4 | 53.4 | 52.1 | 56.7 |
| Range | 44-68 | 47-70 | 37-67 | 49-63 |
| Sex (M/F) | 8/4 | 7/4 | 4/6 | 7/4 |
| Weight (kg) | | | | |
| Mean | 95.7 | 94.3 | 88.5 | 89.5 |
| Range | 75.5-130.2 | 55.7-120.4 | 56.1-125.8 | 58.1-130.3 |
| HbA1c (%) | | | | |
| Mean | 7.7% | 7.2% | 7.4% | 7.4% |
| Range | 6.5-10.2 | 6.7-9.8 | 6.5-9.4 | 6.6-9.4 |
| Previous Treatment: | | | | |
| Diet & Exercise | 8.3% | | 20.0% | 36.4% |
| Metformin | 91.7% | 90.9% | 80.0% | 45.4% |
| Metformin + TZD | | 9.1% | | 18.2% |

",

*(continued next page)*

Signed and Sealed this
Twenty-first Day of May, 2013

Teresa Stanek Rea
*Acting Director of the United States Patent and Trademark Office* and insert

Table 1

|  | Group 1 | Group 2 | Group 3 | Group 4 |
|---|---|---|---|---|
| Age (years) | | | | |
| Mean | 56.4 | 57.4 | 52.1 | 56.7 |
| Range | 44-68 | 47-70 | 37-67 | 49-63 |
| Sex (M/F) | 8/4 | 7/4 | 4/6 | 7/4 |
| Weight (kg) | | | | |
| Mean | 95.7 | 94.3 | 88.5 | 89.5 |
| Range | 75.5-130.2 | 55.7-120.4 | 56.1-125.8 | 58.1-130.3 |
| HbA1c (%) | | | | |
| Mean | 7.7% | 7.9% | 7.4% | 7.4% |
| Range | 6.5-10.2 | 6.7-9.8 | 6.5-9.4 | 6.6-9.4 |
| Previous Treatment: | | | | |
| Diet & Exercise | 8.3% | | 20.0% | 36.4% |
| Metformin | 91.7% | 90.9% | 80.0% | 45.4% |
| Metformin + TZD | | 9.1% | | 18.2% |

--                                                                                                                                                                --, therefor.

In col. 39, lines 36-45, delete

TABLE 2

|  | Group 1 | Group 2 | Group 3 | Group 4 |
|---|---|---|---|---|
| n | 12 | 11 | 10 | 11 |
| Completed the Study | 11 (92%) | 11 (100%) | 10 (100%) | 7 (64%) |
| Subjects Discontinued | 1 (8%) | 0 (0%) | 0 (0%) | 4 (36%) |
| Adverse Events | 1 | 0 | 0 | 1 |
| Withdrew Consent | 0 | 0 | 0 | 3 |

" ", and insert

Table 2

|  | Group 1 | Group 2 | Group 3 | Group 4 |
|---|---|---|---|---|
| n | 12 | 11 | 10 | 11 |
| Completed the Study | 11 (92%) | 11 (100%) | 10 (100%) | 7 (64%) |
| Subjects Discontinued | 1 (8%) | 0 (0%) | 0 (0%) | 4 (36%) |
| Adverse Events | 1 | 0 | 0 | 1 |
| Withdrew Consent | 0 | 0 | 0 | 3 |

-- --, therefor.

In col. 47, lines 60-67, and col. 48, lines 1-9, delete

" TABLE 16

|  | Groups 1 and 2 | Group 3 |
| --- | --- | --- |
| Weeks 1-12 | | |
| Completion Rate | 93% | 89% |
| Withdrawals due to nausea | 3.9% | 5.7% |

TABLE 16-continued

|  | Groups 1 and 2 | Group 3 |
| --- | --- | --- |
| Withdrawals prior to re-randomization | 8.4% | 6.4% |
| Completion Rate | 95% | NA* |
| Withdrawals due to nausea | <1% | NA* |

*NA—not applicable ", and insert

Table 16

|  | Groups 1 and 2 | Group 3 |
| --- | --- | --- |
| Weeks 1-12 | | |
| Completion Rate | 93% | 89% |
| Withdrawals due to nausea | 3.9% | 5.7% |
| Withdrawals prior to re-randomization | 8.4% | 6.4% |
| Weeks 13-24 | | |
| Completion Rate | 95% | NA* |
| Withdrawals due to nausea | <1% | NA* |

*NA - not applicable therefor.

In col. 51, line 62, delete "the need self injection.", and insert -- the need for self injection. --, therefor.

In the Claims

In col. 56, line 66, claim 2, delete "3 days or less, and" and insert -- 3 days or less, --, therefor.

In col. 57, line 21, claim 5, delete "osmotic device" and insert -- osmotic delivery device --, therefor.